(12) United States Patent
Ichikawa et al.

(10) Patent No.: US 8,741,541 B2
(45) Date of Patent: Jun. 3, 2014

(54) COMPOUND, RESIN, PHOTORESIST COMPOSITION, AND METHOD FOR PRODUCING PHOTORESIST PATTERN

(75) Inventors: Koji Ichikawa, Osaka (JP); Isao Yoshida, Osaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 63 days.

(21) Appl. No.: 13/475,594

(22) Filed: May 18, 2012

(65) Prior Publication Data

US 2012/0295201 A1 Nov. 22, 2012

(30) Foreign Application Priority Data

May 20, 2011 (JP) ................................ 2011-113183
Oct. 5, 2011 (JP) ................................ 2011-221031

(51) Int. Cl.
*G03F 7/039* (2006.01)
*G03F 7/30* (2006.01)

(52) U.S. Cl.
USPC ........................................ 430/270.1; 430/326

(58) Field of Classification Search
None
See application file for complete search history.

(56) References Cited

U.S. PATENT DOCUMENTS

| | | | |
|---|---|---|---|
| 2007/0122750 A1 | 5/2007 | Yamaguchi et al. | |
| 2009/0023096 A1* | 1/2009 | Tarutani et al. | 430/281.1 |
| 2009/0035692 A1* | 2/2009 | Tarutani et al. | 430/270.1 |
| 2009/0317744 A1* | 12/2009 | Fuji et al. | 430/270.1 |
| 2010/0047710 A1* | 2/2010 | Yamagishi et al. | 430/270.1 |
| 2011/0236826 A1* | 9/2011 | Hatakeyama et al. | 430/270.1 |
| 2011/0236831 A1* | 9/2011 | Hasegawa et al. | 430/285.1 |
| 2012/0009527 A1* | 1/2012 | Hatakeyama et al. | 430/325 |

FOREIGN PATENT DOCUMENTS

JP 2010-256876 A * 11/2010

* cited by examiner

*Primary Examiner* — Cynthia Hamilton
(74) *Attorney, Agent, or Firm* — Birch, Stewart, Kolasch & Birch, LLP

(57) ABSTRACT

A compound represented by formula (I):

$$R^5 \underset{O}{\overset{T^1}{\diagup}} O \left( L^1 O \right)_m W^1 L^2 \underset{R^2}{\overset{R^1}{-}} O L^3 W^1 (R^4)_u \quad (R^3)_t \qquad (I)$$

wherein
$T^1$ represents a single bond or a C6-C14 aromatic hydrocarbon group,
$L^1$ represents a C1-C17 divalent saturated hydrocarbon group in which a methylene group may be replaced by an oxygen atom or a carbonyl group,
$L^2$ and $L^3$ each independently represent a single bond or a C1-C6 divalent saturated hydrocarbon group in which a methylene group may be replaced by an oxygen atom or a carbonyl group,
ring $W^1$ and ring $W^2$ each independently represent a C3-C36 hydrocarbon ring,
$R^1$ and $R^2$ each independently represent a hydrogen atom, a hydroxyl group, or C1-C6 alkyl group,
$R^3$ and $R^4$ each independently represent a hydroxyl group, or C1-C6 alkyl group,
$R^5$ represents a hydroxyl group or a methyl group,
m represents 0 or 1, and
t and u each independently represent an integer of 0 to 2.

4 Claims, No Drawings

COMPOUND, RESIN, PHOTORESIST COMPOSITION, AND METHOD FOR PRODUCING PHOTORESIST PATTERN

This nonprovisional application claims priority under 35 U.S.C. §119(a) on Patent Applications No. 2011-113183 filed in JAPAN on May 20, 2011 and No. 2011-221031 filed in JAPAN on Oct. 5, 2011, the entire contents of which are hereby incorporated by reference.

FIELD OF THE INVENTION

The present invention relates to compound, resin, a photoresist composition and a method for producing a photoresist pattern.

BACKGROUND OF THE INVENTION

As semiconductor microfabrication employing a lithography process, lithography processes employing ArF excimer laser (wavelength: 193 nm) an exposure system have been intensively studied. A photoresist composition for such lithography process generally contains an acid generator and a resin which varies its solubility for an aqueous alkali solution by the action of an acid.

US2007/122750 discloses a photoresist composition which comprises a resin having structural units represented by the following formulae.

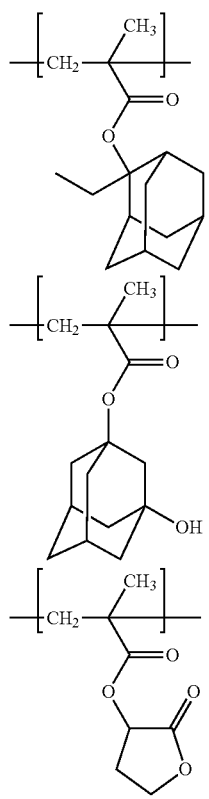

SUMMARY OF THE INVENTION

The present invention is to provide a compound for suitable for a photoresist composition. The present invention relates to the followings:

<1> A compound represented by formula (I):

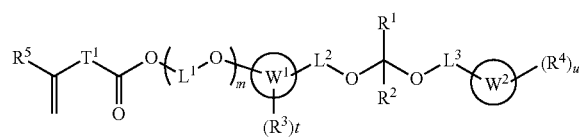

wherein $T^1$ represents a single bond or a C6-C14 aromatic hydrocarbon group, $L^1$ represents a C1-C17 divalent saturated hydrocarbon group in which a methylene group may be replaced by an oxygen atom or a carbonyl group, $L^2$ and $L^3$ each independently represent a single bond or a C1-C6 divalent saturated hydrocarbon group in which a methylene group may be replaced by an oxygen atom or a carbonyl group, ring $W^1$ and ring $W^2$ each independently represent a C3-C36 hydrocarbon ring, $R^1$ and $R^2$ each independently represent a hydrogen atom, a hydroxyl group, or C1-C6 alkyl group, $R^3$ and $R^4$ each independently represent a hydroxyl group, or C1-C6 alkyl group, $R^5$ represents a hydroxyl group or a methyl group, m represents 0 or 1, and t and u each independently represent an integer of 0 to 2.

<2> The compound according to <1>, wherein $T^1$ represents a single bond.

<3> The compound according to <1> or <2>, wherein m represents 0.

<4> The compound according to any one of <1> to <3>, wherein $L^2$ is a carbonyl group.

<5> The compound according to any one of <1> to <4>, wherein $L^3$ is a single bond or a methylene group.

<6> The compound according to any one of <1> to <5>, wherein $L^3$ is a methylene group.

<7> A resin which comprises a structural unit derived from the compound according to any one of <1> to <5>.

<8> The resin according to <7>, which further comprises a structural unit derived from a monomer having an acid-labile group but not being represented by formula (I).

<9> The resin according to <8>, wherein the monomer having an acid-labile group but not being represented by formula (I) is represented by formula (a1-1) or formula (a1-2)

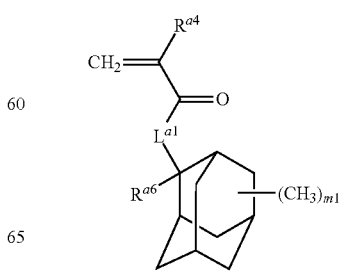

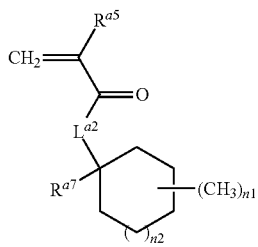
(a1-2)

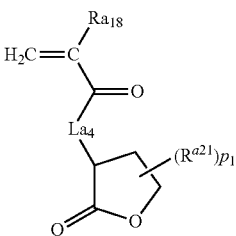
(a3-1)

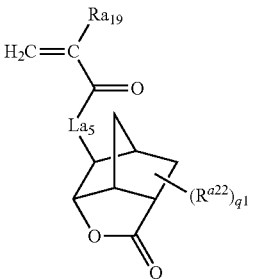
(a3-2)

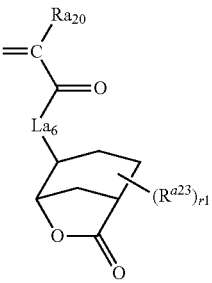
(a3-3)

wherein $L^{a1}$ and $L^{a2}$ each independently represent —O— or *—O—$(CH_2)_{k1}$—CO—O— in which k1 represents an integer of 1 to 7 and * represents a binding site to —CO—, $R^{a4}$ and $R^{a5}$ each independently represent a hydrogen atom or a methyl group, $R^{a6}$ and $R^{a7}$ each independently represent a C1-C8 alkyl group or C3-C10 alicyclic hydrocarbon group, m1 represents an integer of 0 to 14, n1 represents an integer of 0 to 10, and n2 represents an integer of 0 to 3.

<10> The resin according to any one of <7> to <9>, which further comprises a structural unit derived from a monomer having no acid-labile group but having a hydroxyadamantyl group.

<11> The resin according to <10>, in which the monomer having no acid-labile group but having a hydroxyadamantyl group is represented by formula (a2-1)

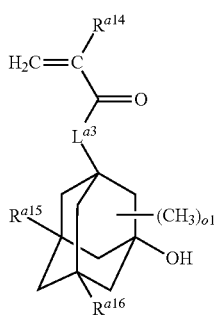
(a2-1)

wherein $L^{a3}$ represents —O— or *—O—$(CH_2)_{k2}$—CO—O— in which k2 represents an integer of 1 to 7 and * represents a binding site to —CO—, $R^{a14}$ represent a hydrogen atom or a methyl group, $R^{a15}$ and $R^{a16}$ each independently represent a hydrogen atom, a methyl group, or a hydroxy group, and o1 represents an integer of 0 to 10.

<12> The resin according to any one of <7> to <11>, which further comprises a structural unit derived from a monomer having no acid-labile group but having a lactone ring.

<13> The resin according to <12>, in which the monomer having no acid-labile group but having a lactone ring is at least one selected from the group consisting of a monomer represented by formula (a3-1), a monomer represented by formula (a3-2) and a monomer represented by formula (a3-3)

wherein $L^{a4}$, $L^{a5}$ and $L^{a6}$ each independently represent —O— or *—O—$(CH_2)_{k3}$—CO—O— in which k3 represents an integer of 1 to 7 and * represents a binding site to —CO—, $R^{a18}$, $R^{a19}$ and $R^{a20}$ represent a hydrogen atom or a methyl group, $R^{a21}$ represents a C1-C4 alkyl group, $R^{a22}$ and $R^{a23}$ each independently represent a carboxy group, a cyano group or a C1-C4 alkyl group, p1 represents an integer of 0 to 5, q1 and r1 each independently represent an integer of 0 to 3.

<14> A photoresist composition, which comprises the resin according to any one of <7> to <13>, an acid generator and a solvent.

<15> The photoresist composition according to <14>, which further comprises a resin having a structural unit derived from a monomer having no acid-labile group but having a fluorine atom.

<16> The photoresist composition according to <15>, wherein the structural unit derived from a monomer having no acid-labile group but having a fluorine atom is represented by formula (a4-1):

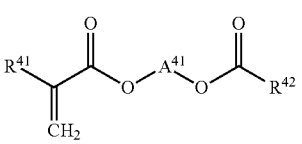
(a4-1)

wherein $R^{41}$ represents a hydrogen atom or a methyl group, $A^{41}$ represents a moiety represented by formula (a-4-g1):

$$-(A^{40}-X^{40})_{ss}-A^{43}- \quad (\text{a4-g1})$$

in which ss represents an integer of 0 to 2, $A^{40}$ and $A^{43}$ respectively represent a C1-C5 alipathic aliphatic hydrocarbon group which may have a substituent and $X^{40}$ respectively represent an oxygen atom, a carbonyl group, a carbonyloxy group, or an oxycarbonyl group, and $R^{42}$ represents a C1-C18 aliphatic hydrocarbon group in which a methylene group may be replaced by an oxygen atom or a carbonyl group.

<17> The photoresist composition according to any one of <14> to <16>, wherein
the acid generator is a salt represented by formula (B1)

$$Z^+ \ \ ^-O_3S \underset{Q^2}{\overset{Q^1}{\underset{|}{\overset{|}{C}}}} L^{b1} \diagdown Y \quad (B1)$$

wherein $Q^1$ and $Q^2$ respectively represent a fluorine atom or a C1-C6 perfluoroalkyl group,
$L^{b1}$ represents a methylene group or a C1-C17 saturated hydrocarbon group in which a methylene group may be replaced by —O— or —CO—, Y represents a C1-C18 alkyl group which may have a substituent or a C3-C18 alicyclic hydrocarbon group which may have a substituent, where a methylene of the alkyl group and a methylene of the alicyclic hydrocarbon group may be replaced respectively by an oxygen atom, a sulfonyl group or a carbonyl group, and
$Z^+$ represents an organic cation.

<18> The photoresist composition according to <17>, wherein Y represents a C3-C18 alicyclic hydrocarbon group which may have a substituent.

<19> A process for producing a photoresist pattern comprising the following steps (1) to (5):

(1) a step of applying the photoresist composition according to any one of <13> to <18> on a substrate, (2) a step of forming a photoresist film by conducting drying, (3) a step of exposing the photoresist film to radiation, (4) a step of baking the exposed photoresist film, and (5) a step of developing the baked photoresist film to thereby form a photoresist pattern.

DESCRIPTION OF PREFERRED EMBODIMENTS

The present invention will be described in detail.

The compound of the present invention is represented by formula (I):

(I)

wherein
$T^1$ represents a single bond or a C6-C14 aromatic hydrocarbon group, $L^1$ represents a C1-C17 divalent saturated hydrocarbon group in which a methylene group may be replaced by an oxygen atom or a carbonyl group, $L^2$ and $L^3$ each independently represent a single bond or a C1-C6 divalent saturated hydrocarbon group in which a methylene group may be replaced by an oxygen atom or a carbonyl group, ring $W^1$ and ring $W^2$ each independently represent a C3-C36 hydrocarbon ring, $R^1$ and $R^2$ each independently represent a hydrogen atom, a hydroxyl group, or C1-C6 alkyl group, $R^3$ and $R^4$ each independently represent a hydroxyl group, or C1-C6 alkyl group, $R^5$ represents a hydroxyl group or a methyl group, m represents 0 or 1, and t and u each independently represent an integer of 0 to 2.

Hereinafter, the compound represented by formula (I) is sometimes referred to as "Compound (I)".

In formula (I), $T^1$ represents a single bond or a C6-C14 aromatic hydrocarbon group. Such aromatic hydrocarbon group includes phenyl group, naphthyl group or antlyl group. $T^1$ preferably represents a single bond.

The saturated hydrocarbon group represented by $L^1$ includes a liner chain alkanediyl group, a branched chain alkanediyl group and cyclic saturated hydrocarbon group.

Such cyclic saturated hydrocarbon group includes a monocyclic or dicyclic divalent alicyclic hydrocarbon group, and a group in which two or more of these alkanediyl and alicyclic hydrocarbon groups have been combined.

Examples of such liner chain alkanediyl groups include a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of such branched chain alkanediyl groups include a group formed by attaching a C1-C4 alkyl group (e.g., methyl group, ethyl group, propyl group, butyl group) to a linear chain alkyl group, such as a butan-1,3-diyl group, a 2-methylpropane-1,3-diyl group, a 2-methylpropane-1,2-diyl group, a pentane-1,4-diyl group, and a 2-methylbutane-1,4-diyl group.

Examples of divalent alicyclic hydrocarbon groups include cycloalkanediyl groups such as a cyclohexane-1,2-diyl group, a 1-methylcyclohexane-1,2-diyl group, cyclohexane-1,4-diyl and a polycyclic divalent alicyclic hydrocarbon groups such as an amadantanediyl group.

When $L^1$ represents a C1-C17 divalent saturated hydrocarbon group in which a methylene group has been replaced by an oxygen atom or a carbonyl group, $L^1$ is preferably represented by formula (L1-A).

(L1-A)

in which $L^{11}$ represents a C1-C16 saturated hydrocarbon group,
* at the left side represents a binding bond to an oxygen atom,
* at the right side represents a binding bond to ring $W^1$.

$L^{11}$ preferably represents a C1-C12 alkanediyl group, preferably —$CH_2$—, —$(CH_2)_2$—, —$(CH_2)_4$—, —$(CH_2)_8$— or —$(CH_2)_{12}$—.

$L^2$ and $L^3$ each independently represent a single bond or a C1-C6 divalent saturated hydrocarbon group in which a methylene group may be replaced by an oxygen atom or a carbonyl group.

The saturated hydrocarbon group represented by $L^2$ or $L^3$ includes a liner chain alkanediyl group and a branched chain alkanediyl group.

Examples of the saturated hydrocarbon group represented by $L^2$ or $L^3$ include a liner chain alkanediyl groups such as a methylene group, an ethylene group, a propane-1,3-diyl group, a propane-1,2-diyl group, a butane-1,4-diyl group, a butane-1,3-diyl group, a pentane-1,5-diyl group and a hexane-1,6-diyl group; and a branched chain alkanediyl groups such as a group formed by attaching a C1-C4 alkyl group (e.g., methyl group, ethyl group, propyl group, butyl group) to a linear chain alkyl group, such as a butan-1,3-diyl group, a 2-methylpropane-1,3-diyl group, a 2-methylpropane-1,2-diyl group, a pentane-1,4-diyl group, and a 2-methylbutane-1,4-diyl group.

When $L^2$ or $L^3$ represents a C1-C17 divalent saturated hydrocarbon group in which a methylene group has been replaced by an oxygen atom or a carbonyl group, Examples of $L^2$ or $L^3$ include —CO— and —CO—O—$CH_2$—CO—.

$L^2$ represents preferably a single bond, a methylene group or —CO—, more preferably a single bond or —CO—, and still more preferably —CO—.

$L^3$ represents preferably, a single bond, a methylene group or —CO—, more preferably a single bond or a methylene group, and still more preferably a methylene group.

The ring $W^1$ and ring $W^2$ each independently represent a C3-C36 hydrocarbon ring.

Herein, "hydrocarbon ring" represented by ring $W^1$ and ring $W^2$ refers to a hydrocarbon ring consisting of carbon atoms and hydrogen atoms.

Such hydrocarbon ring includes preferably C5-C18 hydrocarbon ring, more preferably C5-C12 hydrocarbon ring, which may be a monocyclic, bicyclic or tricyclic hydrocarbon group. Specific examples of the hydrocarbon ring include a cycloalkyl group such as cyclohexane, adamantane ring and an aromatic group such as benzene ring, preferably adamantane ring.

The alkyl group represented by $R^1$, $R^2$, $R^3$ and $R^4$ includes a methyl group, an ethyl group, a propyl group, a butyl group, a pentyl group, and a hexyl group.

$R^1$ and $R^2$ each independently represent preferably a hydrogen atom, a hydroxyl group, a methyl group, or an ethyl group, more preferably a hydrogen atom, a hydroxyl group, or a methyl group, still more preferably a hydrogen atom.

$R^3$ and $R^4$ each independently represent preferably a hydroxyl group, a methyl group, or an ethyl group, more preferably a hydrogen atom or a methyl group.

In the formula (I), examples of the moiety represented by formula (I-A)

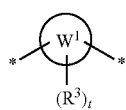

(I-A)

wherein $R^3$, ring $W^1$ and t are defined as above include the formulae as follow.

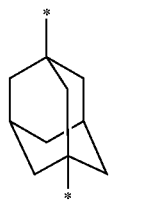

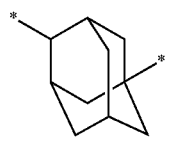

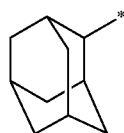

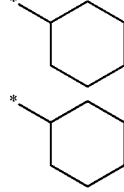

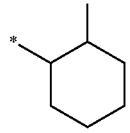

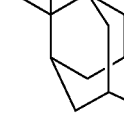

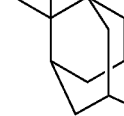

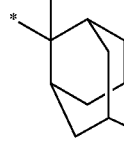

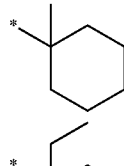

Examples of the ring $W^2$ include the formulae as follow.
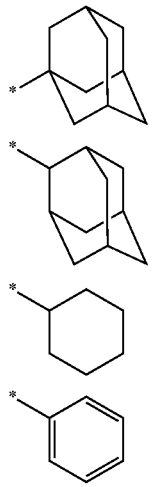
The compound represented by formula (I) includes the following formula.
(I-1)
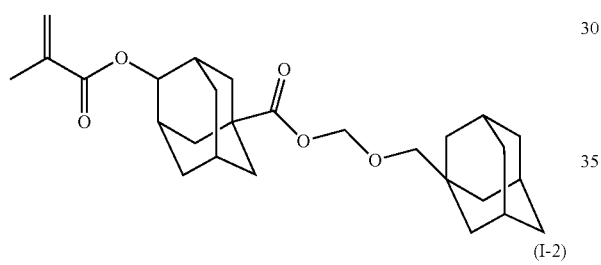
(I-2)
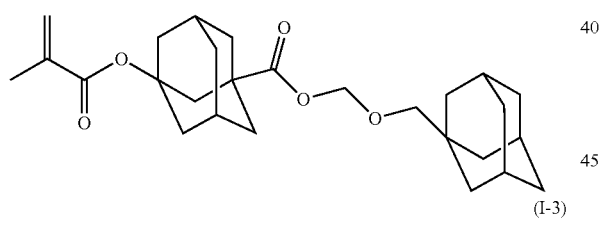
(I-3)
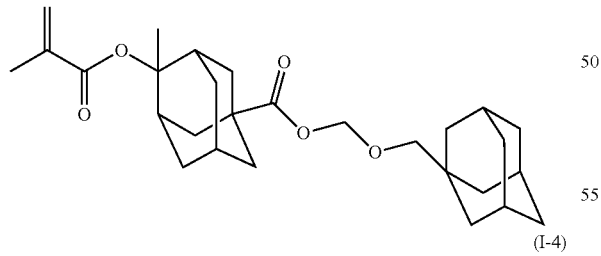
(I-4)
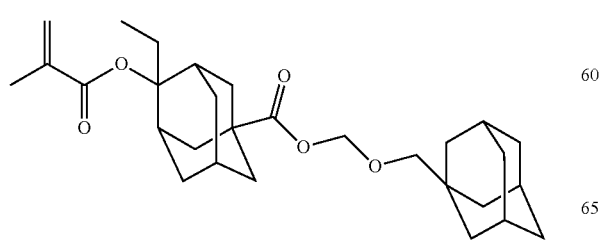
(I-5)
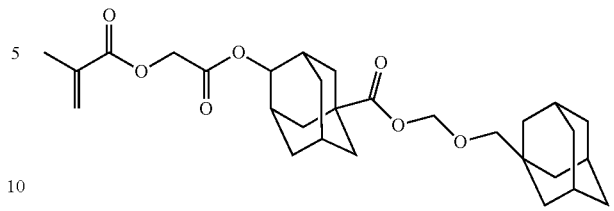
(I-6)
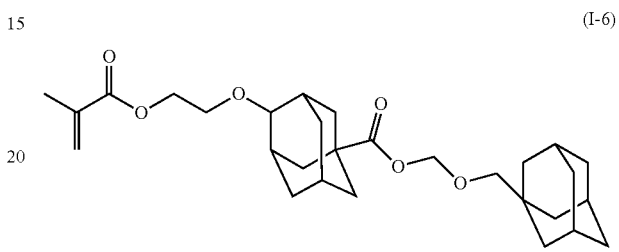
(I-7)
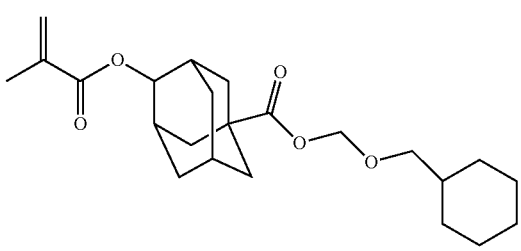
(I-8)
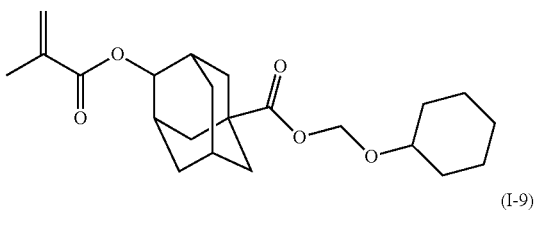
(I-9)
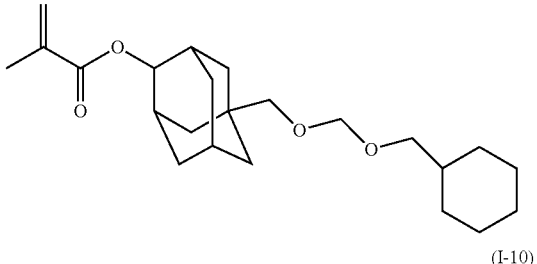
(I-10)
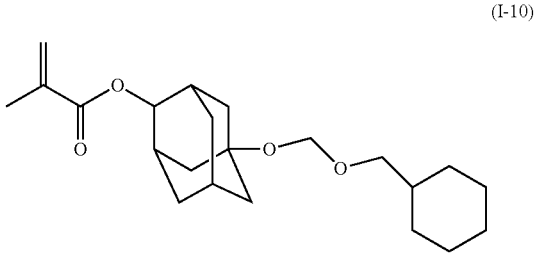

(I-11)
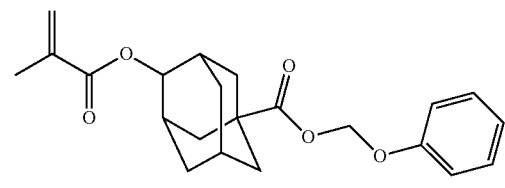
(I-12)
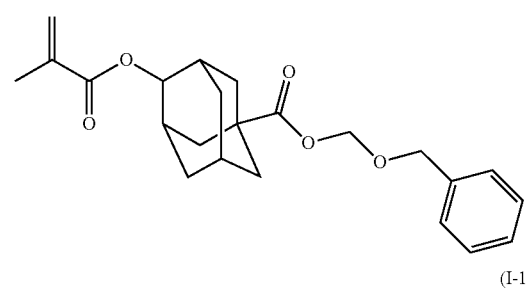
(I-13)
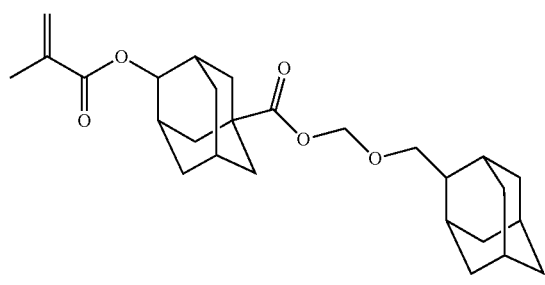
(I-14)
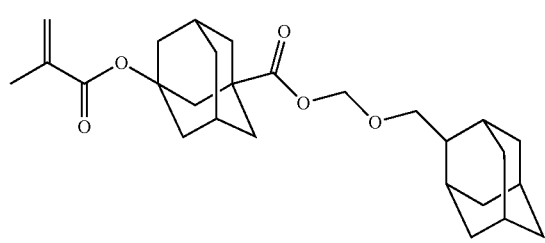
(I-15)
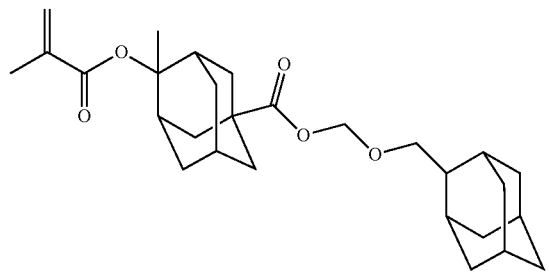
(I-16)
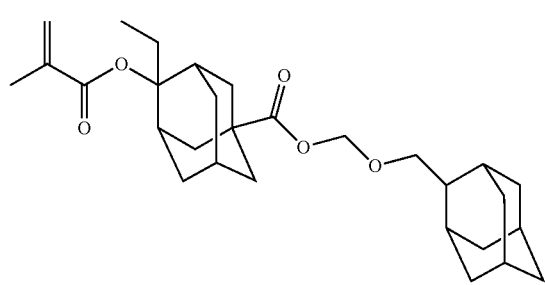
(I-17)
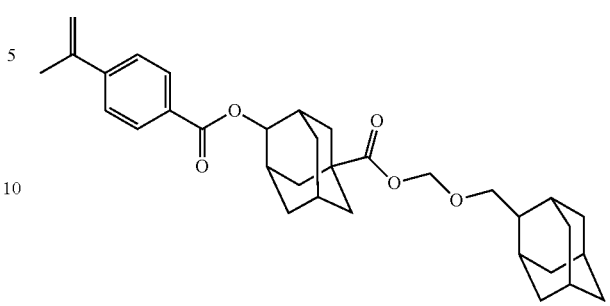
(I-18)
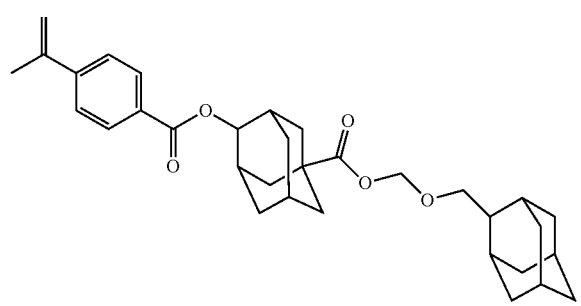
(I-19)
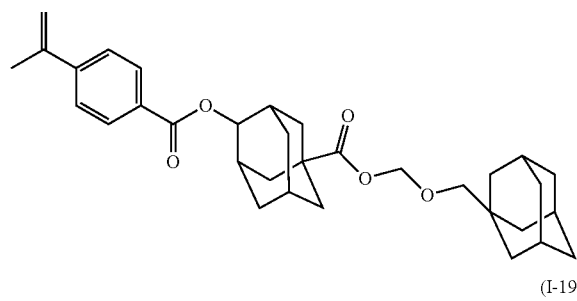
(I-20)
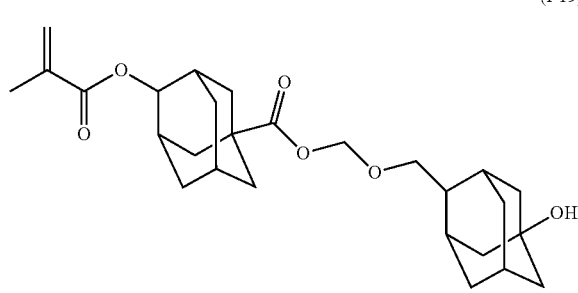
(I-21)
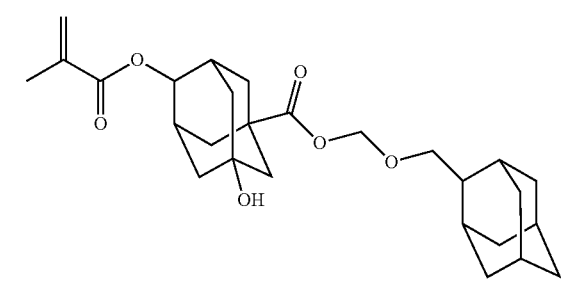

(I-22)
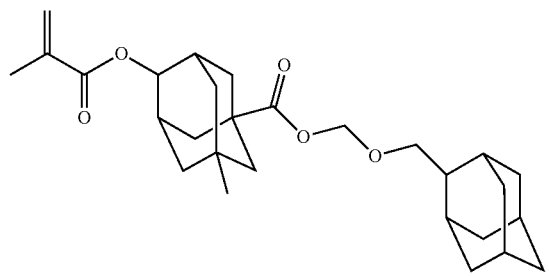
(I-23)
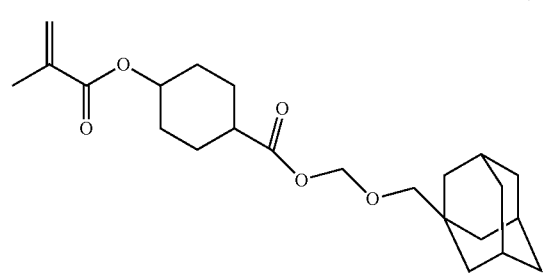
(I-24)
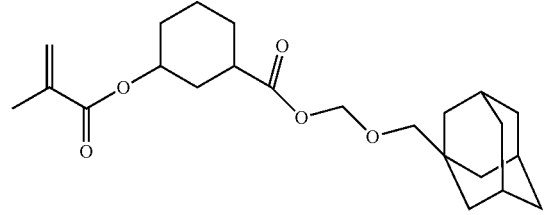
(I-25)
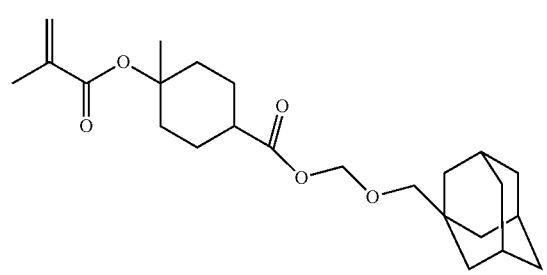
(I-26)
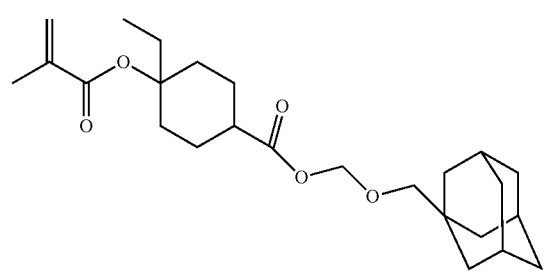
(I-27)
(I-28)
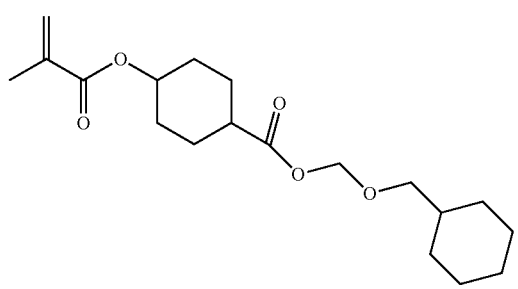
(I-29)
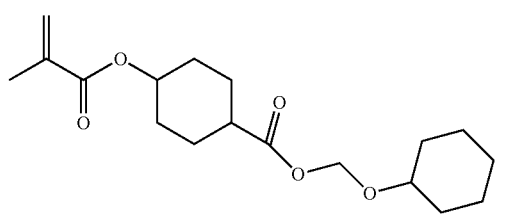
(I-30)
(I-31)

(I-32)
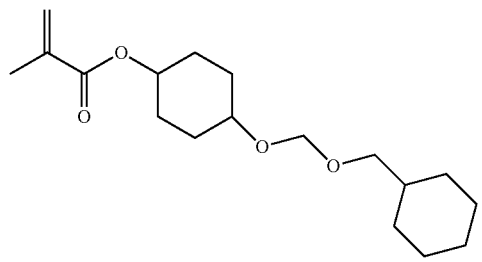
(I-37)
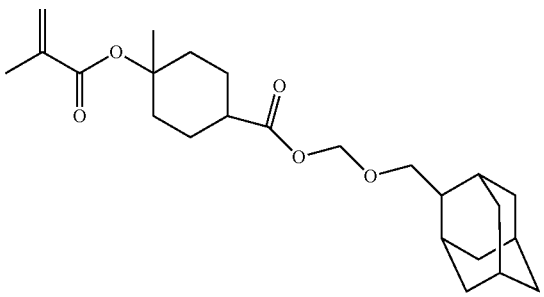
(I-33)
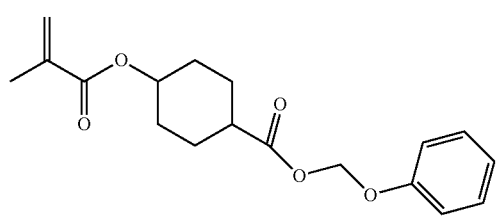
(I-38)
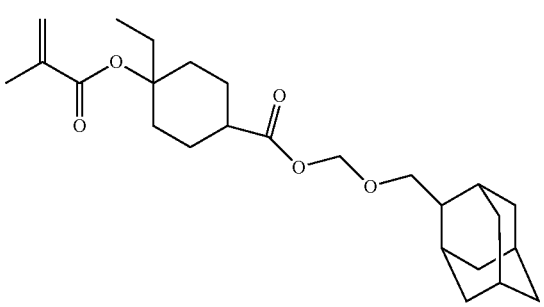
(I-34)
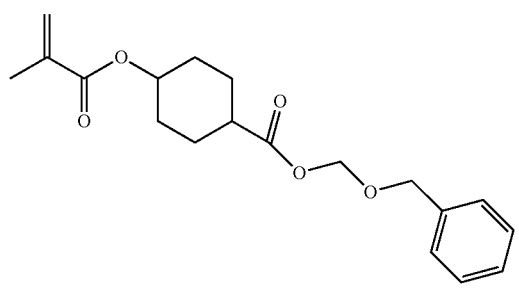
(I-39)
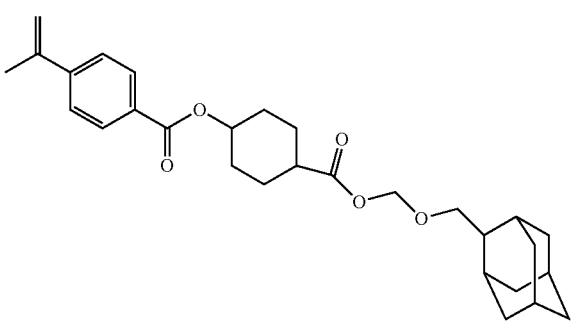
(I-35)
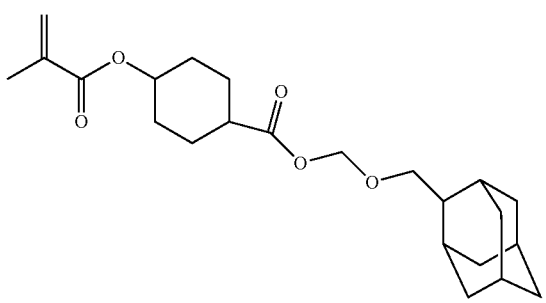
(I-40)
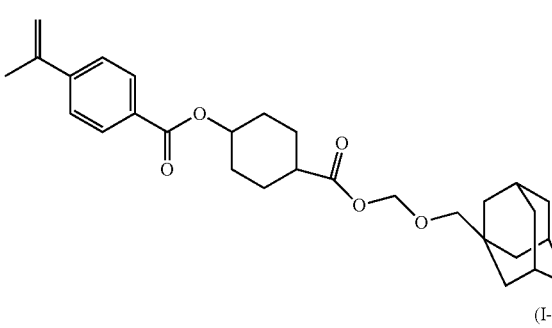
(I-36)
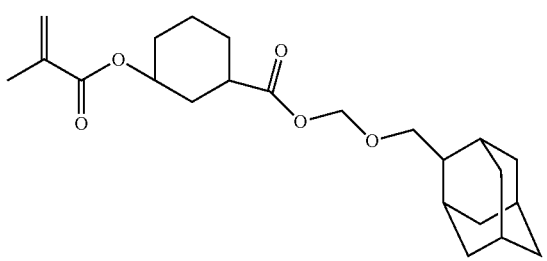
(I-41)
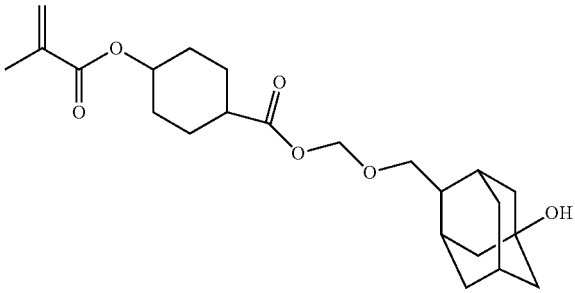

(I-42)
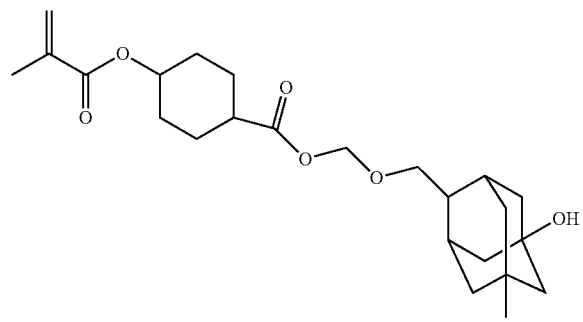
(I-43)
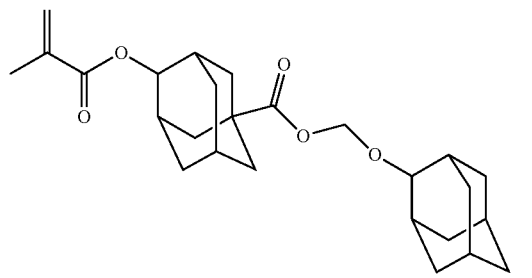
(I-44)
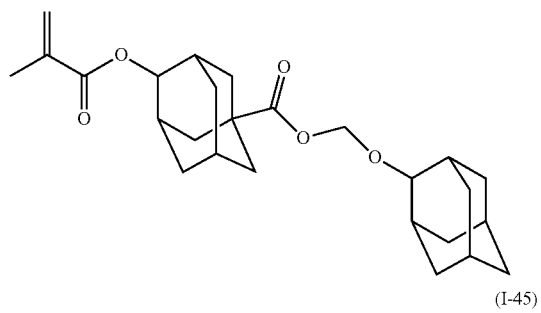
(I-45)
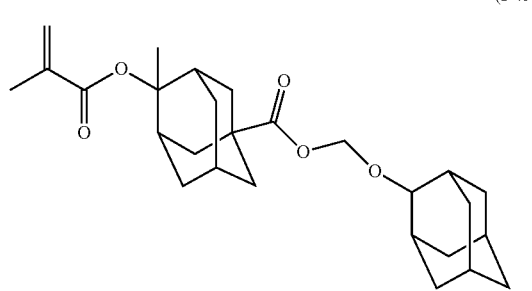
(I-46)
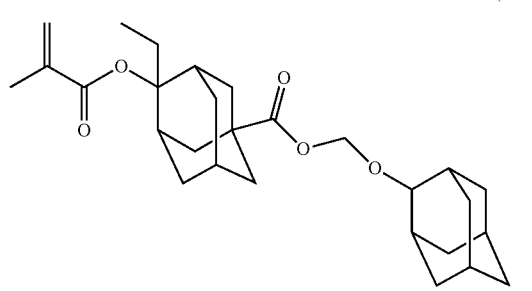
(I-47)
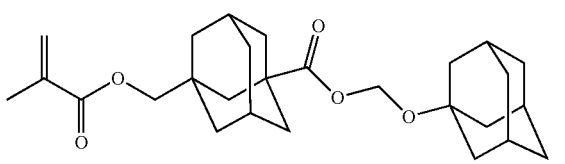
(I-48)
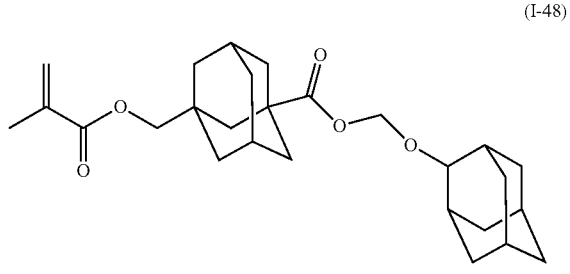
(I-49)
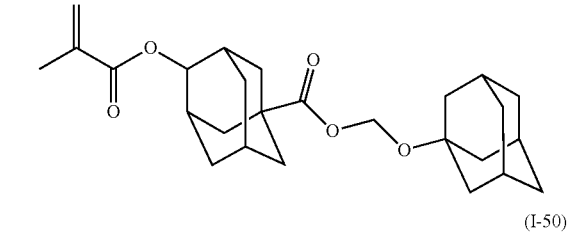
(I-50)
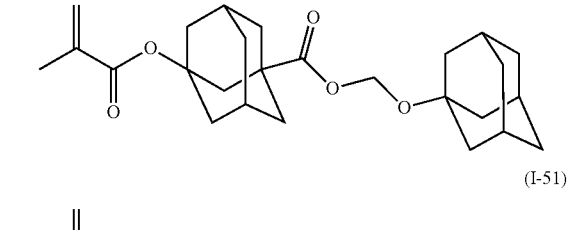
(I-51)
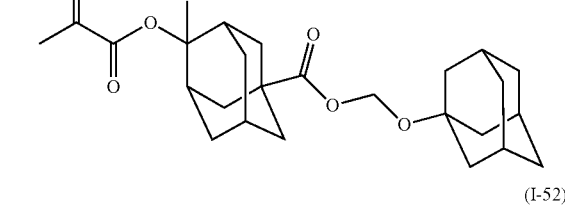
(I-52)
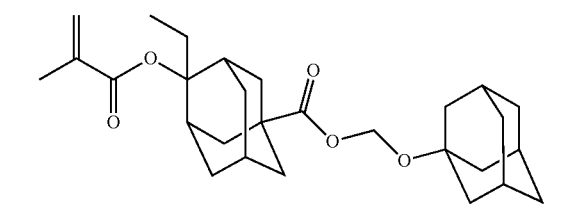
(I-53)
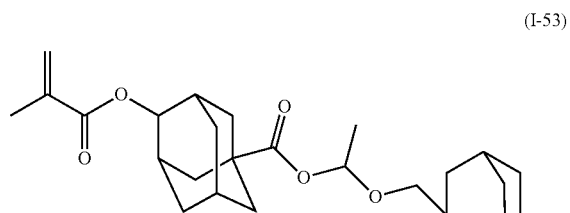

(I-54)

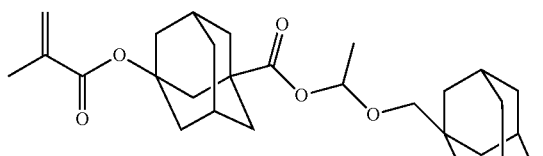

(I-55)

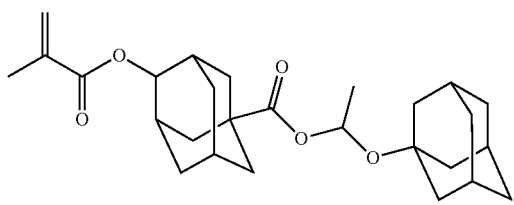

(I-56)

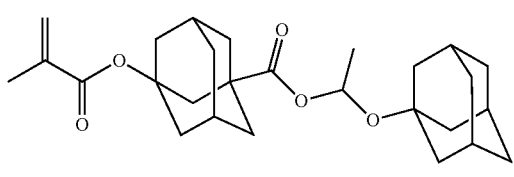

(I-57)

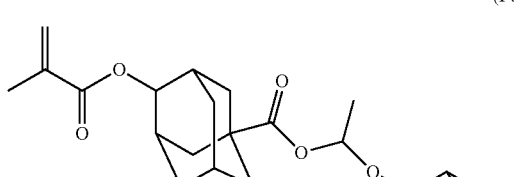

(I-58)

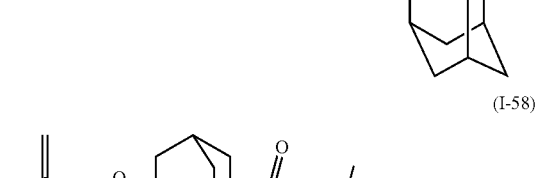

Examples of the compound represented by formula (I) further include the same compounds as those represented by any one of formulae (I-1) to (I-58) except that Moiety M has been replaced by Moiety A.

(Moiety M)

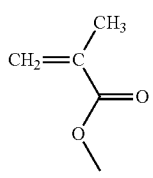

(Moiety A)

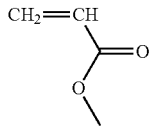

The process for producing the compound represented by formula (I) will be described, taking as an example the compound of formula (IA) representing the formula (I) in which $T^1$ represents a single bond, m represents 0 and $L^2$ represents a carbonyl group.

(IA)

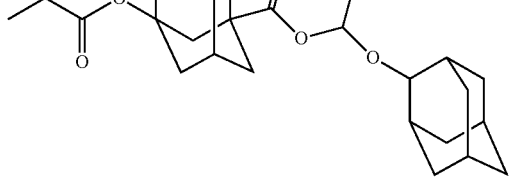

The compound of formula (IA) can be produced by reacting the compound represented by formula (IA-c) and the compound represented by formula (IA-d) in the presence of a catalyst such as N-methylpyrrolidine in a solvent such as methylisobutylketone or dimethylformamide

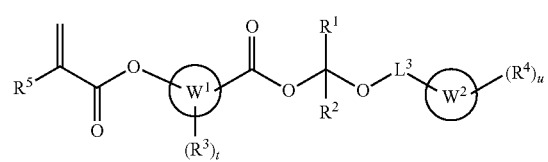

(IA-c)

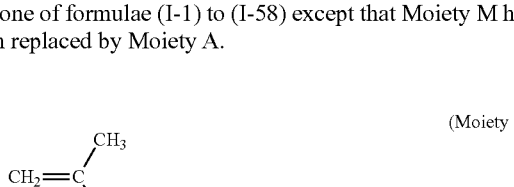

(IA)

wherein the ring $W^1$, the ring $W^2$, $L^3$, $R^1$, $R^2$, $R^3$, $R^4$, $R^5$, t and u are defined as above, $X^2$ represents a halogen atom or (meth)acryloyloxy group.

Examples of halogen atom represented by $X^2$ include a fluorine atom, a chlorine atom, a bromine atom and an iodine atom, preferably a chlorine atom.

The compound of formula (IA-d) includes (meth)acrylchloride or (meth)acrylchloride anhydride.

Herein, each of "(meth)acryloyl", "(meth)acryl" and "(meth)acrylate" refers to correctively "acryloyl and methacryloyl", "acryl and methacryl" and "acrylate and methacrylate".

The compound of formula (IA-c) can be produced by reacting the compound represented by formula (IA-a) and the compound represented by formula (IA-b) in the presence of a basic catalyst such as triethylamine in a solvent such as dimethylformamide, as shown bellow:

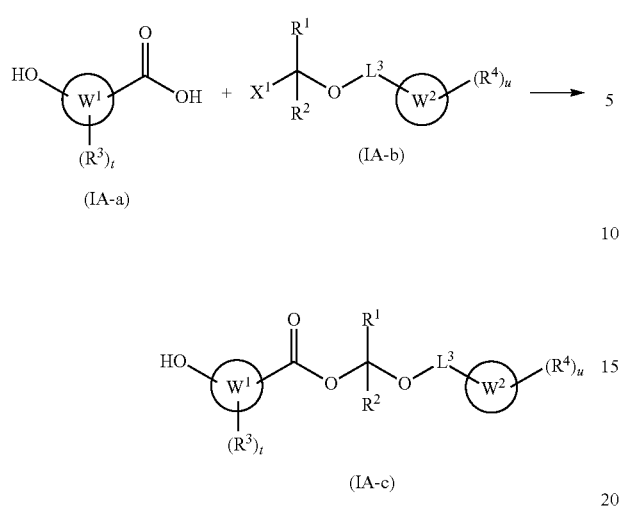

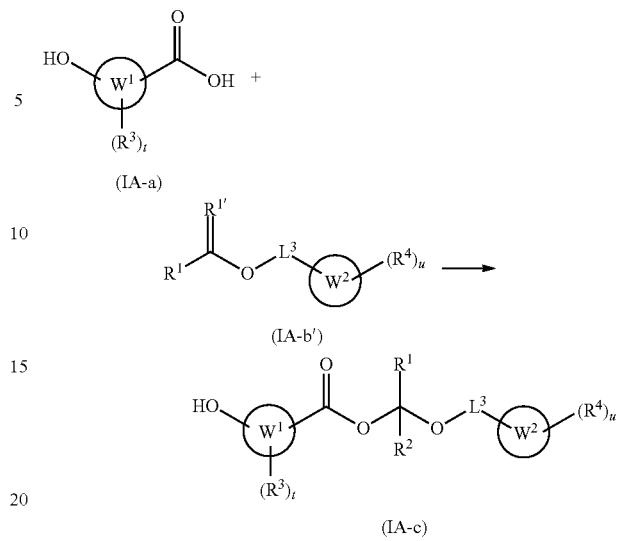

wherein the ring $W^1$ the ring $W^2$, $L^3$, $R^1$, $R^2$, $R^3$, $R^4$, $R^5$, t and u are defined as above, $X^1$ represents a halogen atom or (meth)acryloyloxy group.

Examples of halogen atom represented by $X^1$ include a fluorine atom, a chlorine atom, a bromine atom and an iodine atom.

Examples of the compound represented by (1A-a) include those shown as follow.

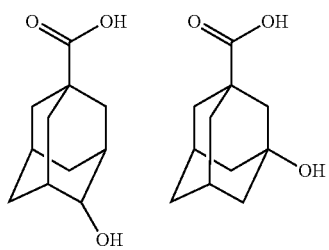

Examples of the compound represented by (1A-b) include those shown as follow.

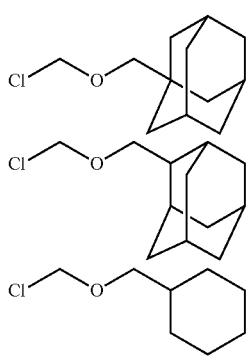

The compound of formula (IA-c) can also be produced by reacting the compound represented by formula (IA-a) and the compound represented by formula (IA-b') in the presence of an acid catalyst such as camphorsulfonic acid in a solvent such as chloroform wherein the ring $W^1$, the ring $W^2$, $L^3$, $R^1$, $R^2$, $R^3$, $R^4$, $R^5$, t and u are defined as above, and $R^{1'}$ represents a C1-C6 alkylidene group.

The compound represented by formula (IA-b') includes those shown as follow.

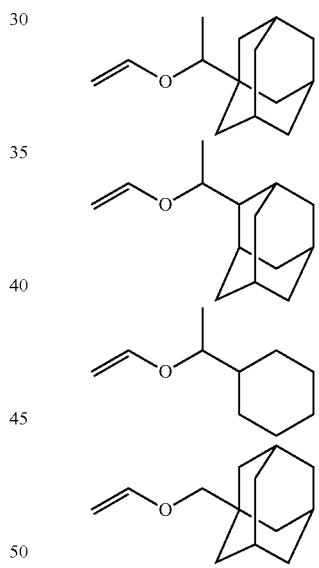

The compound of formula (IA-c) can also be produced by conducting the same reactions as mentioned above except that the compound represented by formula (IA-a1) is used instead of the compound represented by formula (IA-a), followed by reducing the resulting compound

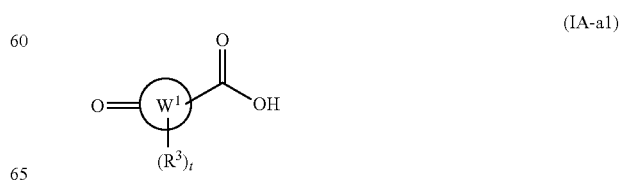

wherein the ring $W^1$, $R^3$ and t are defined as above.

The compound represented by formula (IA-a1) includes the following compound.

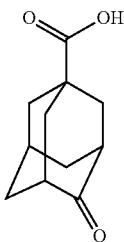

As the compounds represented by formula (IA-a), formula (IA-a1), formula (IA-b) and formula (IA-d), those available on the market can be used.

The compound represented by formula (I) is suitable for a monomer of a resin, preferably a resin for the photoresist composition. The resin comprising a structural unit derived from the compound represented by formula (I) is one aspect of the present invention. The resin of the present invention comprises a structural unit derived from the compound represented by formula (I) in an amount of preferably 1 to 50% by mole, more preferably 3 to 40% by mole, still preferably 5 to 30% by mole, relative to the total structural unit in the resin.

The resin of the present invention may further comprise a structural unit derived from a monomer having an acid-labile group but not being represented by formula (I). Hereinafter, such monomer having an acid-labile group but not being represented by formula (I) is sometimes referred to as "compound (a1)". The resin can have two or more kinds of structural units having an acid-labile group. Herein, "acid-labile group" means a group which has a leaving group capable of being eliminated by the action of an acid thereby to be converted into a hydrophilic group such as a hydroxyl group or carboxyl group.

Examples of the acid-labile group include a group represented by the formula (1):

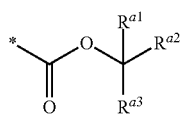

(1)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group, and * represents a binding position,
and a group represented by the formula (2)

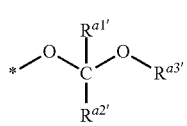

(2)

wherein $R^{a1'}$ and $R^{a2'}$ independently each represent hydrogen atom or a C1-C12 hydrocarbon group, and $R^{a3'}$ represents a C1-C20 hydrocarbon group, or $R^{a3'}$ together with $R^{a1'}$ and $R^{a2'}$ represents a C2-C20 divalent hydrocarbon group in which a methylene group of the divalent hydrocarbon group may be replaced by —O— or —S—, and * represents a binding position.

Specific examples of the C1-C8 alkyl group include a methyl group, an ethyl group, a propyl group, an isopropyl group, a butyl group, a pentyl group, a hexyl group, a heptyl group and an octyl group.

Specific examples of the C1-C12 alkyl group include a methyl group, an ethyl group, a propyl group, an isopropyl group, a butyl group, a pentyl group, a hexyl group, a heptyl group, an octyl group, nonyl group and decyl group.

The alicyclic hydrocarbon group may be monocyclic or polycyclic Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic a cyclic hydrocarbon group such as a decahydronaphthyl group, an adamantyl group, a norbornyl group, a methylnorbornyl group, and the followings.

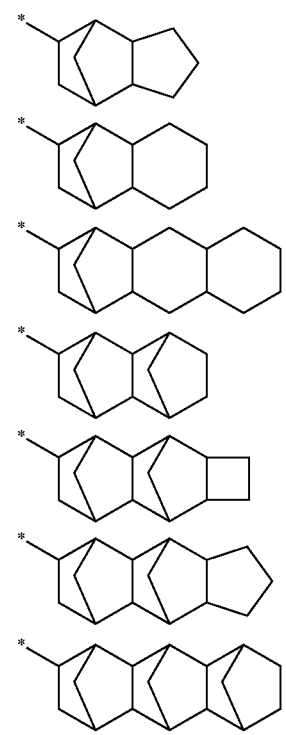

The alicyclic hydrocarbon group preferably has 3 to 16 carbon atoms.

When $R^{a1}$ and $R^{a2}$ of formula (1) are bonded each other to form a C2-C20 divalent hydrocarbon group, the moiety represented by —C($R^{a1}$) ($R^{a2}$) ($R^{a3}$) includes the following groups and the ring preferably has 3 to 12 carbon atoms.

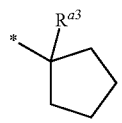

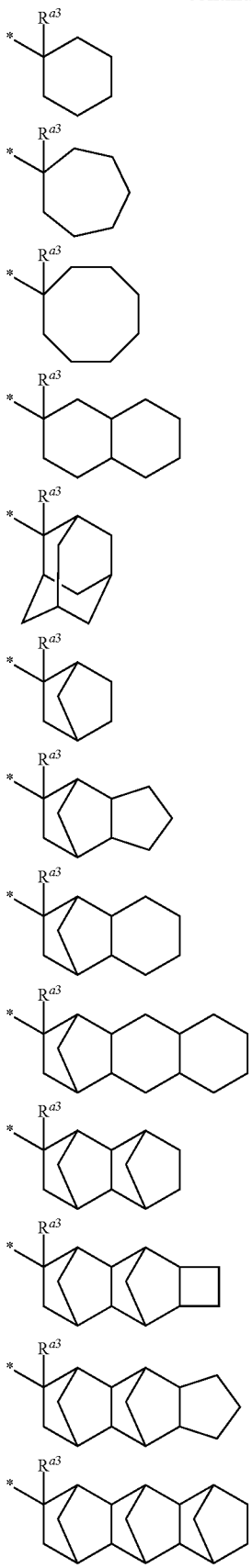

wherein $R^{a3}$ is the same as defined above and * represents a binding position to —O— of formula (1).

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyladaman-2-tyloxycarbonyl group, and the group represented by the formula (1) wherein $R^{a1}$ and $R^{a2}$ are C1-C8 alkyl groups and $R^{a3}$ is an adamantyl group such as a 1-(1-adaman-1-yl)-1-alkylalkoxycarbonyl group are preferable.

As to formula (2), examples of the hydrocarbon group include an aliphatic hydrocarbon group, an alicyclic hydrocarbon group and an aromatic hydrocarbon group.

Examples of the aliphatic hydrocarbon group and the alicyclic hydrocarbon group include the same as described above. Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Divalent hydrocarbon group represented by $R^{a1'}$, $R^{a2'}$ and $R^{a3'}$ include those mentioned above as $R^{a1}$ and $R^{a2}$.

It is preferred that at least one of $R^{a1'}$ and $R^{a1'}$ and $R^{a2'}$ is a hydrogen atom.

Examples of the group represented by formula (2) include the following.

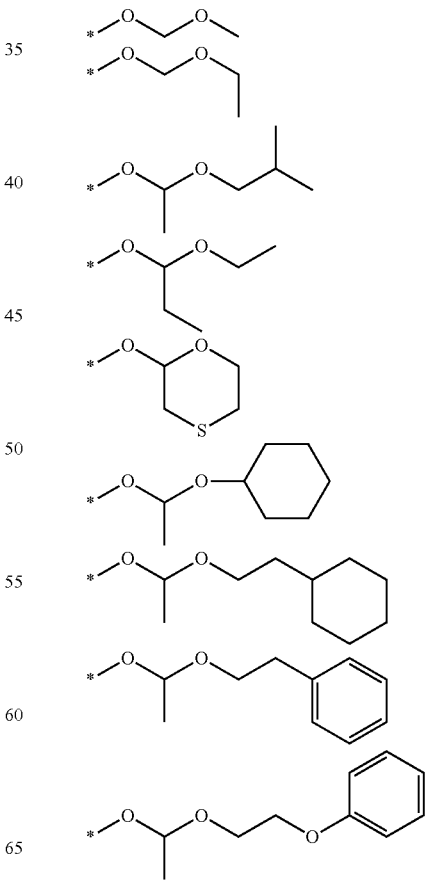

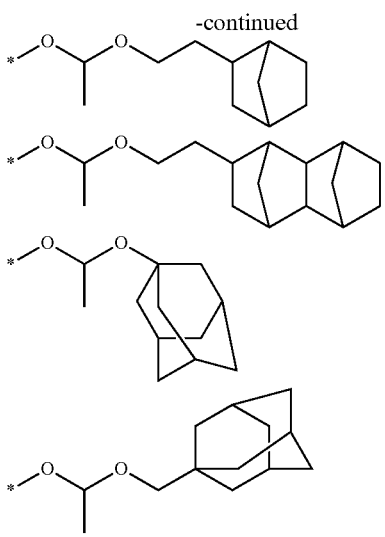

Preferred monomer (a1) is a monomer having an acid-labile group and carbon-carbon double bond but not being represented by formula (I), and more preferred monomer (a1) is a (meth)acrylic monomer having an acid-labile group but not being represented by formula (I).

Examples of such (meth)acrylic compound include (meth)acrylic compounds having a C5-C20 alicyclic hydrocarbon group. The resin obtained from monomer (a1) which has a bulky structure such as the above-mentioned alicyclic hydrocarbon group can provide a photoresist pattern with improved resolution.

The (meth)acrylic compounds having a C5-C20 alicyclic hydrocarbon group include preferably the compound represented by formula (a1-1) and the compound represented by formula (a1-2). Hereinafter, the compound represented by formula (a1-1) and the compound represented by formula (a1-2) are respectively referred to as "compound (a1-1)" and "compound (a1-2)".

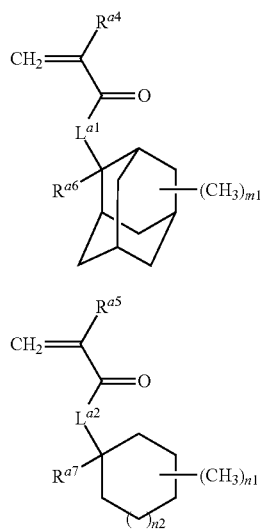

wherein $L^{a1}$ and $L^{a2}$ each independently represent —O— or *—O—$(CH_2)_{k1}$—CO—O— in which k1 represents an integer of 1 to 7 and * represents a binding site to —CO—, $R^{a4}$ and $R^{a5}$ each independently represent a hydrogen atom or a methyl group,
$R^{a6}$ and $R^{a7}$ each independently represent a C1-C8 alkyl group or C3-C10 alicyclic hydrocarbon group,
m1 represents an integer of 0 to 14,
n1 represents an integer of 0 to 10, and
n2 represents an integer of 0 to 3.
$L^{a1}$ and $L^{a2}$ each independently represent —O— or *—O—$(CH_2)_{k1}$—CO—O— in which k1 represents an integer of 1 to 7 and * represents a binding site to —CO—.

Each of $L^{a1}$ and $L^{a2}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

$R^{a4}$ and $R^{a5}$ each preferably represent a methyl group. The alkyl groups represented by $L^{a6}$ and $L^{a7}$ include a methyl group, an ethyl group, a propyl group, a butyl group, a pentyl group, a hexyl group, a heptyl group and an octyl group, and preferably C1-C6 alkyl group.

The alicyclic hydrocarbon group represented by $L^{a6}$ and $L^{a7}$ may be monocyclic or polycyclic, which include a cycloalkyl group such as a cyclopentyl group, a cyclohexyl group, a methylcyclohexyl group, a dimethylcyclohexyl group, a cycloheptyl group, or a cyclooctyl group; and a polycyclic saturated hydrogencarbon group such as a decahydronaphthyl group, an adamantyl group, a norbornyl group, a methylnorbornyl group, and the followings.

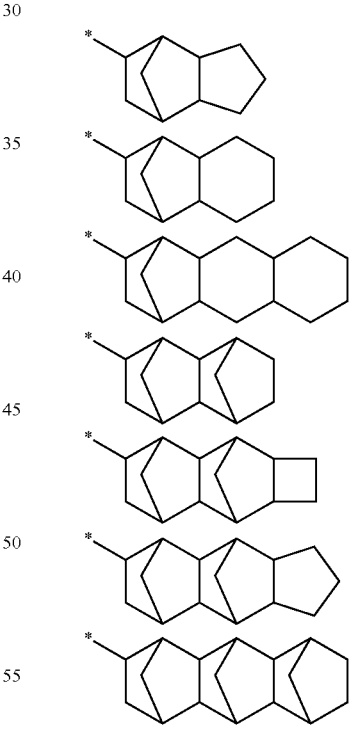

The alicyclic hydrocarbon group has preferably 1 to 8 carbon atoms, more preferably 1 to 6 carbon atoms.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the compounds mentioned in JP2010-204646A. As the monomer represented by the formula (a1-1), preferred are monomer represented by formulae (a1-1-1), (a1-1-2), (a1-1-

3), (a1-1-4), (a1-1-5), (a1-1-6), (a1-1-7) and (a1-1-8), and more preferred are monomer represented by formulae (a1-1-1), (a1-1-2), (a1-1-3), (a1-1-4).

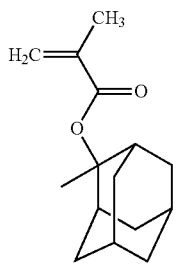
(a1-1-1)

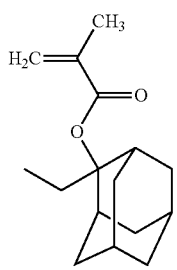
(a1-1-2)

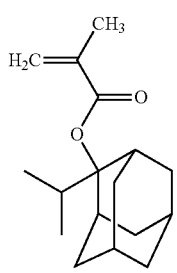
(a1-1-3)

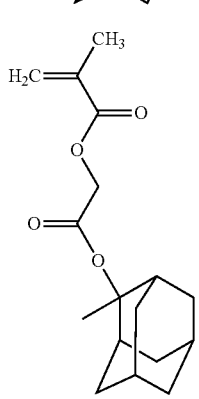
(a1-1-4)

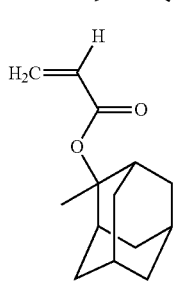
(a1-1-5)

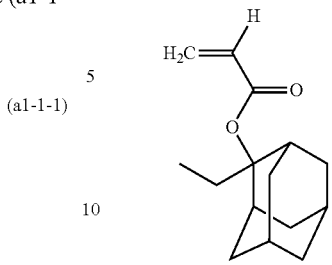
(a1-1-6)

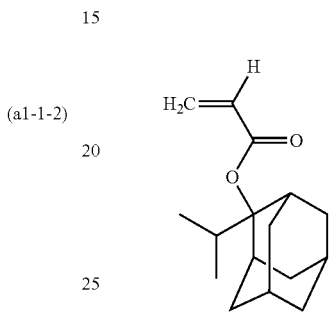
(a1-1-7)

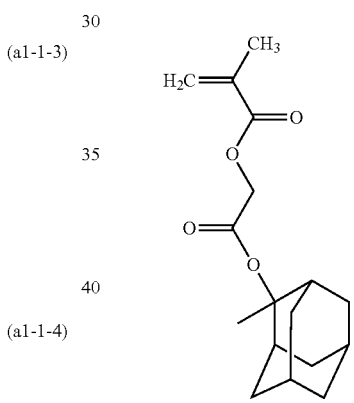
(a1-1-8)

Monomers (a1-1) include preferably 2-methylamadantane-2-yl(meth)acrylate, 2-ethylamadantane-2-yl(meth)acrylate and 2-isopropylamadantane-2-yl(meth)acrylate, and more preferably 2-methylamadantane-2-yl methacrylate, 2-ethylamadantane-2-yl methacrylate and 2-isopropylamadantane-2-yl methacrylate.

Examples of monomers (a1-2) include compounds such as 1-ethyl-cyclopentant-1-yl(meth)acrylate, 1-ethyl-cyclohexan-1-yl(meth)acrylate, 1-ethyl-cyclohept-1-yl (meth)acrylate, 1-methyl-cyclopent-1-yl(meth)acrylate, and 1-isopropyl-cyclopent-1-yl(meth)acrylate.

As the monomer (a1-2), preferred are those represented by formula (a1-2-1), (a1-2-2), (a1-2-3), (a1-2-4), (a1-2-5), (a1-2-6), (a1-2-7), (a1-2-8), (a1-2-9), (a1-2-10), (a1-2-11) or (a1-2-12), more preferred are those represented by formula (a1-2-1), (a1-2-2) (a1-2-3), (a1-2-4), (a1-2-5), (a1-2-6), (a1-2-7), (a1-2-8), (a1-2-9) or (a1-2-10), still more preferred are those represented by formula (a1-2-3) or (a1-2-4), and further still more preferred are those represented by formula (a1-2-3).

(a1-2-1) 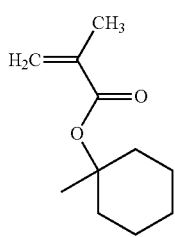

(a1-2-2) 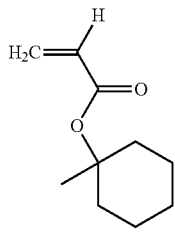

(a1-2-3) 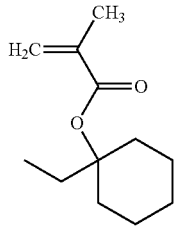

(a1-2-4) 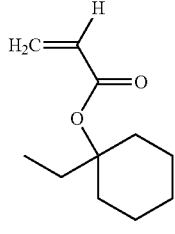

(a1-2-5) 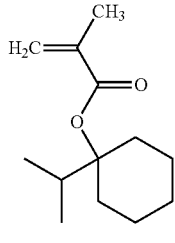

(a1-2-6) 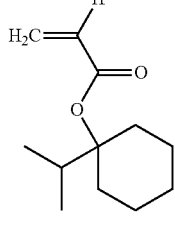

(a1-2-7) 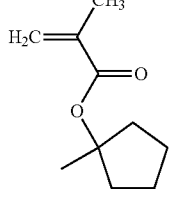

(a1-2-8) 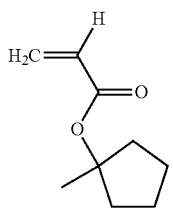

(a1-2-9) 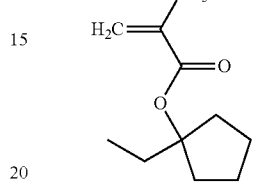

(a1-2-10) 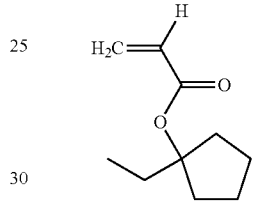

(a1-2-11) 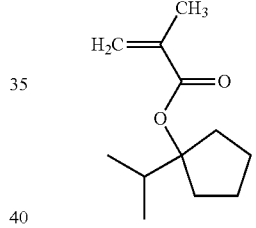

(a1-2-12) 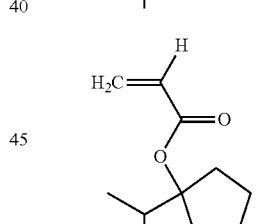

When the resin of the present invention contains a structural unit derived from the monomer (a1-1) and/or the monomer (a1-2), the content the structural unit is usually 10 to 95% by mole, preferably 15 to 90% by mole and more preferably 20 to 85% by mole based on 100% by mole of all the structural units of the resin of the present invention.

When the resin of the present invention contains a structural unit derived from a monomer having an amadantyl group and an acid labile group, preferably the monomer (a1-1), the content the structural unit is preferably 15% by mole or more, based on 100% by mole of all the structural units derived from a monomer having an acid labile group. With the increased content of the monomer having an amadantyl group and an acid labile group, the photoresist pattern with more improved resistance to dry etching can be obtained.

Another example of the monomer (a1) includes a compound represented by the formula (a-5).

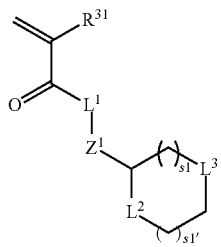
(a-5)

wherein $R^{31}$ represents a hydrogen atom, a halogen atom, or a C1-C6 alkyl group having a halogen group, $Z^1$ represents a single bond or *—$(CH_2)_{k1}$—CO-$L^4$- in which k1 represents an integer of 1 to 4 and * represents a binding site to $L^1$, $L^1$, $L^2$, $L^3$ and $L^4$ each independently represent an oxygen atom or a sulfur atom, s1 represents an integer of 1 to 3, and s1' represents an integer of 0 to 3.

In the formula (a-5), $R^{31}$ preferably represents a hydrogen atom, methyl group, or trifluoromethyl group.

$L^1$ represents an oxygen atom.

It is preferred that one of $L^2$ and $L^3$ represents an oxygen atom, while the other represents a sulfur atom.

s1 preferably represents 1. s1' represents an integer of 0 to 2.

$Z^1$ preferably represents a single bond or *—$CH_2$—CO—O— wherein * represents a binding site to $L^1$.

The compound represented by the formula (a-5) includes the following ones:

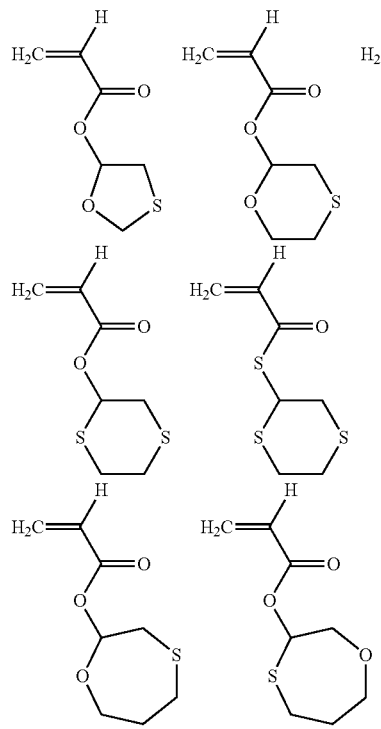

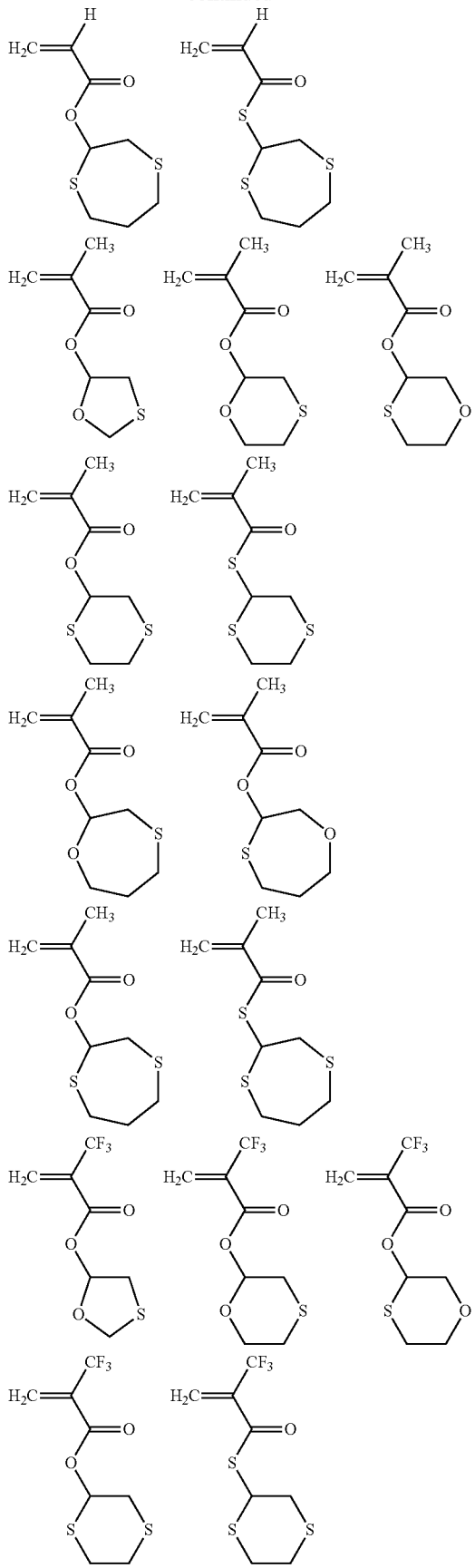

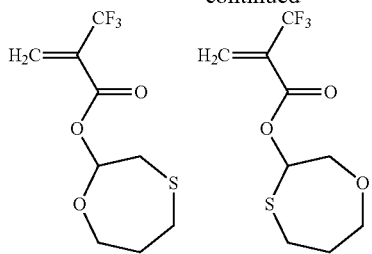

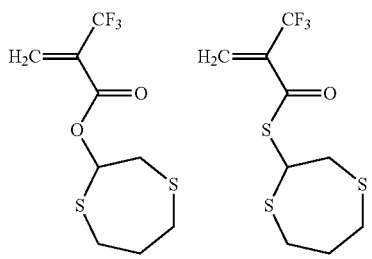

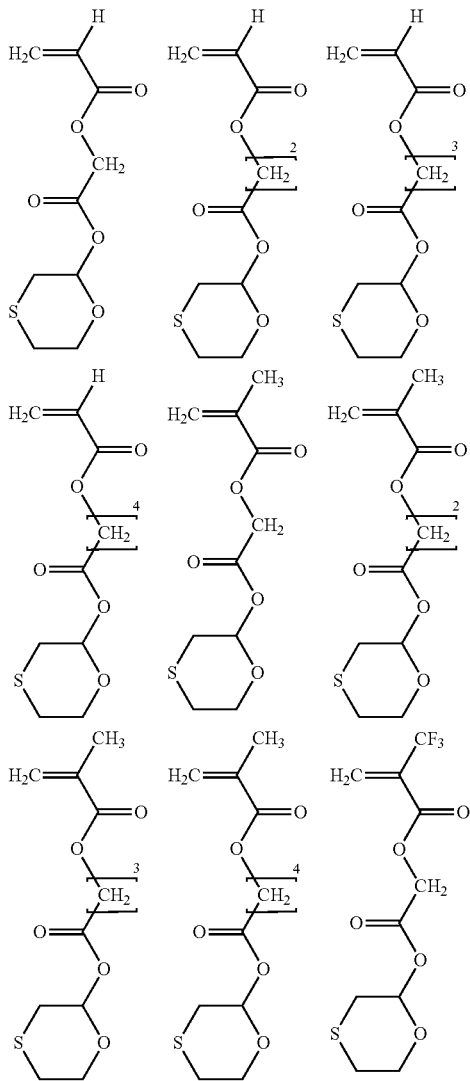

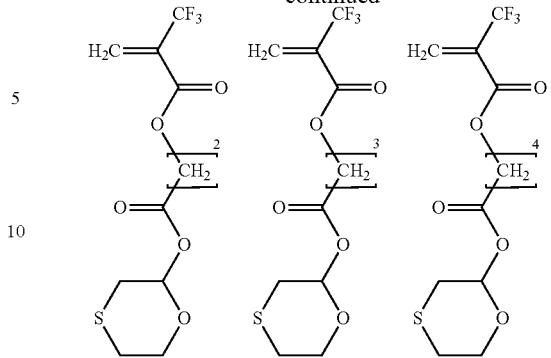

When the resin of the present invention contains a structural unit derived from compound represented by the formula (a-5), the content the structural unit is usually 1 to 50% by mole, preferably 3 to 45% by mole and more preferably 5 to 45% by mole based on 100% by mole of all the structural units of the resin of the present invention.

The resin of the present invention preferably contains the structural unit derived from a compound represented by formula (I) and a structural unit derived from a monomer having no acid-labile group. The resin can have two or more kinds of structural units derived from the monomers having no acid-labile group. The resin preferably contains the structural unit derived from a monomer having an acid-labile group and a structural unit derived from a monomer having no acid-labile group.

The monomer having no acid-labile group preferably contains a hydroxyl group or a lactone ring. When the resin contains the structural unit derived from the monomer having no acid-labile group and having a hydroxyl group or a lactone ring, a photoresist composition having good resolution and adhesiveness of photoresist to a substrate tends to be obtained.

When KrF excimer laser (wavelength: 248 nm) lithography system, or a high energy laser such as electron beam and extreme ultraviolet is used as an exposure system, the resin having no acid-labile group and having a hydroxyl group is preferable, and the resin having no acid-labile group and having a phenolic hydroxyl group, i.e. hydroxystyrene compounds, is more preferable. When ArF excimer laser (wavelength: 193 nm) is used as an exposure system, the resin having no acid-labile group and having a hydroxyladamantyl is preferable.

Examples of the monomer having no acid-labile group and having a phenolic hydroxyl groups include one having a phenolic hydroxyl group, represented by the formula (a2-0):

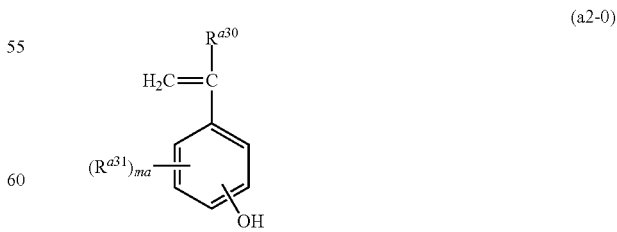

(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propynoyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The compound represented by formula (a2-0) includes p-hydroxystyrene and m-hydroxystylene.

Such resin having a phenolic hydroxyl group can be produced, for example, by radical-polymerizing acetoxystylene and other compounds, followed by deacetylation with a basic compound. The compounds having a phenolic hydroxyl group include compounds mentioned in JP2010-204634A, preferably those represented by the formulae (a2-0-1) and (a2-0-2). For production of the resin, the compound having a phenolic hydroxyl group protected by a suitable protecting group is used.

Examples of the monomer having no acid-labile group and having a hydroxyladamantyl group include one represented by the formula (a2-1):

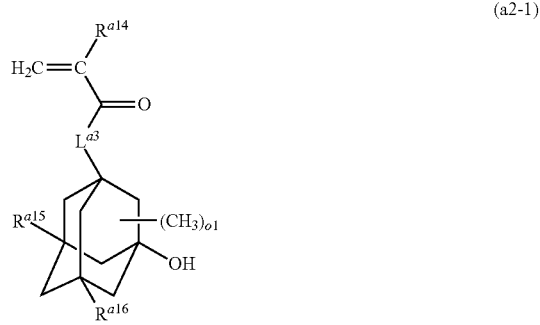

(a2-1)

wherein $R^{a14}$ represents a hydrogen atom, a methyl group or a hydroxyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

The compounds represented by formula (a2-1) include compounds mentioned in JP2010-204646A.

Preferred examples of the compound represented by the formula (a2-1) include those represented by formulae (a2-1-1) to (a2-1-6).

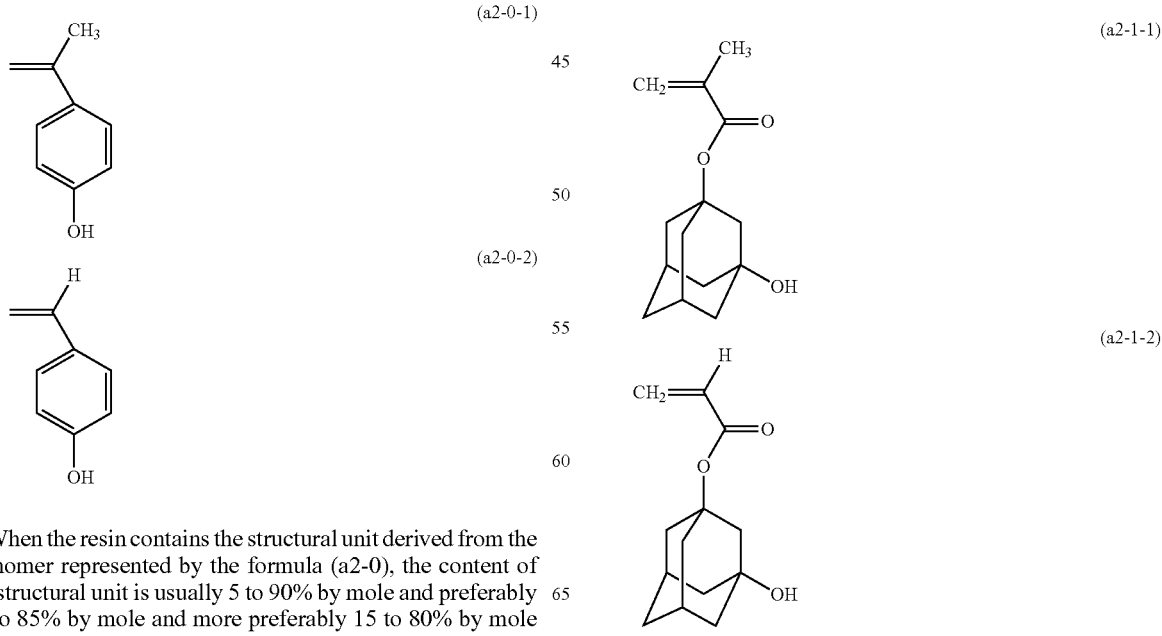

When the resin contains the structural unit derived from the monomer represented by the formula (a2-0), the content of the structural unit is usually 5 to 90% by mole and preferably 10 to 85% by mole and more preferably 15 to 80% by mole based on total molar of all the structural units of the resin.

-continued

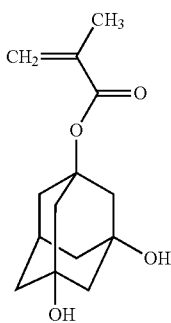
(a2-1-3)

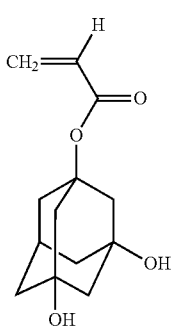
(a2-1-4)

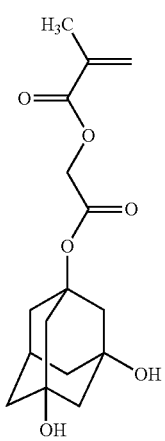
(a2-1-5)

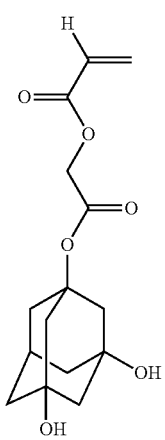
(a2-1-6)

Among them, more preferred are the monomer represented by formulae (a2-1-1), (a2-1-2), (a2-1-3) and (a2-1-4), still more preferred are the monomer represented by formulae (a2-1-1) and (a2-1-3).

When the resin of the present invention contains the structural unit derived from the monomer represented by the formula (a2-1) the content of the structural unit represented by the formula (a2-1) is usually 1 to 45% by mole based on total molar of all the structural units of the resin, and preferably 1 to 40% by mole, and more preferably 3 to 35% by mole, and especially preferably 3 to 20% by mole.

When the monomer having no acid-labile group has lactone ring, examples of the lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of monomers having no acid-labile group but having a lactone ring include those represented by the formulae (a3-1), (a3-2) and (a3-3):

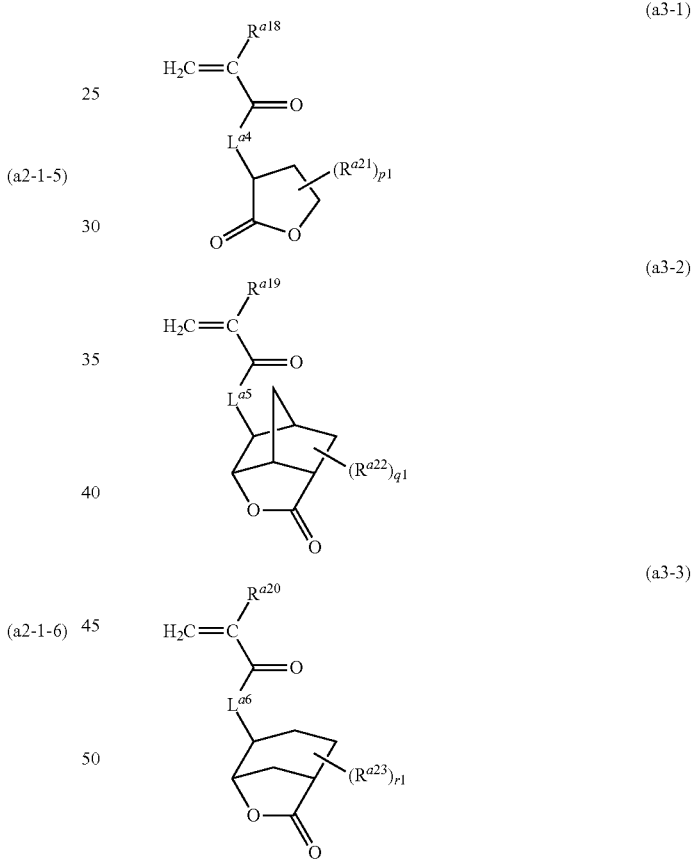

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group,
$R^{a21}$ represents a C1-C4 alkyl group, and $R^{a23}$ are independently in each occurrence a carboxyl group, a cyano group or a C1-C4 alkyl group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that g1 and r1 independently each represent an integer of 0 to 2, and it is more preferred that g1 and r1 independently each represent 0 or 1.

Examples of the monomer having no acid-labile group and a lactone ring include those mentioned in JP2010-204646A.

Preferred monomers having a lactone ring are those represented by the formulae (a3-1-1) to (a3-1-4), the formulae (a3-2-1) to (a3-2-4) and the formulae (a3-3-1) to (a3-3-4), more preferred are those represented by the formulae (a3-1-1), (a3-1-2) (a3-2-3) and (a3-2-4), and still more preferred are those represented by the formulae (a3-1-1) and (a3-2-3).

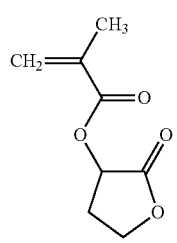
(a3-1-1)

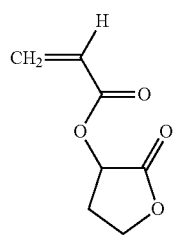
(a3-1-2)

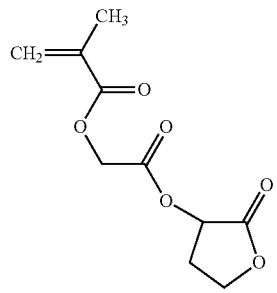
(a3-1-3)

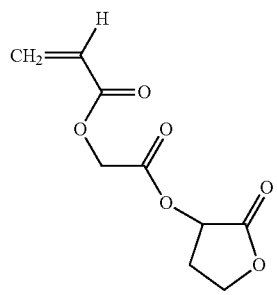
(a3-1-4)

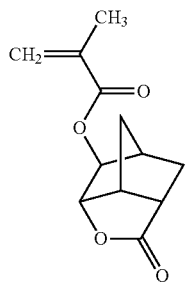
(a3-2-1)

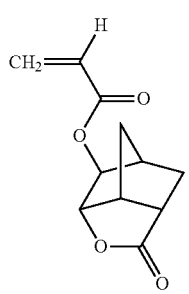
(a3-2-2)

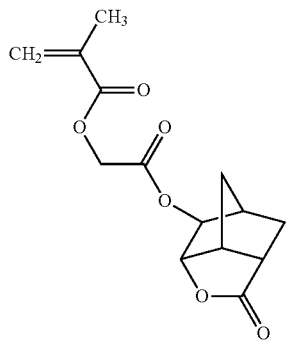
(a3-2-3)

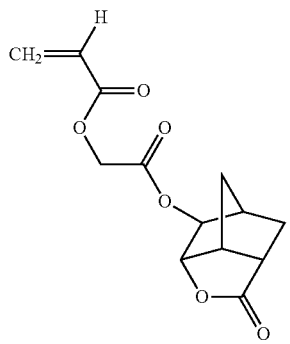
(a3-2-4)

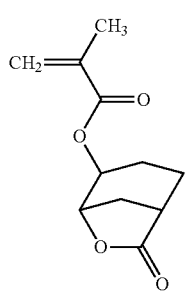
(a3-3-1)

(a3-3-2)

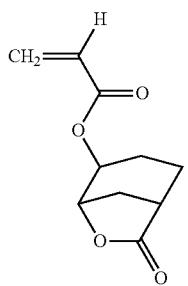

(a3-3-3)

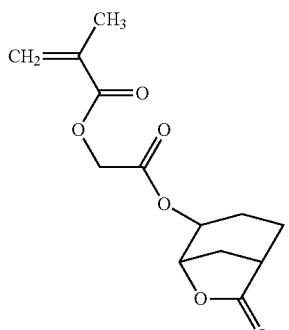

(a3-3-4)

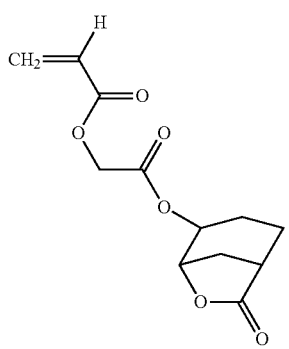

When the resin of the present invention contains the structural unit derived from the monomer having no acid-labile group but having a lactone ring, the content thereof is preferably 5 to 70% by mole based on total molar of all the structural units of the resin, and more preferably 10 to 65% by mole and more preferably 10 to 60% by mole.

When the resin of the present invention contains the structural unit derived from a monomer having an acid-labile group and the structural unit derived from a monomer having no acid-labile group, the content of the structural unit derived from a monomer having no acid-labile group is usually 10 to 80% by mole and preferably 20 to 60% by mole based on total molar of all the structural units of the resin. When the resin has these structural units in the above-mentioned proportion, the photoresist pattern obtained from the photoresist composition of the present invention can have more improved resistance to dry-etching.

The resin of the present invention may contain the structural unit derived from a known compound other than the monomers mentioned above. Such known compounds include a monomer having no acid-labile group but having a fluorine atom. The monomer having no acid-labile group but having a fluorine atom includes a compound represented by formula (a4-1);

(a4-1)

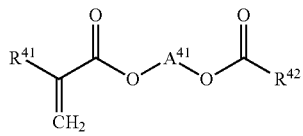

wherein $R^{41}$ represents a hydrogen atom or a methyl group, $A^{41}$ represents a moiety represented by formula (a-4-g1):

(a4-g1)

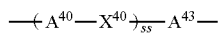

in which ss represents an integer of 0 to 2, $A^{40}$ and $A^{43}$ respectively represent a C1-C5 aliphatic hydrocarbon group which may have a substituent $X^{40}$ represents —O—, —CO—, —CO—O—, or —O—CO—, and $R^{42}$ represents a C1-C18 fluorine-containing aliphatic hydrocarbon group in which a methylene group may be replaced by —O— or —CO—.

Examples of $A^{40}$ and $A^{43}$ typically include a C1-C5 alkanediyl group which may be a linear chain or branched chain. Specific examples of them include a methylene group, an ethylene group, a propanediyl group, a butanediyl group, or a pentanediyl group. Hydrogen atoms of such alkanediyl group may be replaced by substituents such as a hydroxyl group or a C1-C6 alkoxy group.

$X^{40}$ represents —O—, —CO—, —CO—O—, or —O—CO—.

The moiety represented by formula (a4-g1) includes those having an oxygen atom as follow:

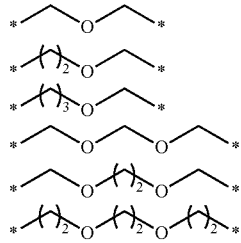

wherein * represents a binding site.

The moiety represented by formula (a4-g1) includes those having a carbonyl group as follow:

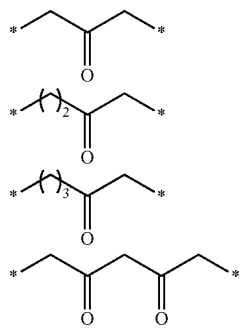

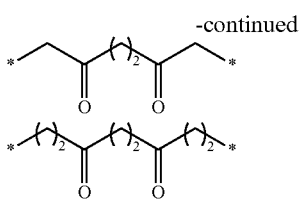

wherein * represents a binding site.

The moiety represented by formula (a4-g1) includes those having a carbonyloxy group as follow:

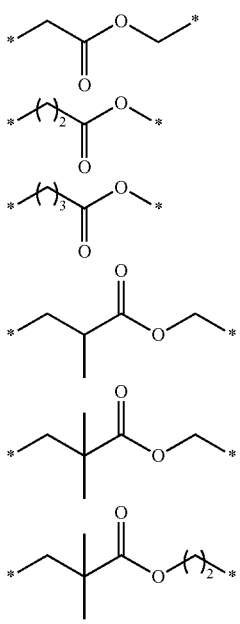

wherein * represents a binding site.

The moiety represented by formula (a4-g1) includes those having an oxycarbonyl group as follow:

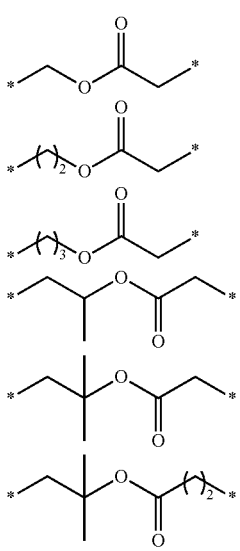

wherein * represents a binding site.

$A^{41}$ represents preferably aliphatic hydrocarbon groups, more preferably C1-C4 alkanediyl groups, and still more ethylene group. The fluorine-containing aliphatic hydrocarbon group represented by $R^{42}$ may be chain or cyclic, or one having both chain and cyclic.

The fluorine-containing aliphatic hydrocarbon group is preferably a fluorine-containing saturated aliphatic hydrocarbon group, which may have a carbon-carbon double bond.

The aliphatic hydrocarbon group is preferably a fluorine-containing saturated aliphatic hydrocarbon group, which may have a carbon-carbon double bond. The chain fluorine-containing aliphatic hydrocarbon group includes a trifluoromethyl group, a difluoromethyl group, a 1,1,1-trifluoroethyl group, a 1,1,1,2,2-pentafluoroethyl group, a 1,1,1,2,2-pentafluoropropyl group, a perfluorobutyl group, a 1,1,2,2,3,3,4,4-octafluorobutyl group, a perfluoropentyl group and a 1,1,1,2,2,3,3,4,4-nonafluorobutyl group. The cyclic fluorine-containing aliphatic hydrocarbon group may be monocyclic or polycyclic. The monocyclic fluorine-containing hydrocarbon group includes a fluorine-containing cycloalkyl group such as perfluorocyclohexyl group. The polycyclic fluorine-containing hydrocarbon group includes a perfluoroamadantyl group.

The fluorine-containing aliphatic hydrocarbon group in which a methylene group has been replaced by —O— or —CO— includes a compound represented by formula (a4-g2):

$$-A^{13}-X^{12a}-A^{14a} \qquad (a4-g2)$$

in which $A^{13}$ represents a C1-C15 divalent aliphatic hydrocarbon group which may have a fluorine atom, $X^{12a}$ represents a carbonyloxy group or an oxycarbonyl group, and $A^{14a}$ represents a C1-C15 divalent aliphatic hydrocarbon group which may have a fluorine atom, provided that $A^{13}$ and $A^{14a}$ have 16 or less of carbon atoms in total and one or both of $A^{13}$ and $A^{14a}$ have a fluorine atom.

The divalent aliphatic hydrocarbon group which may have a fluorine atom may be chain or cyclic, or one having both chain and cyclic.

Such divalent aliphatic hydrocarbon group is preferably divalent saturated aliphatic hydrocarbon group which may have a fluorine atom, although it may have a carbon-carbon double bond.

The chain divalent aliphatic hydrocarbon group which may have a fluorine atom includes a methylene group, a difluoromethylene group, an ethylene group, a perfluoroethylene group, a propanediyl group, a perfluoropropanediyl group, a butanediyl group, a perfluorobutanediyl group, a pentanediyl group or a perfluoropentanediyl group.

The divalent alicyclic hydrocarbon group may be monocyclic or polycyclic. The monocyclic hydrocarbon group includes a cycloalkyl group such as a cyclohexyl group, a perfluorocyclohexyl group. The polycyclic hydrocarbon group includes an amadantyl group, nobornyl group, or perfluoroamadantyl group.

In formula (a4-g2), $A^{13}$ and $A^{14a}$ have 15 or less of carbon atoms in total. $A^{13}$ has preferably 1 to 6 carbon atoms, more preferably 2 to 3 carbon atoms. $A^{14a}$ has preferably 5 to 12 carbon atoms, more preferably 6 to 10 carbon atoms.

$A^{14a}$ represents preferably C6-C12 alicyclic hydrocarbon group, more preferably a cyclohexyl group, a norbornyl group and an amadantyl group.

The moiety of formula (a4-g2) includes preferably those as follow.
The moiety of formula (a4-1) includes preferably those represented by formulae (a4-1-1) to (a4-1-22).
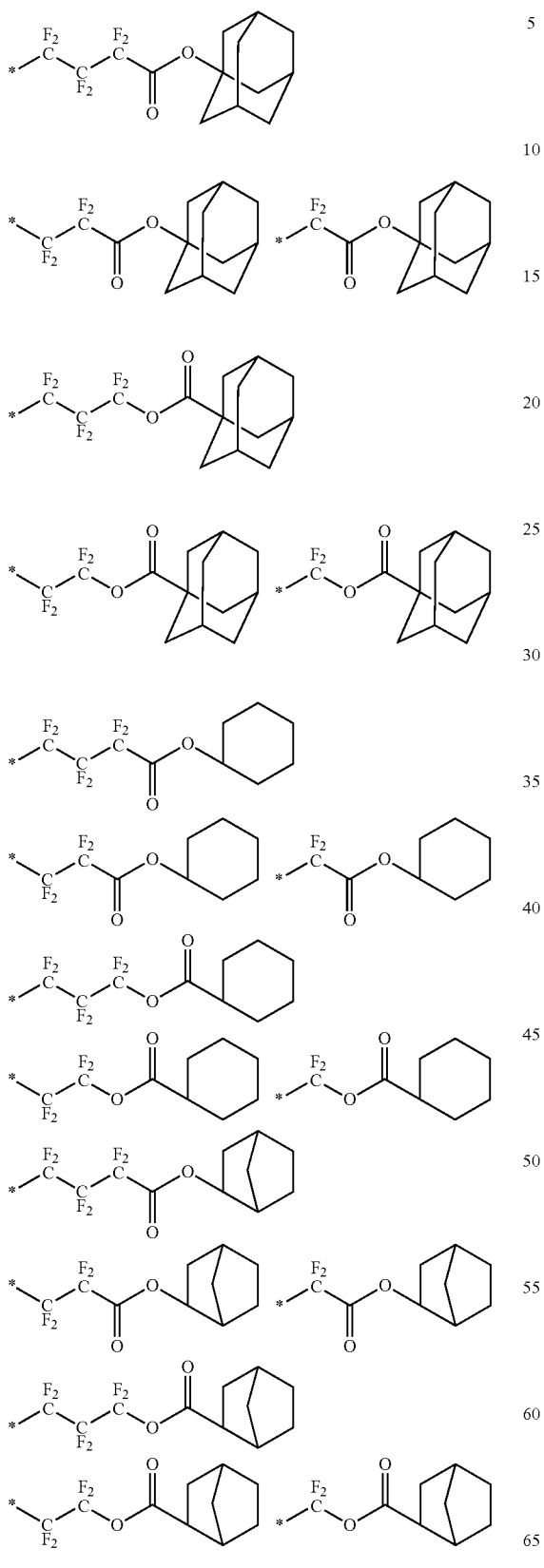
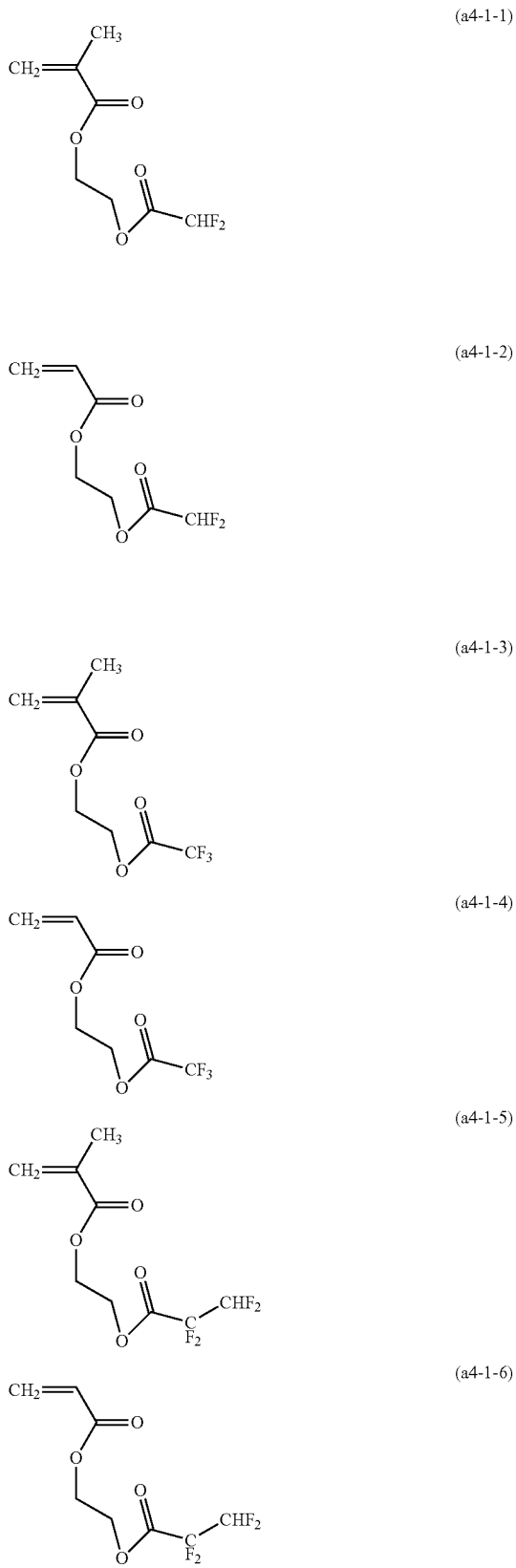

(a4-1-7) 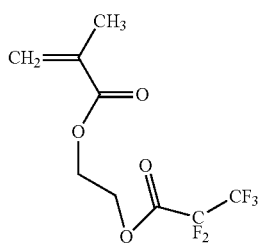
(a4-1-8) 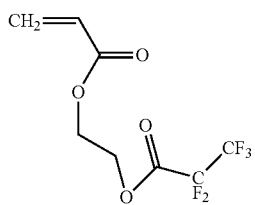
(a4-1-9) 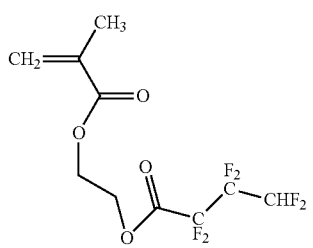
(a4-1-10) 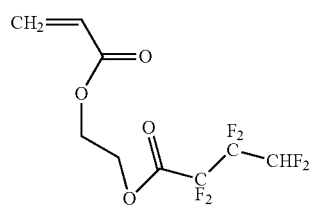
(a4-1-11) 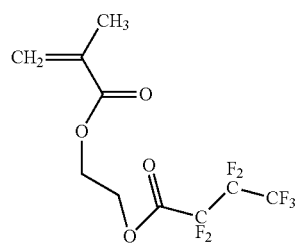
(a4-1-12) 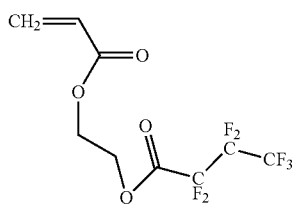
(a4-1-13) 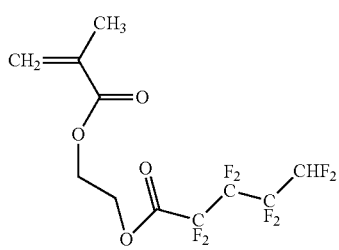
(a4-14) 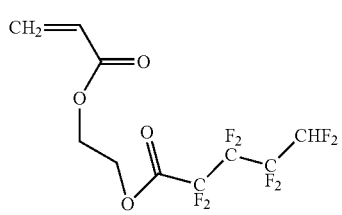
(a4-15) 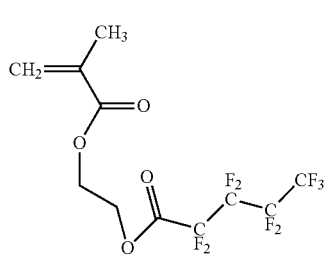
(a4-1-16) 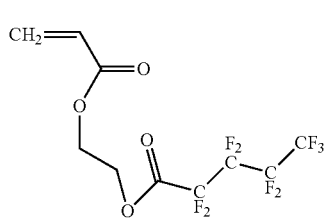
(a4-1-17) 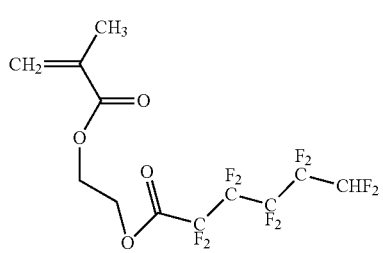
(a4-1-18) 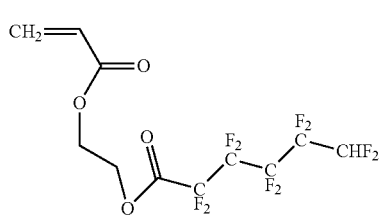
(a4-1-19) 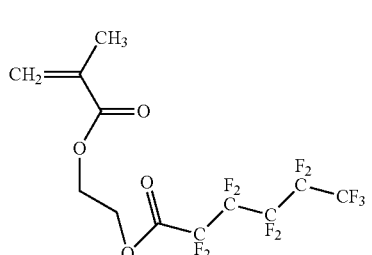
(a4-1-20) 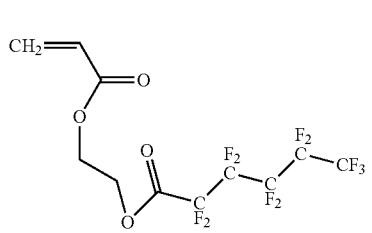

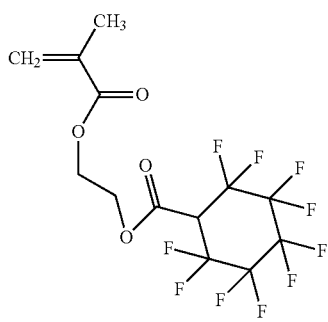
(a4-1-21)

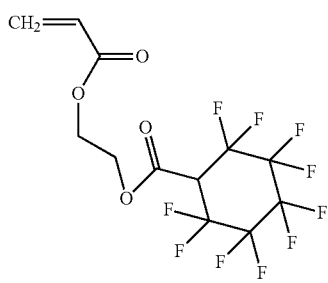
(a4-1-22)

Among these, preferred are the compounds represented by any one of formulae (a4-1-3), (a4-1-4), (a4-1-7), (a4-1-8), (a4-1-11), (a4-1-12), (a4-1-15), (a4-1-16), (a4-1-19), (a4-1-20), (a4-1-21) and (a4-1-22).

The resin of the present invention is preferably a copolymer which contains a structural unit derived from a compound represented by the formula (I), in addition to a structural unit derived from a monomer having an acid-labile group other than the above-mentioned compound, a structural unit derived from a monomer having no acid-labile group but having a hydroxyl group and/or a structural unit derived from a monomer having no acid-labile group but having a lactone ring.

The monomer having an acid-labile group is preferably the compound having an amadantyl group, e.g. the compound represented by the formula (a1-1) and the compound having a cyclohexyl group e.g. the compound represented by the formula (a1-2).

The monomer having no acid-labile group but having a hydroxyl group is preferably the compound having a hydroxyamadantyl group, e.g. the compound represented by the formula (a2-1). The monomer having no acid-labile group and having a lactone group is preferably the compound having γ-butyrolactone ring, e.g. the compound represented by the formula (a3-1) and the compound having a condensed ring formed from γ-butyrolactone ring and norbornene ring, e.g. the compound represented by the formula (a3-2).

In the resin of the present invention, the content of the structural unit derived from the compound represented by formula (I)/the structural unit derived from the monomer having an acid-labile group other than the compound represented by formula (I)/the structural unit derived from the monomer having no acid-labile group but having a hydroxyl group and/or lactone ring/the structural unit derived from other monomers is preferably (1-50)/(20-60)/(30-70)/(1-20), more preferably (3-40)/(25-55)/(35-65)/(2-15), still more preferably (5-30)/(25-50)/(35-65)/(3-10), on mole basis.

In the resin of the present invention, the content of the structural unit derived from the compound represented by formula (I)/the structural unit derived from the monomer having an acid-labile group other than the compound represented by formula (I)/the structural unit derived from the monomer having no acid-labile group but having a hydroxyl group and/or lactone ring is preferably (1-50)/(20-60)/(30-76), more preferably (3-40)/(25-55)/(35-65), still more preferably (5-30)/(25-50)/(35-65), on mole basis. The content of the structural unit derived from the compound represented by formula (I)/the structural unit derived from the monomer having an acid-labile group other than the compound represented by formula (I)/the structural unit derived from the monomer having no acid-labile group but having a hydroxyl group/the structural unit derived from the monomer having no acid-labile group but having a lactone ring is preferably (1-50)/(20-60)/(3-35)/(25-65), more preferably (3-40)/(25-55)/(4-30)/(30-65), still more preferably (5-30)/(25-50)/(5-25)/(35-60), on mole basis.

More preferred resin of the present invention is those having a set of structural units as follows:

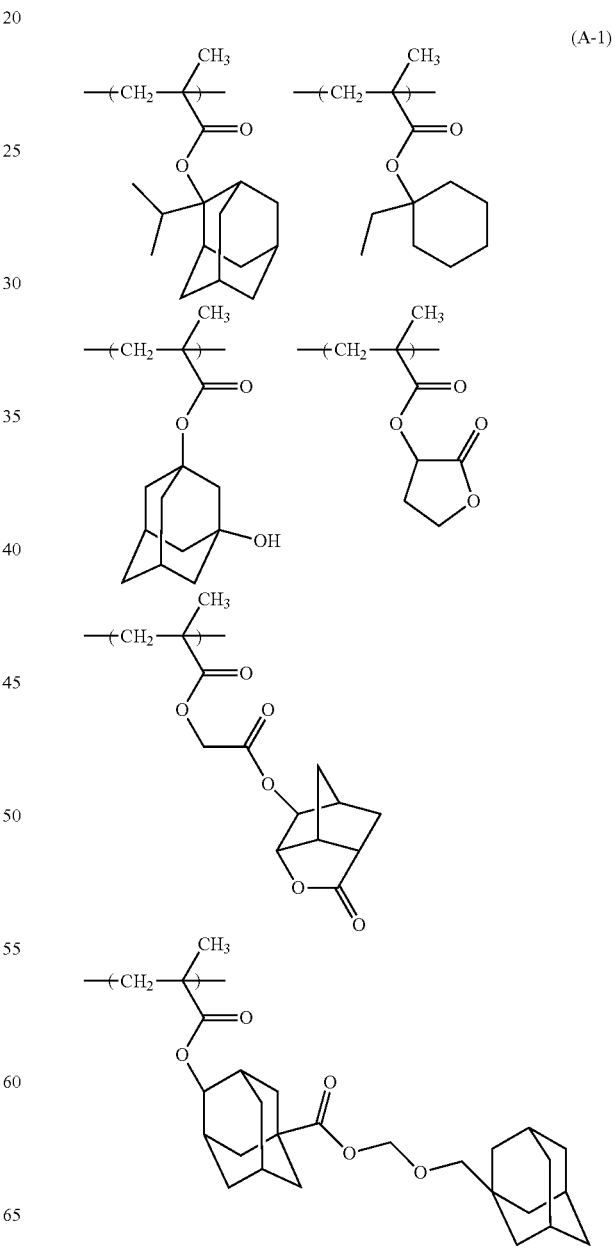
(A-1)

(A-2)
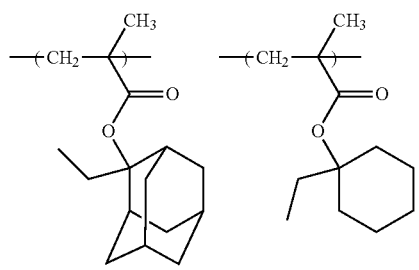
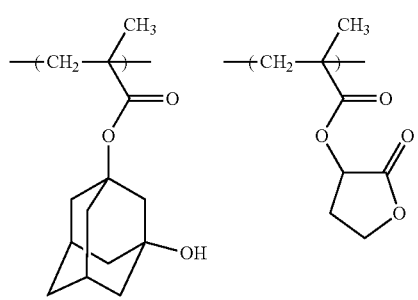
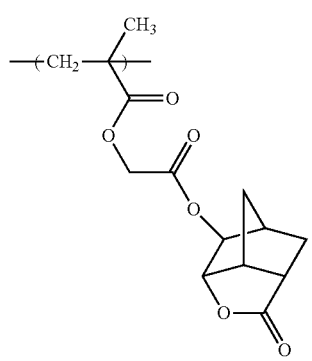
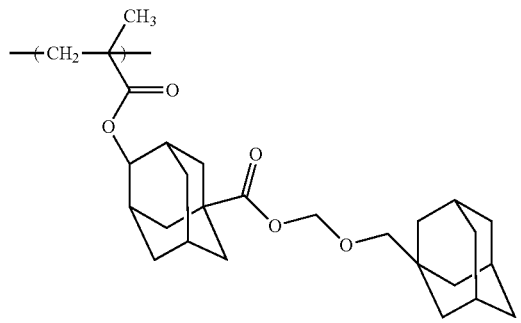
(A-3)
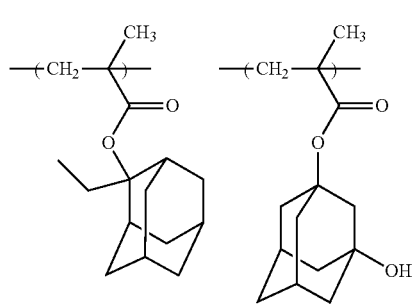
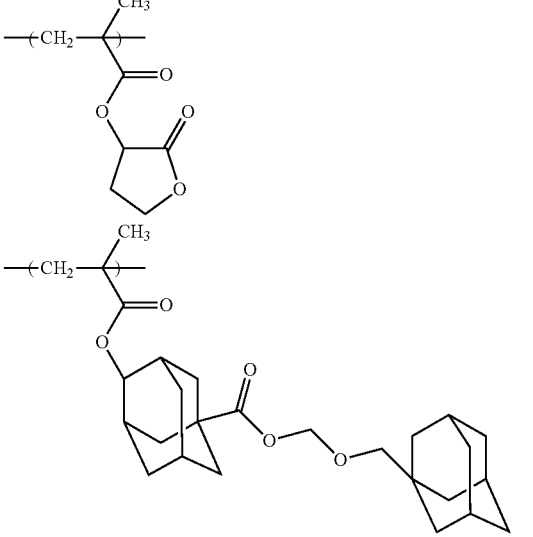
(A-4)
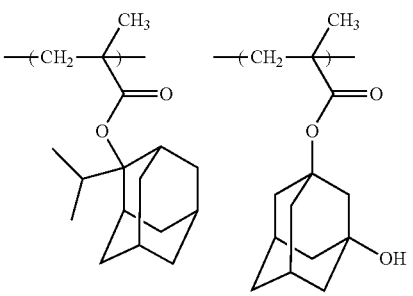
(A-5)
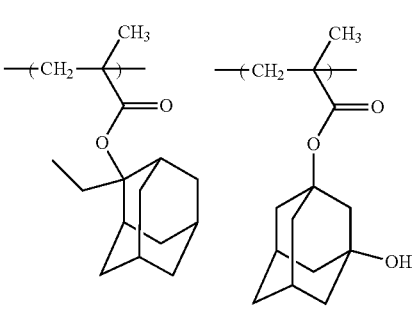

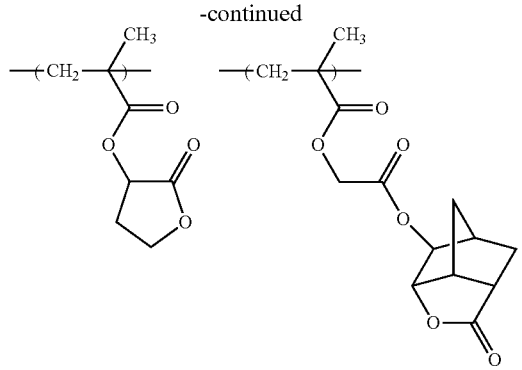
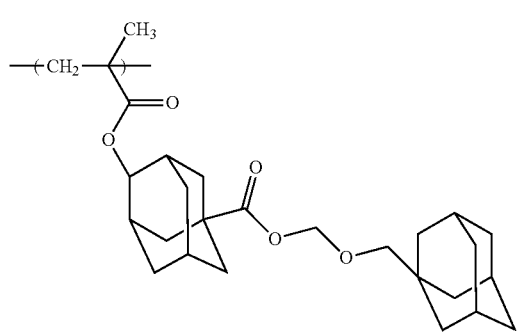
(A-6)
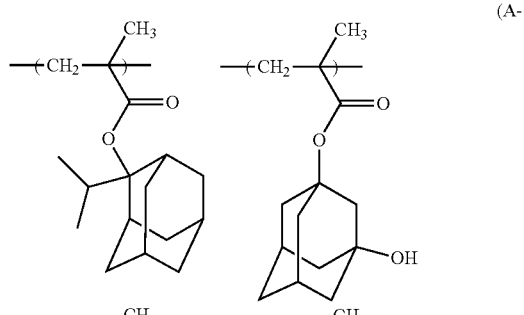
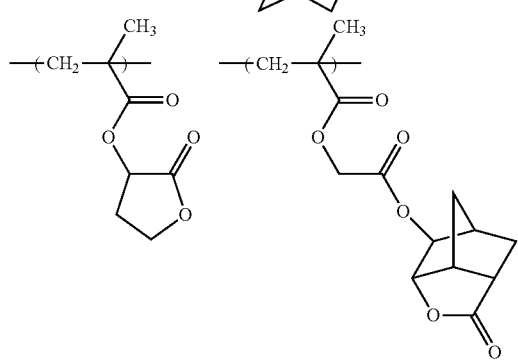
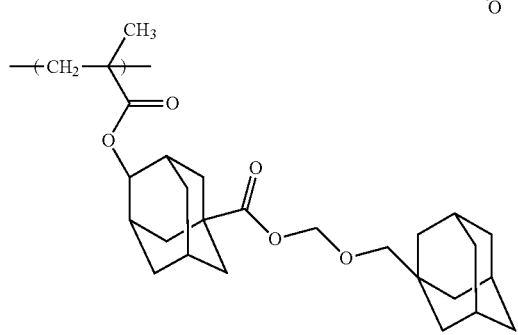
(A-7)
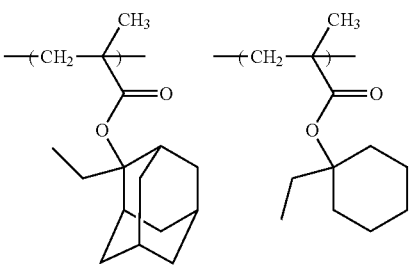
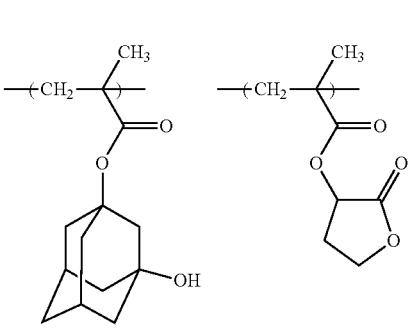
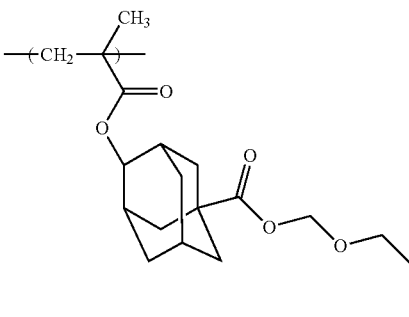
(A-8)
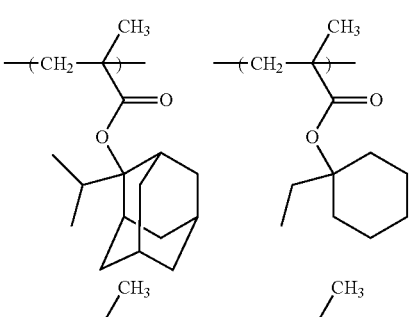
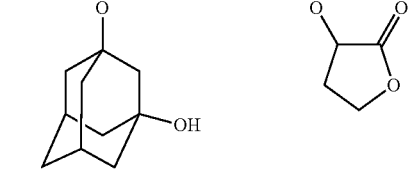

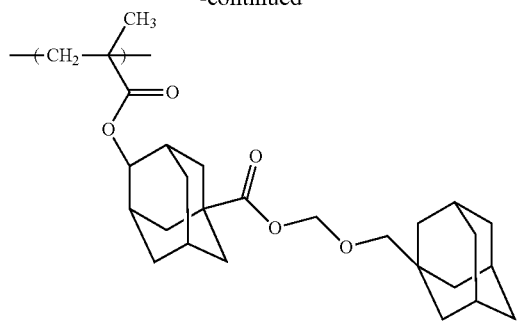
(A-9)
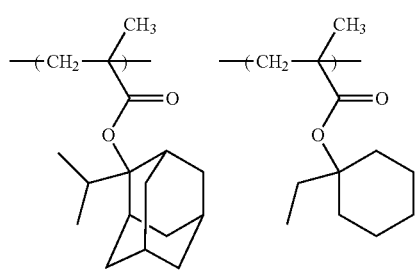
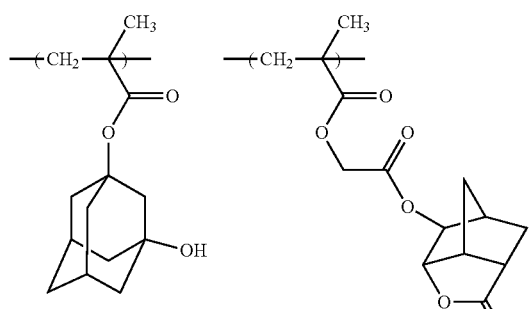
(A-10)
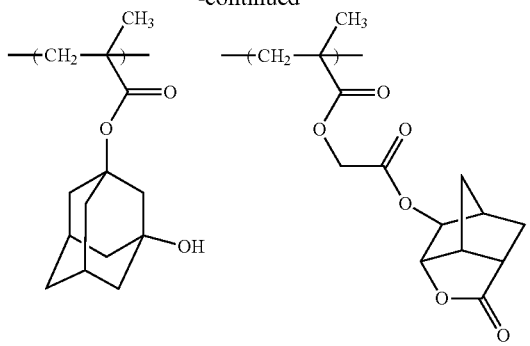
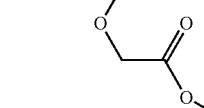
(A-11)
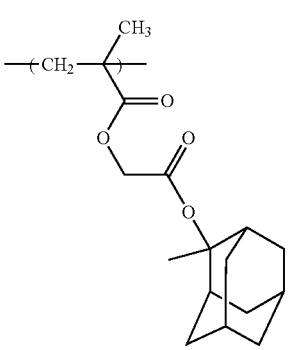
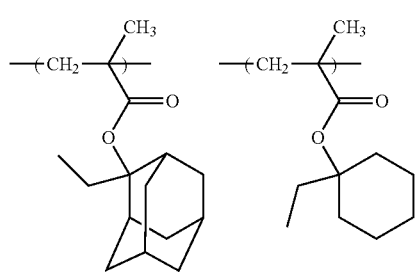

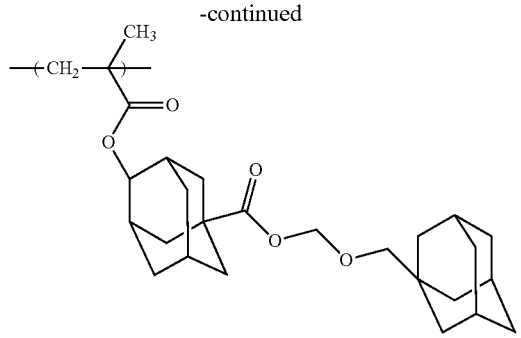
(A-12)
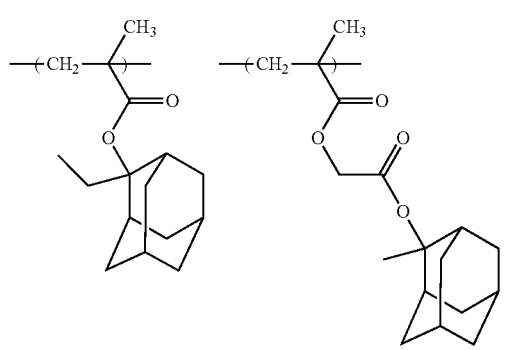
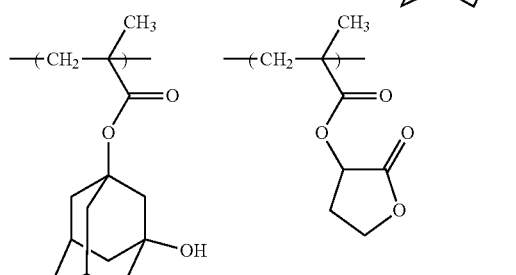
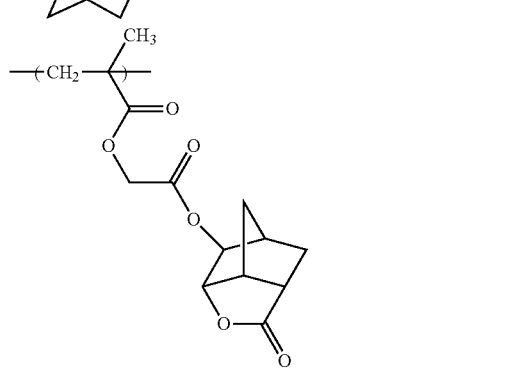
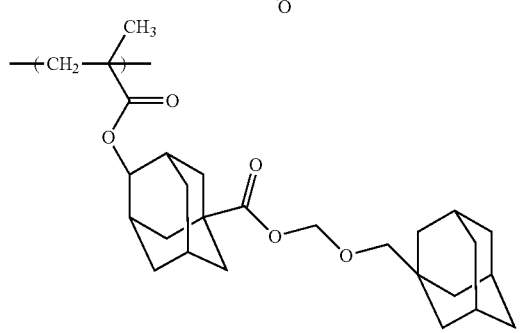
(A-13)
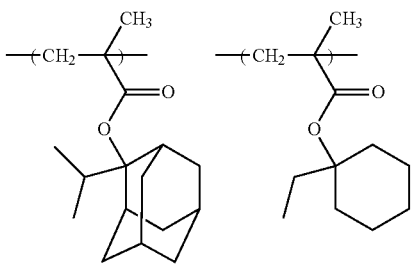
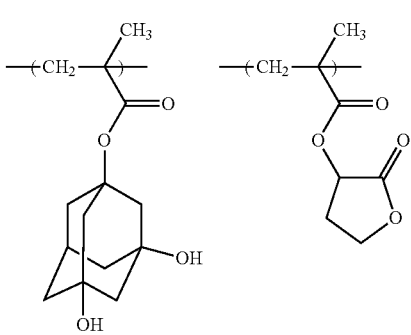
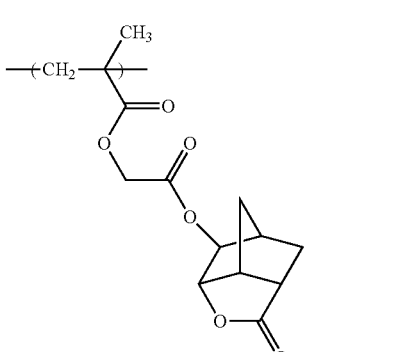
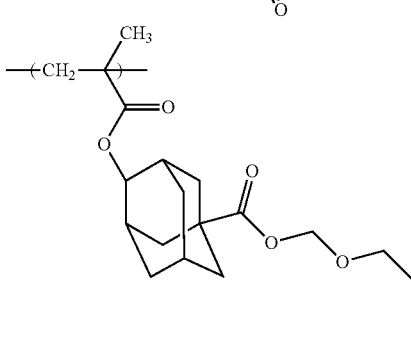
(A-14)
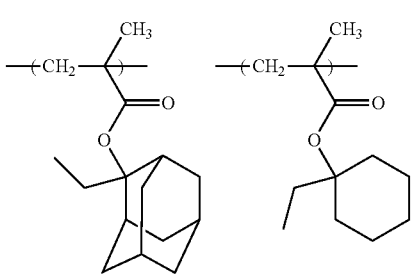

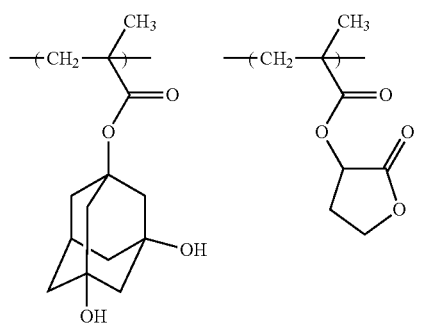
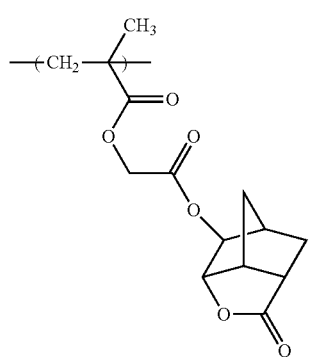
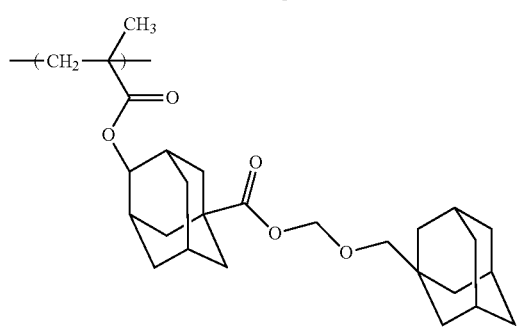
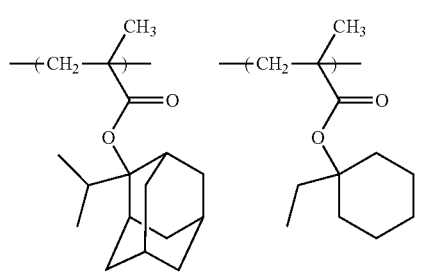
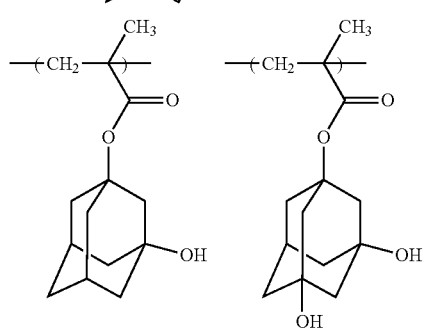
(A-15)
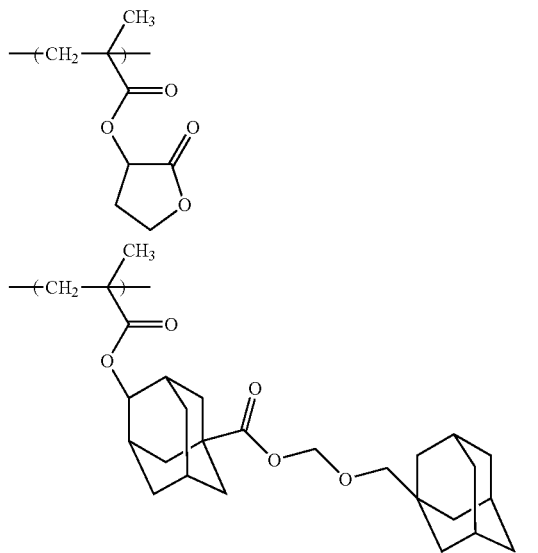
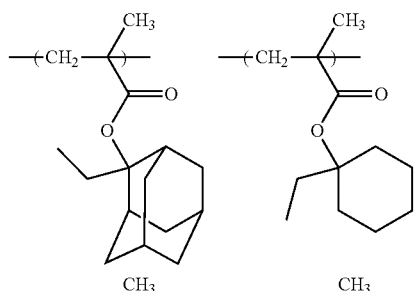
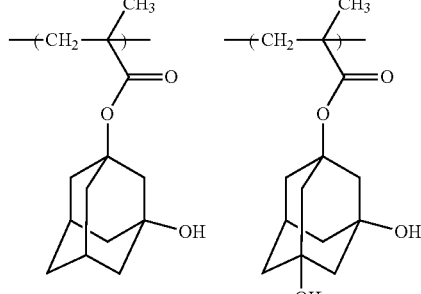
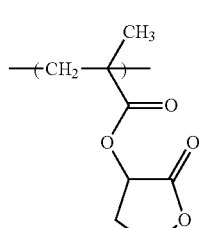
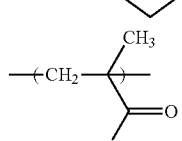
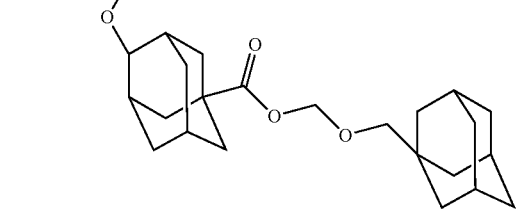
(A-16)

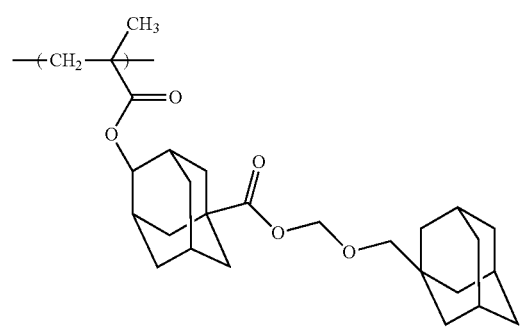
(A-17)
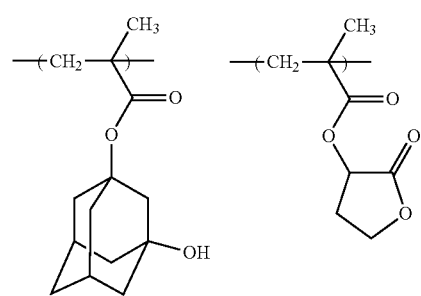
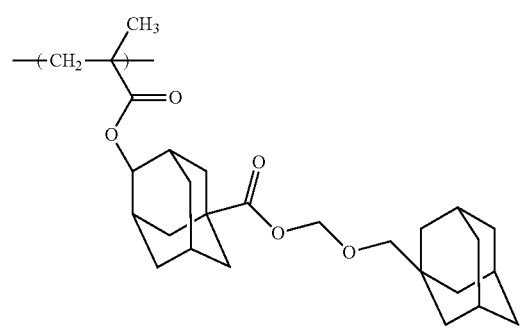
(A-18)
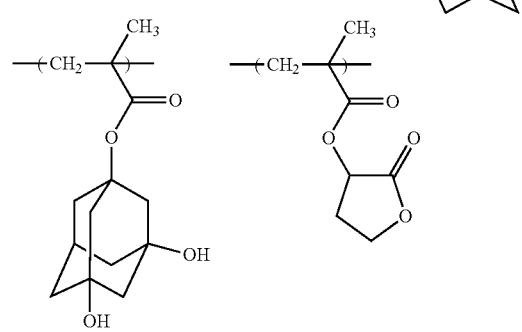
(A-19)
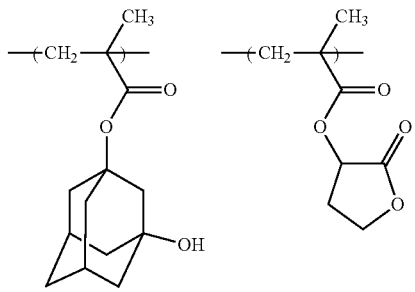
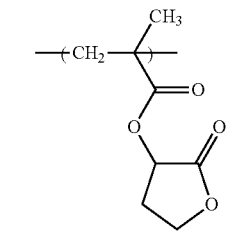
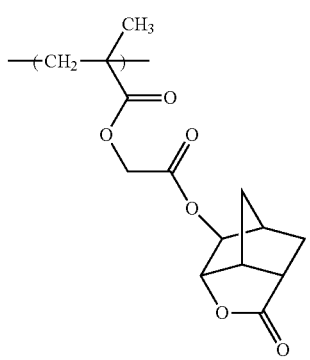
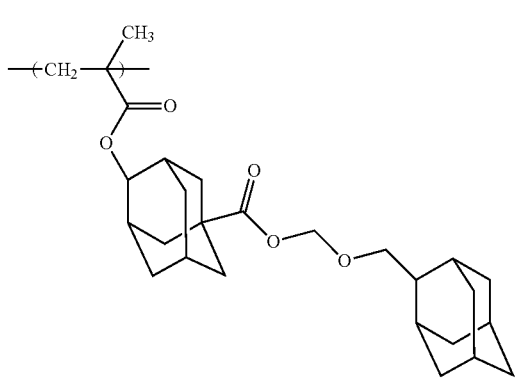
(A-20)
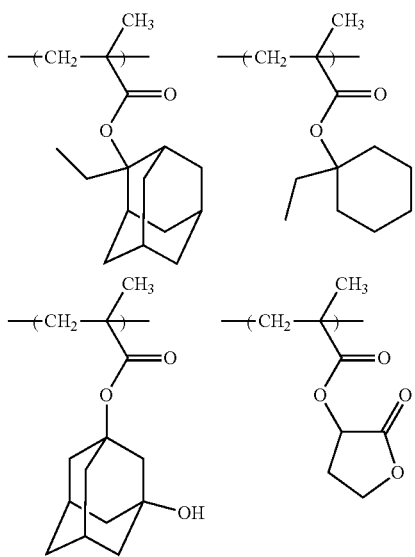

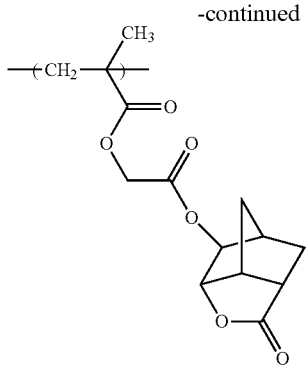
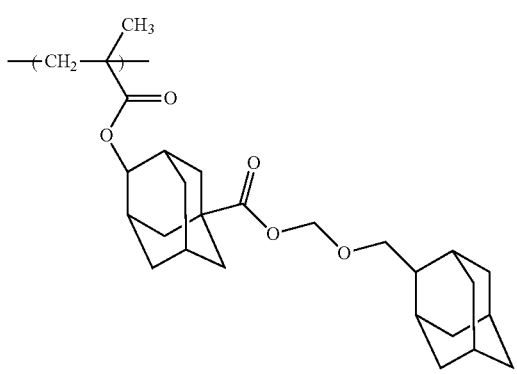
(A-21)
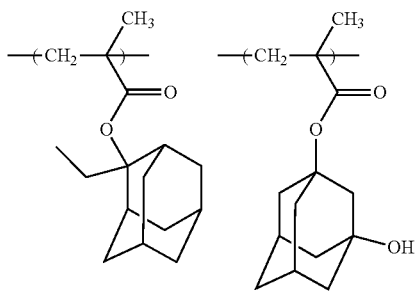
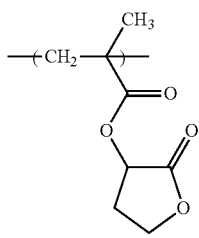
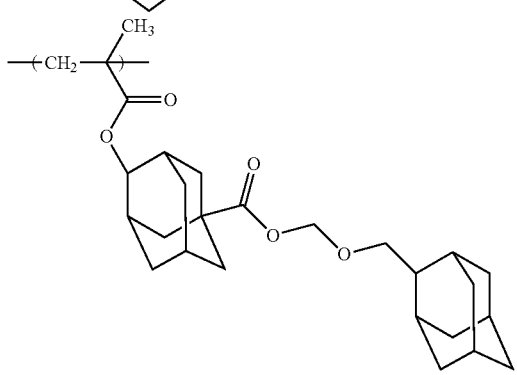
(A-22)
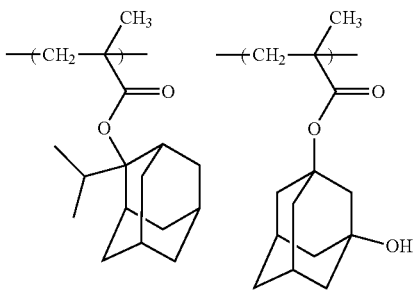
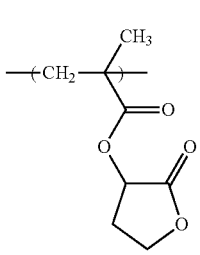
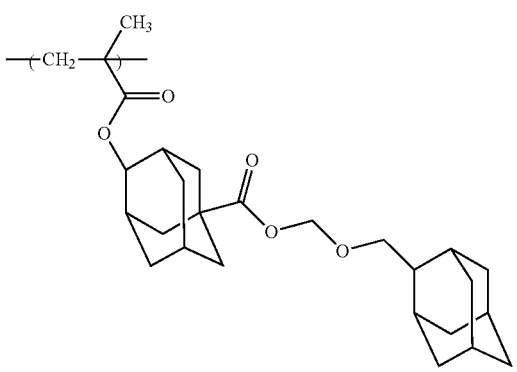
(A-23)
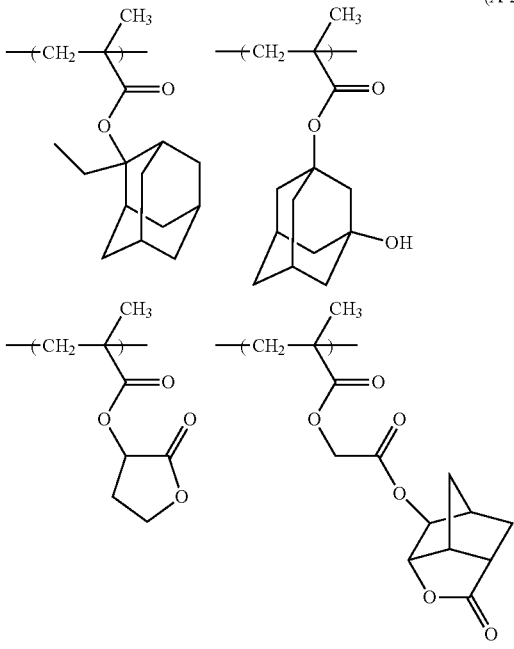

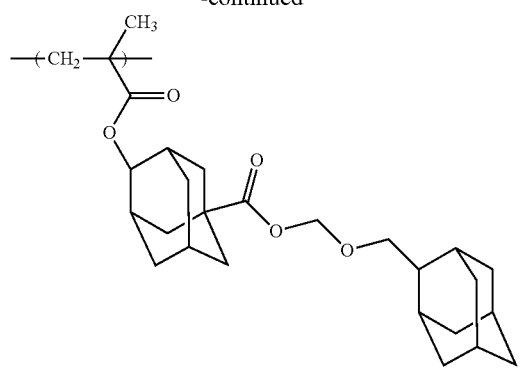
(A-24)
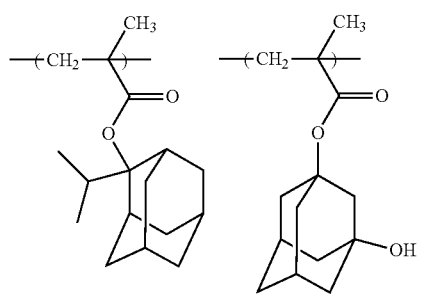
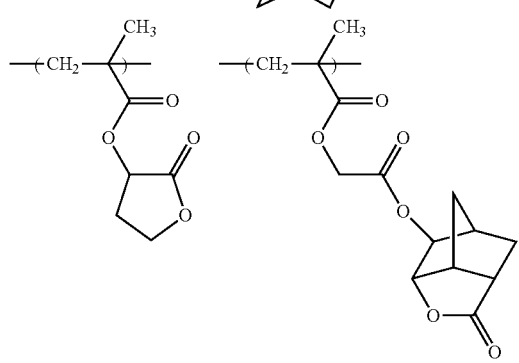
(A-25)
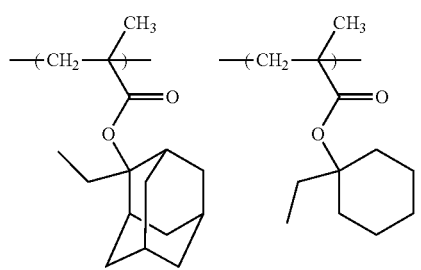
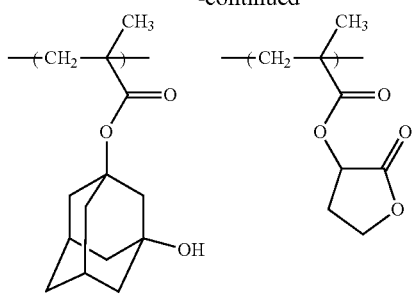
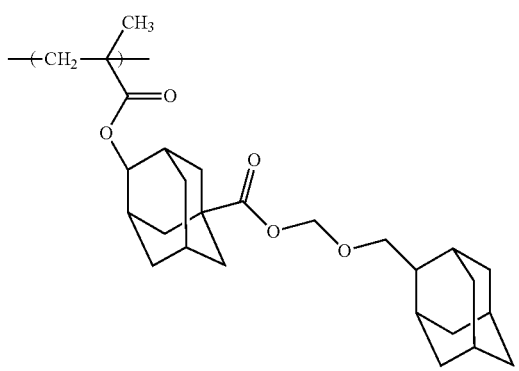
(A-26)
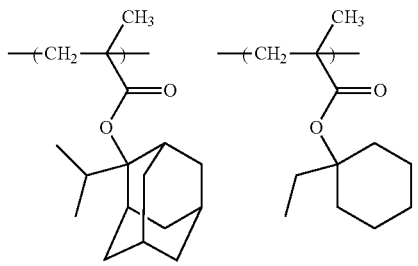
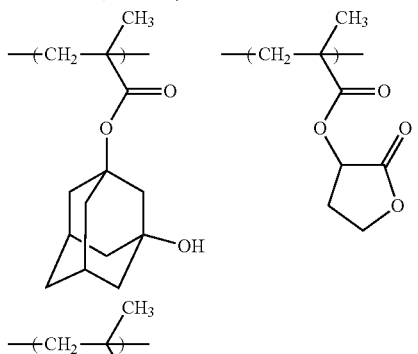
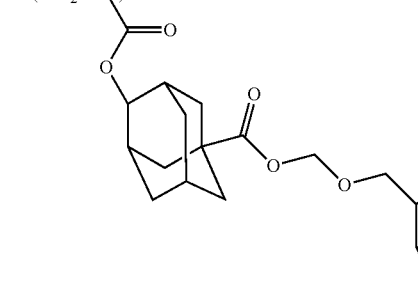

-continued
(A-27)
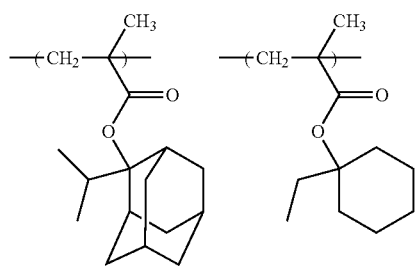
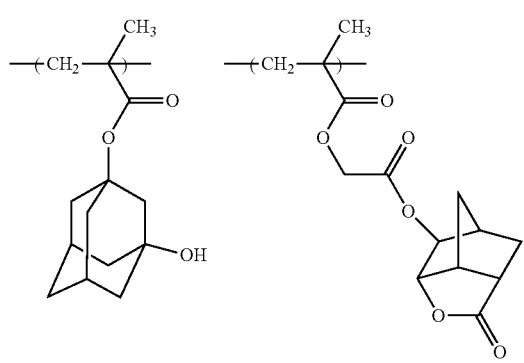
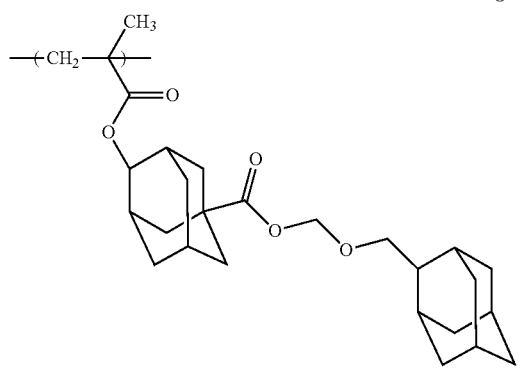
(A-28)
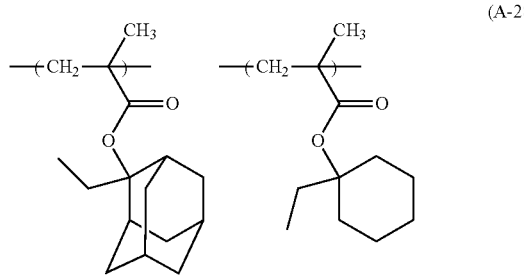
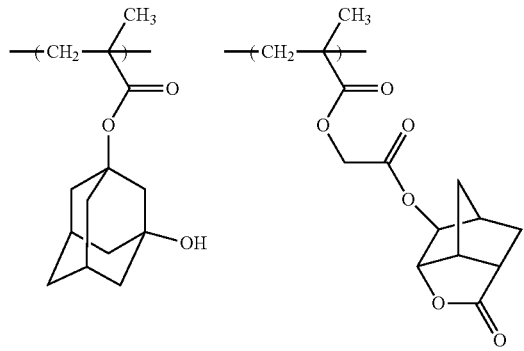
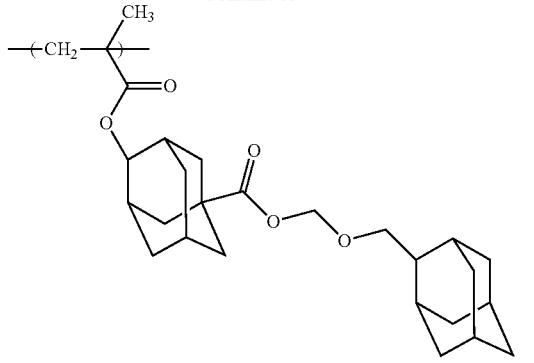
(A-29)
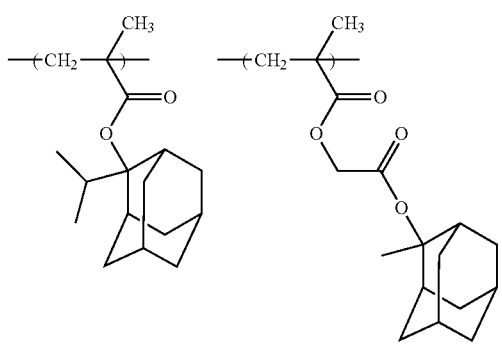
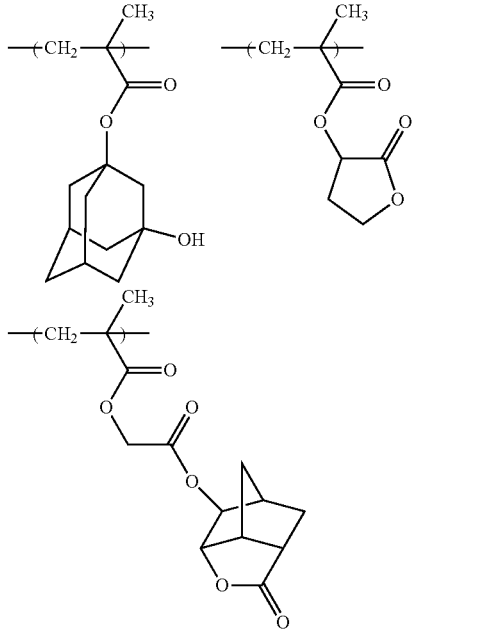
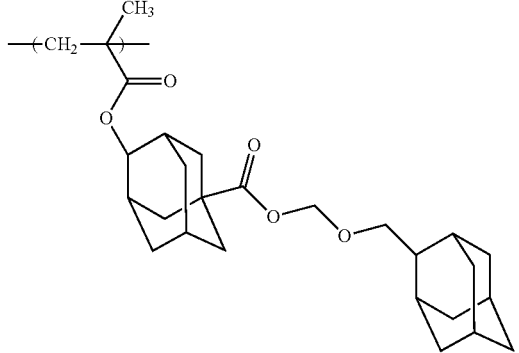

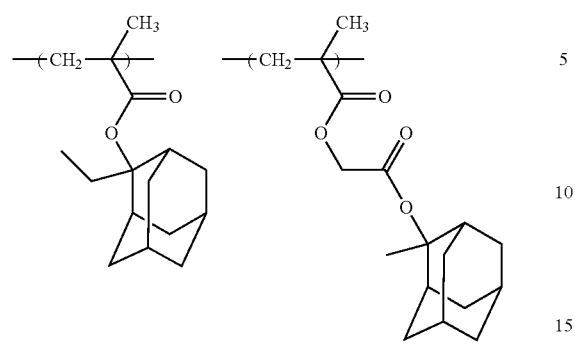
(A-30)
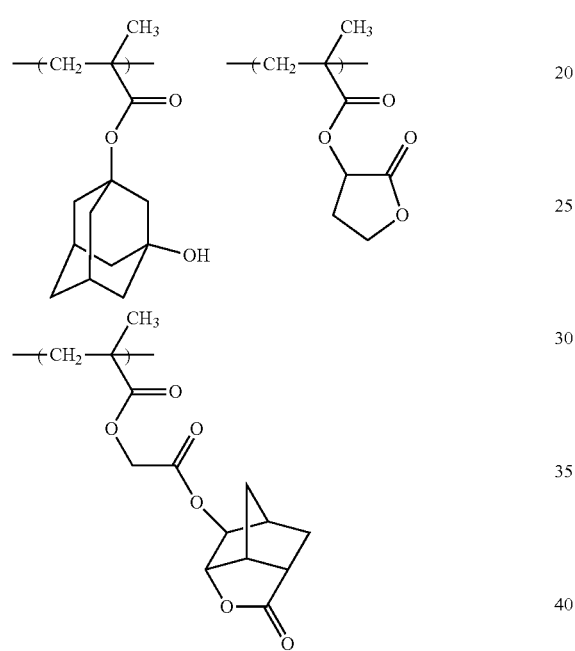
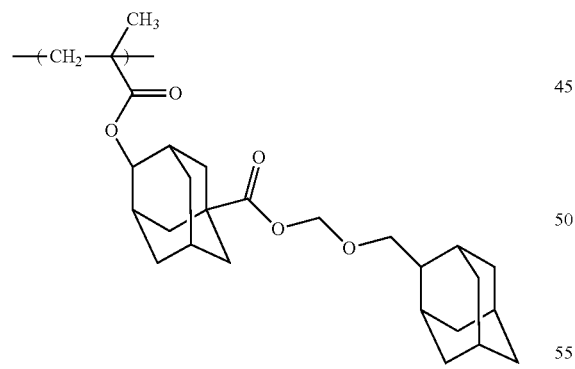
(A-31)
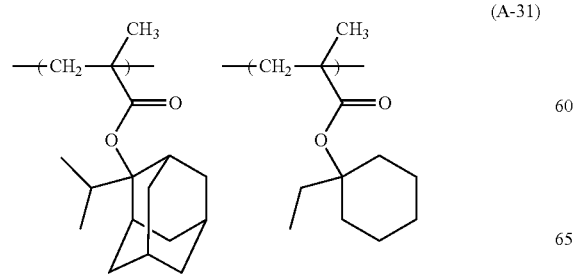
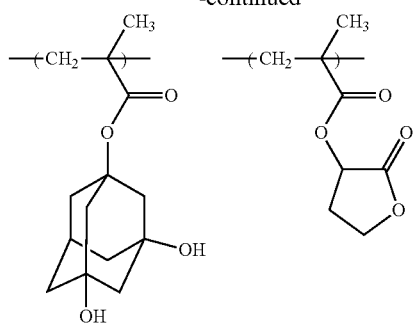
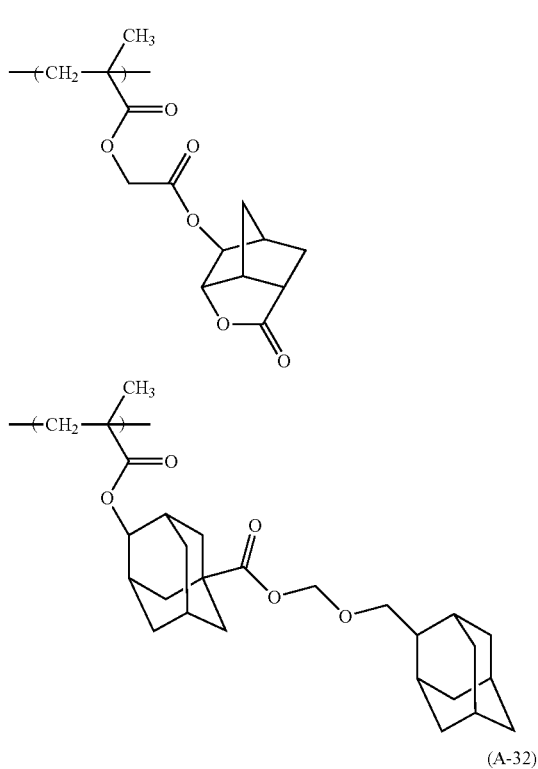
(A-32)
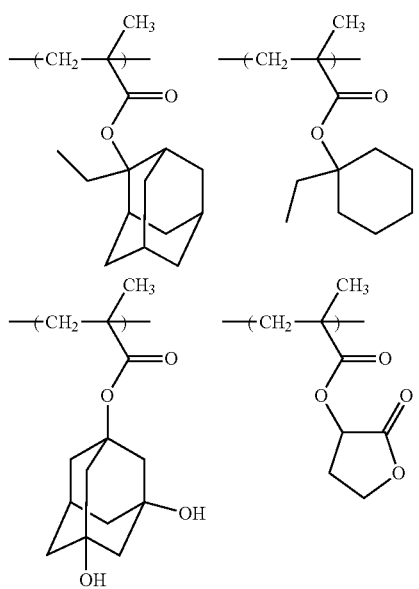

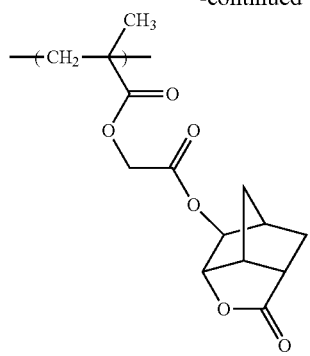
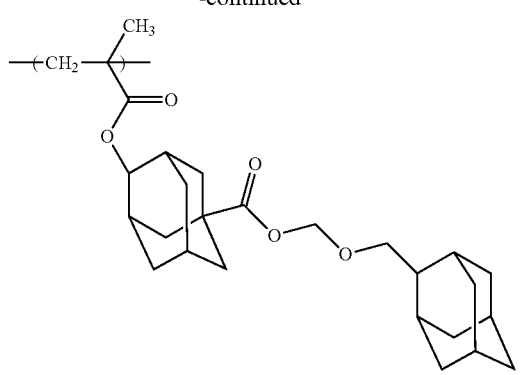
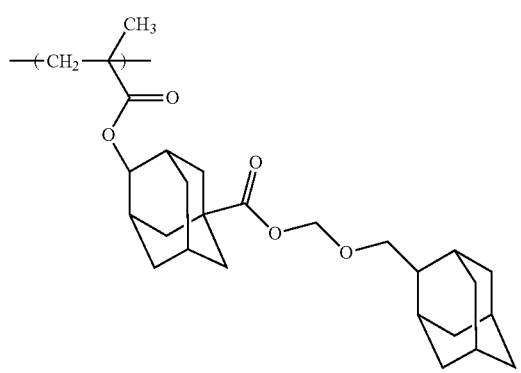
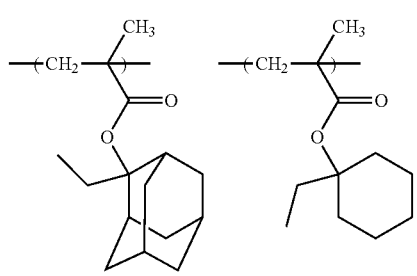
(A-33)
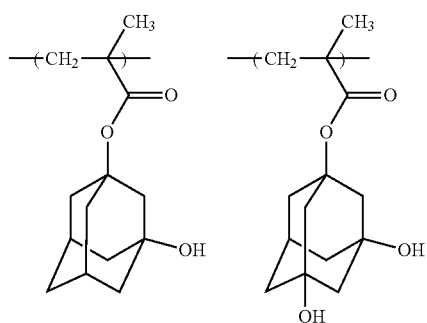
(A-34)
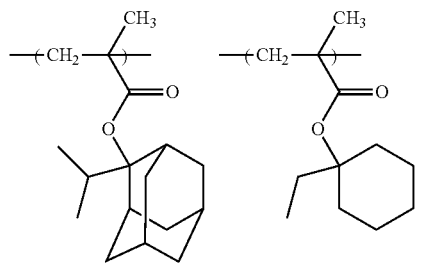
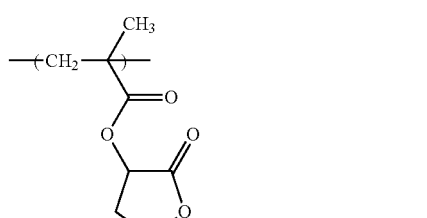
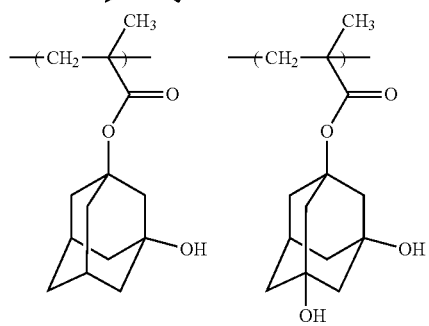
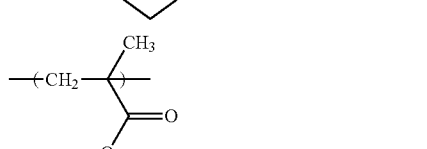
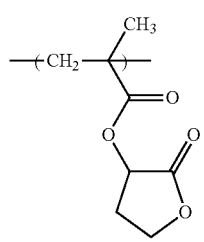
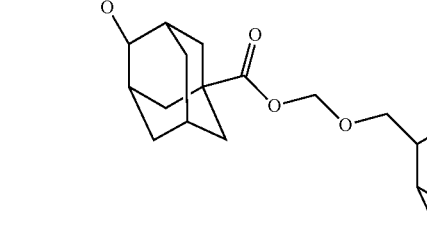
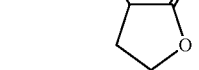

(A-35)
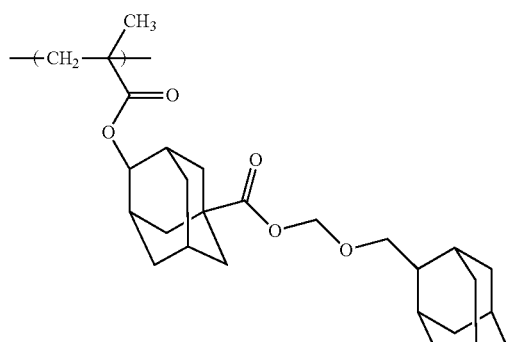
(A-36)
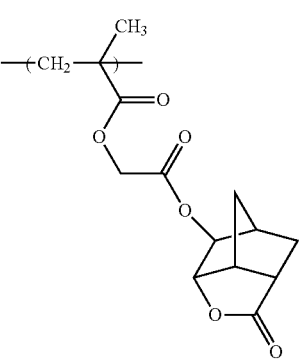
(A-37)
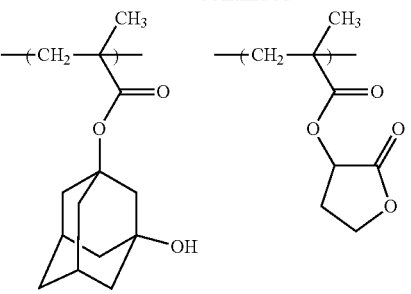
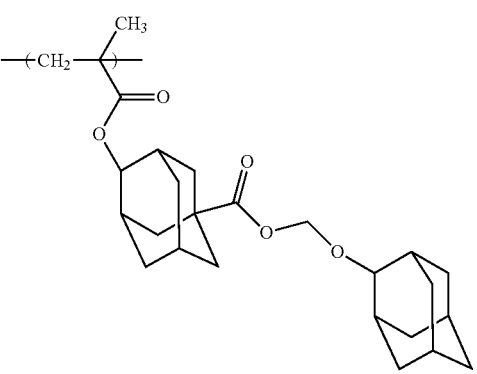
(A-38)
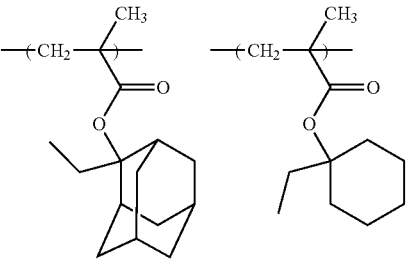
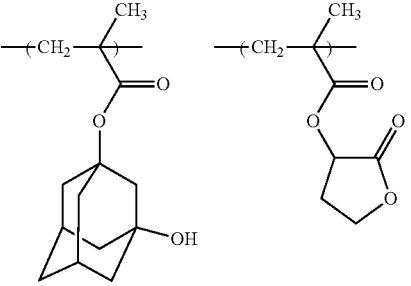

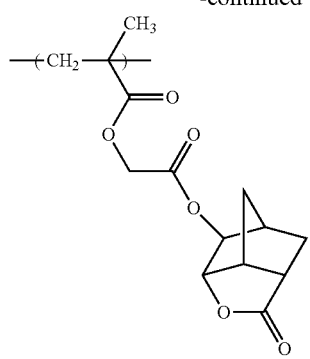
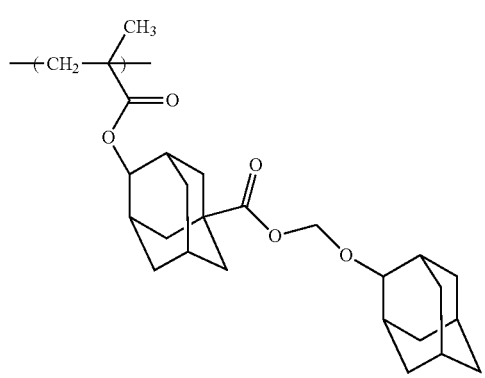
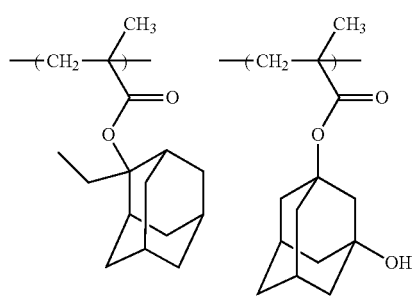
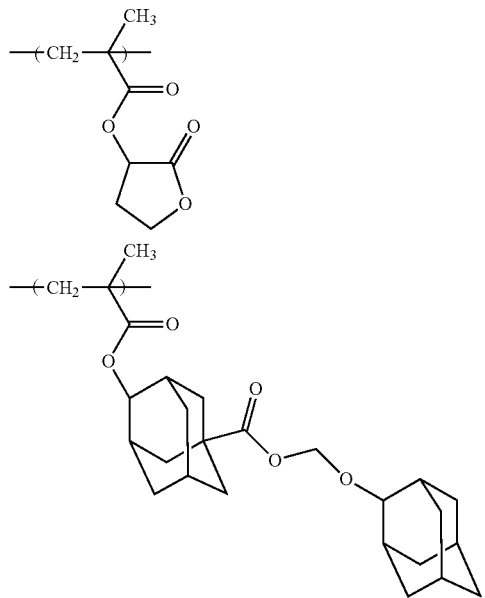
(A-39)
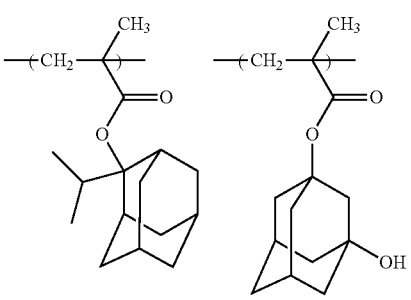 (A-40)
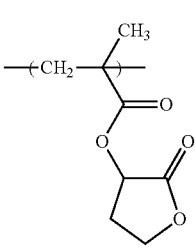
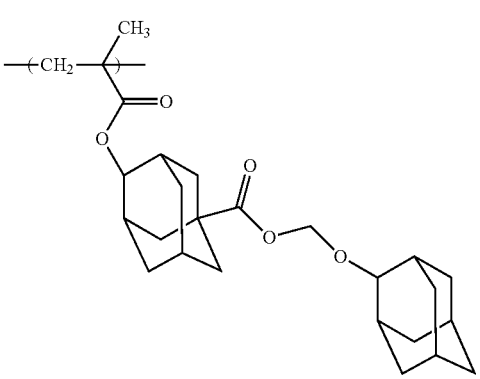
(A-41)
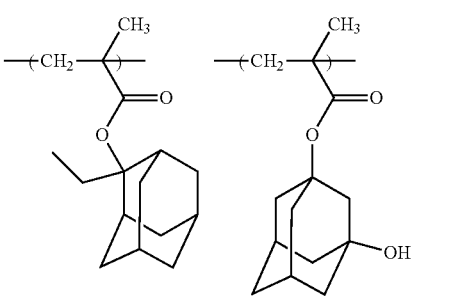

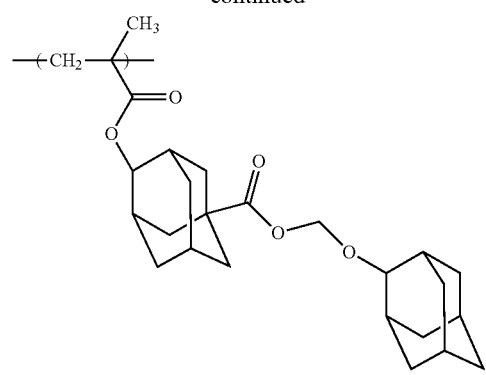
(A-42)
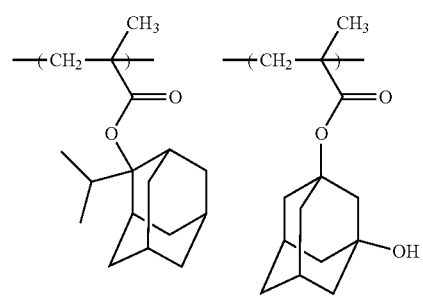
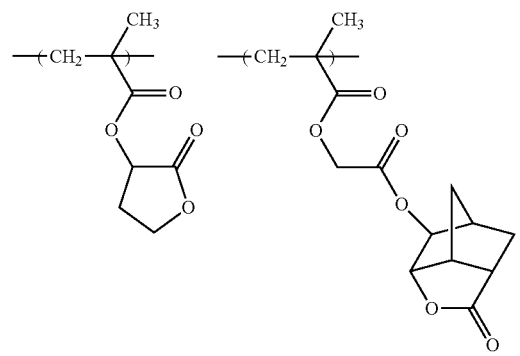
(A-43)
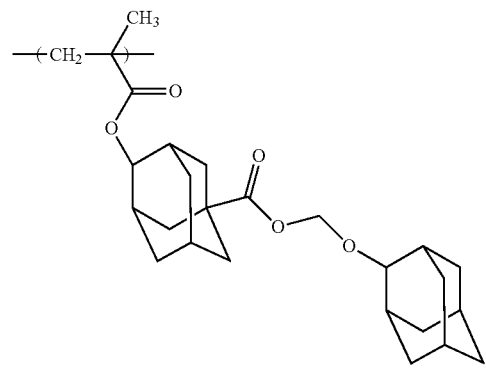
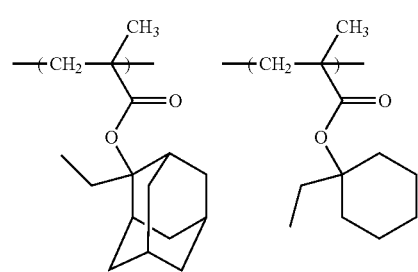
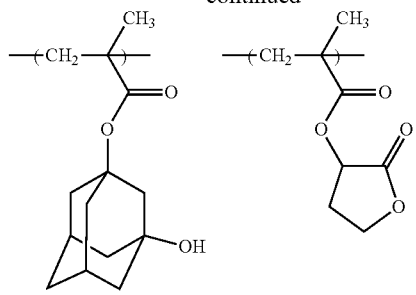
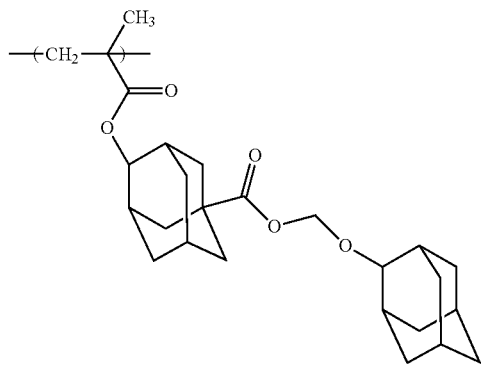
(A-44)
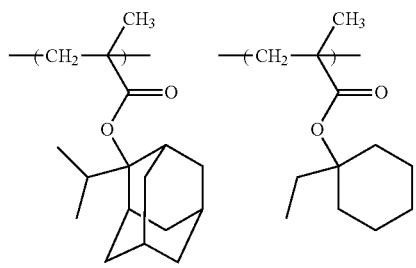
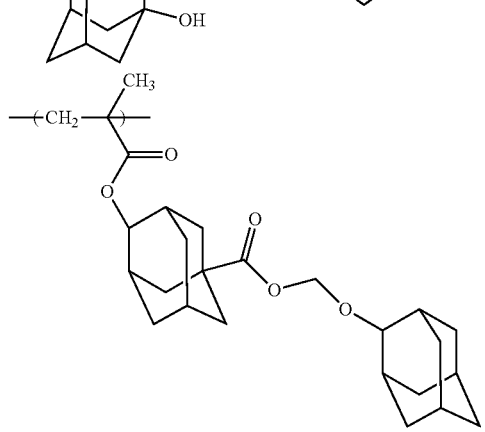

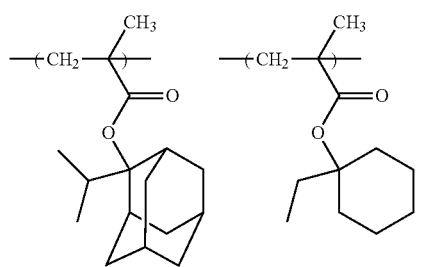
(A-45)
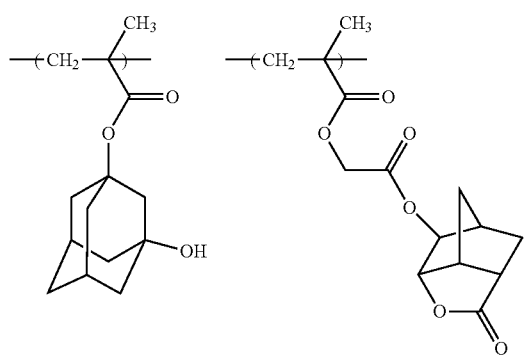
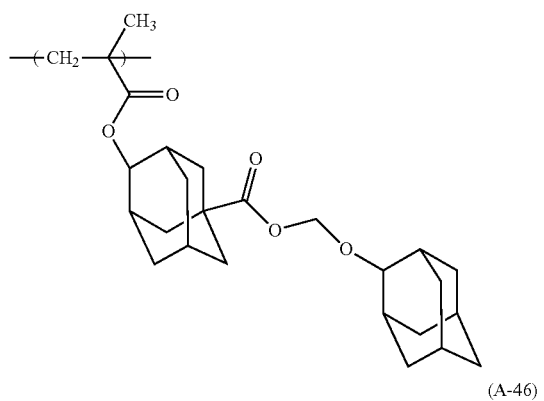
(A-46)
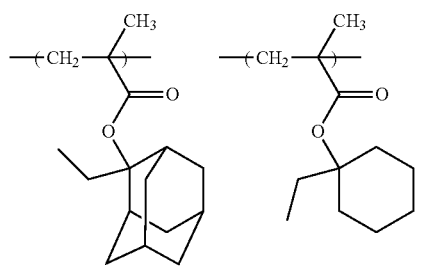
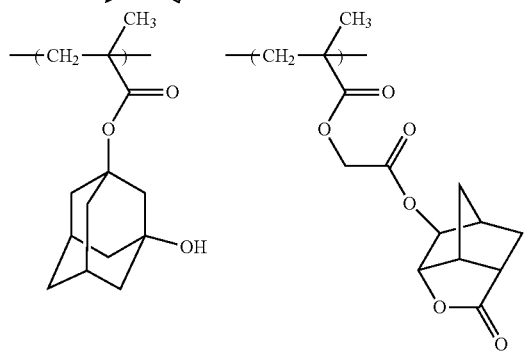
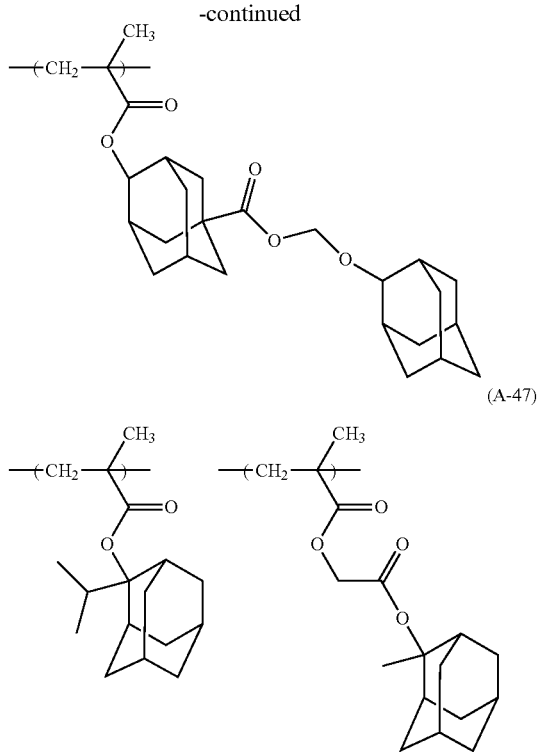
(A-47)
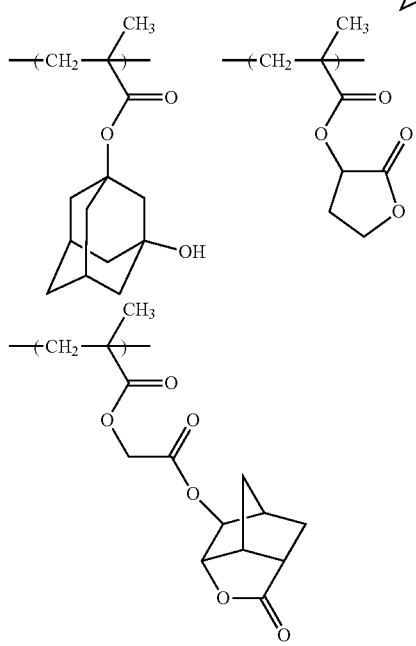
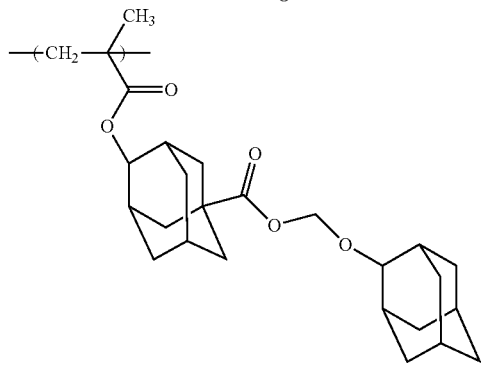

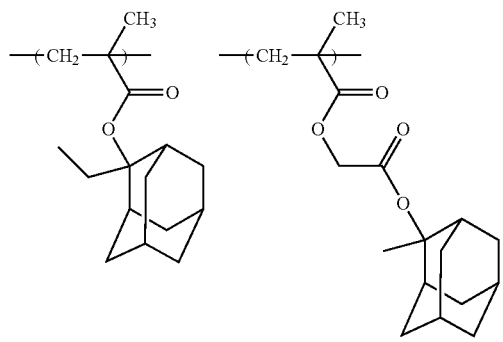
(A-48)
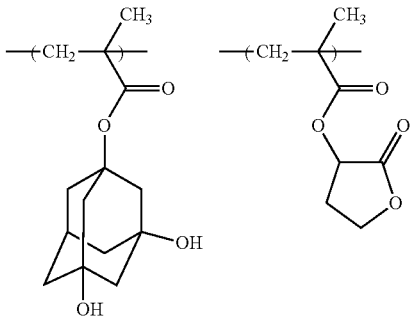
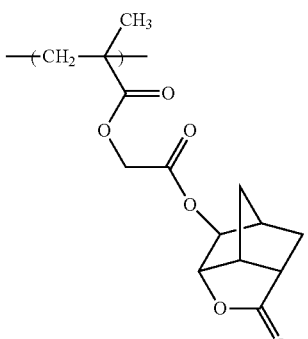
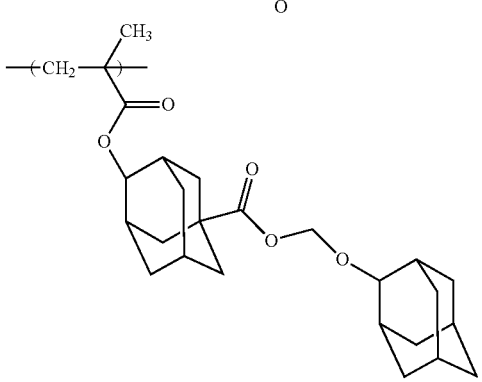
(A-50)
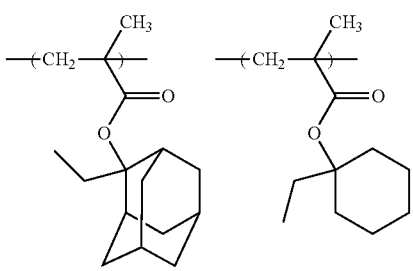
(A-49)
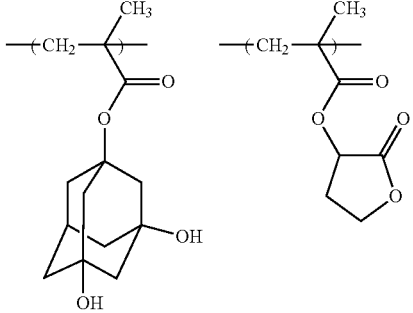

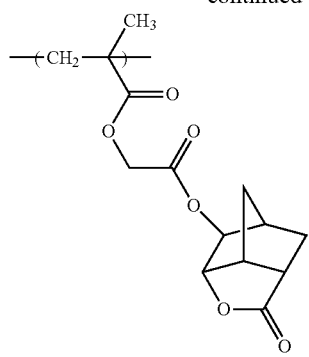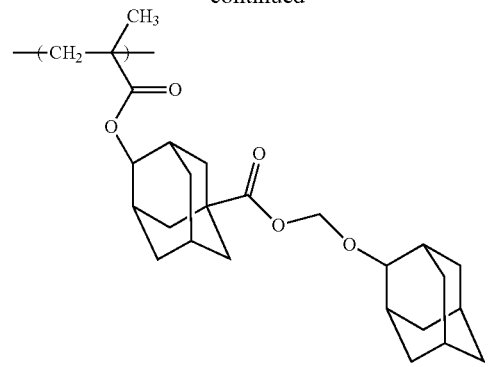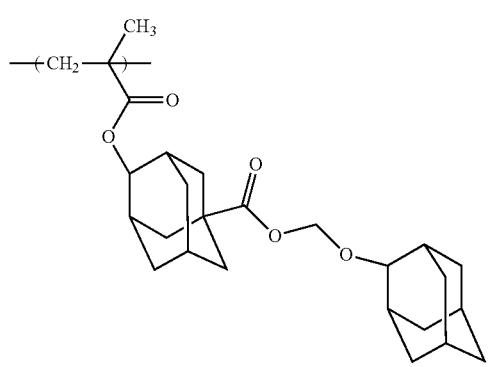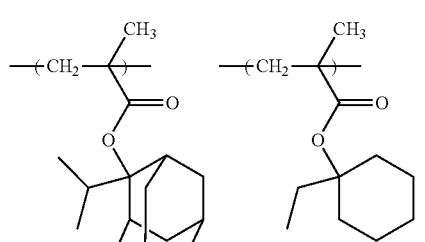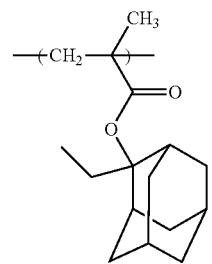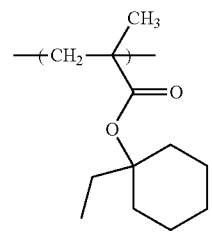
(A-51)
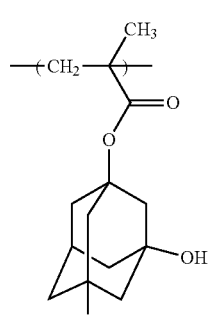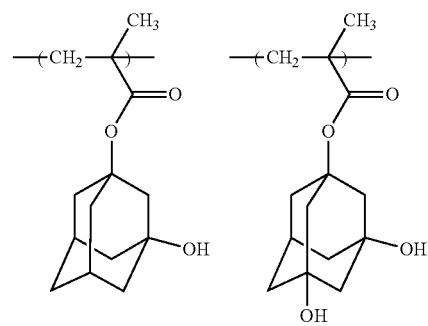
(A-52)
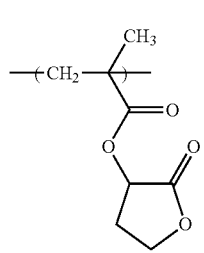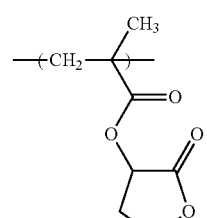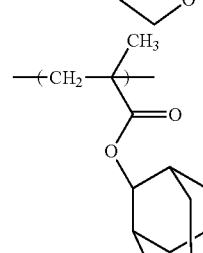

(A-53)

(A-54)

(A-55)

(A-56)

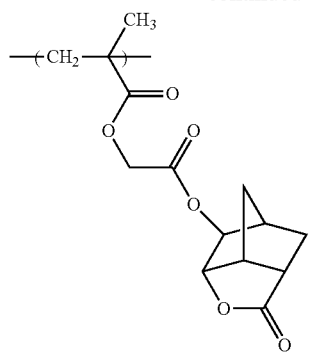
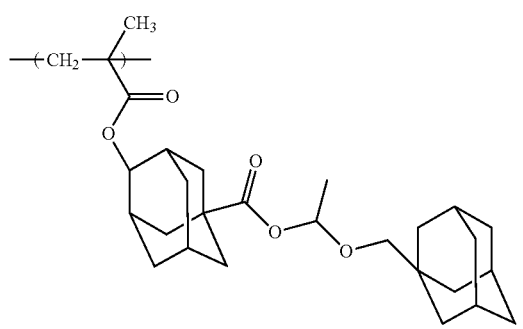
(A-57)
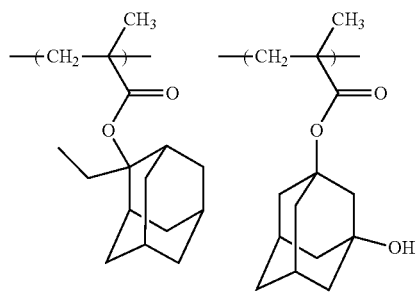
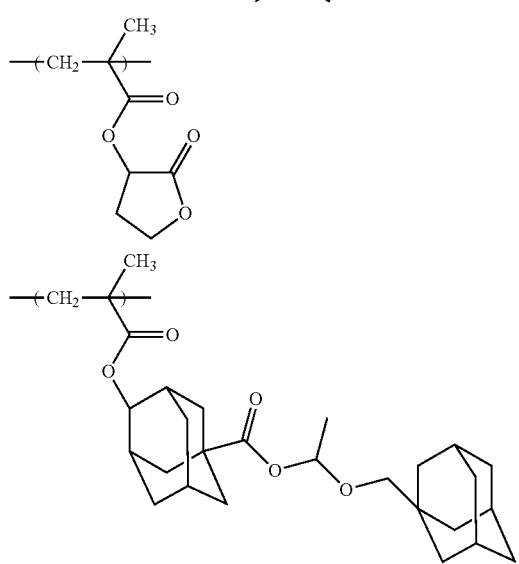
(A-58)
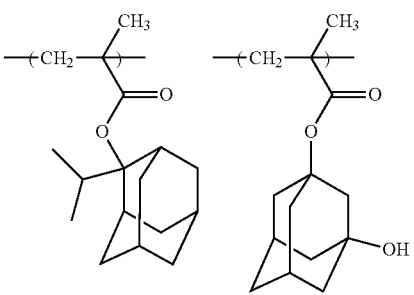
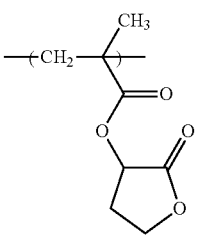
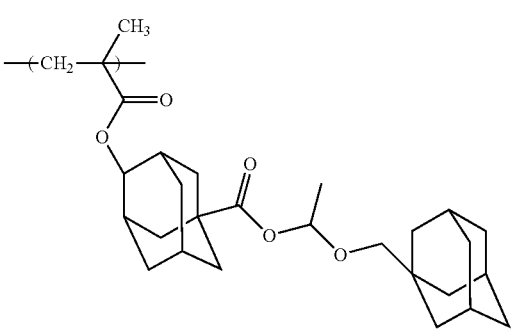
(A-59)
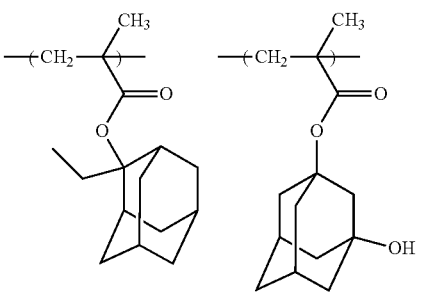
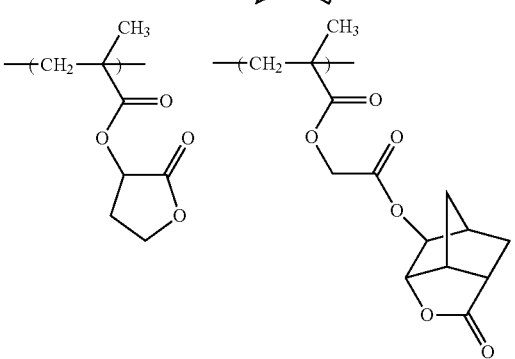

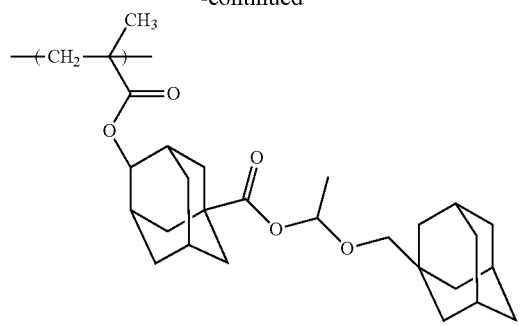
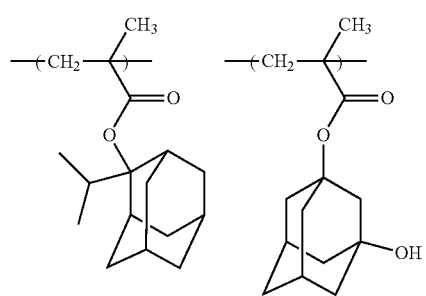
(A-60)
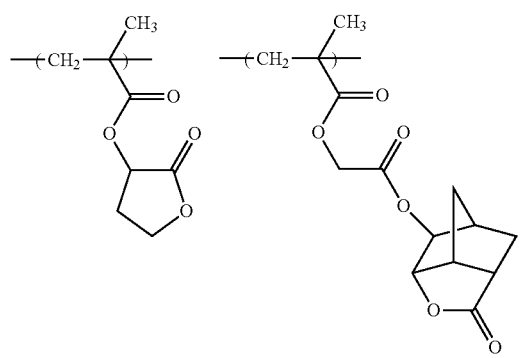
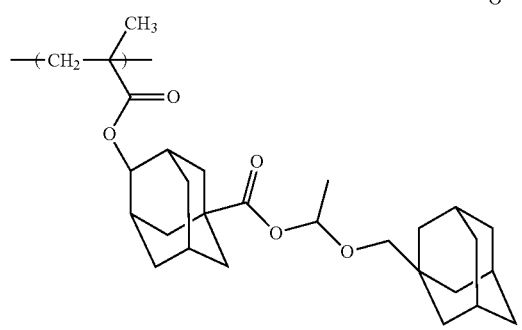
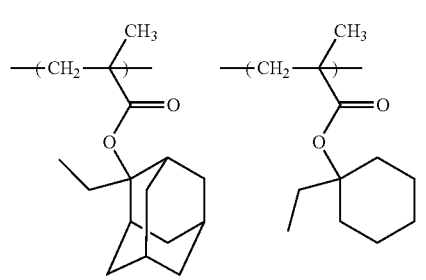
(A-61)
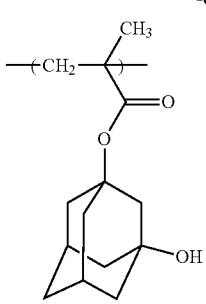
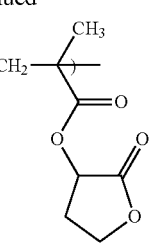
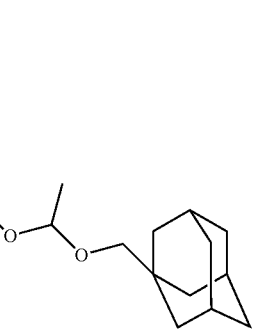
(A-62)
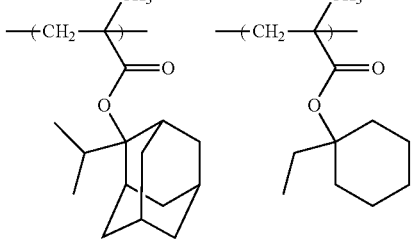
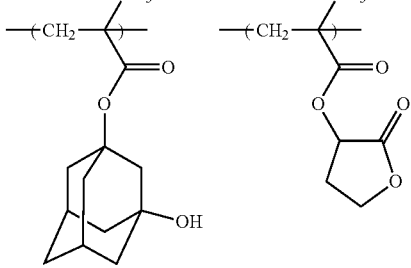
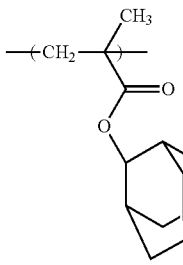

(A-63)
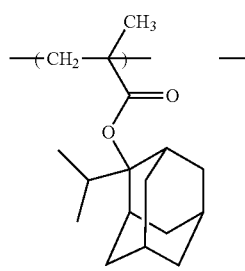 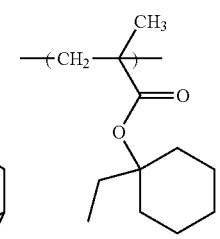
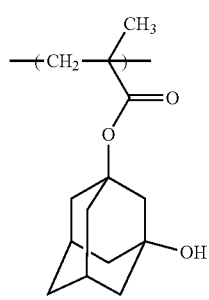 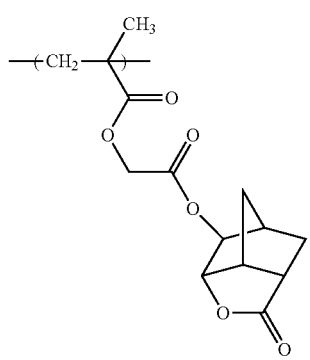
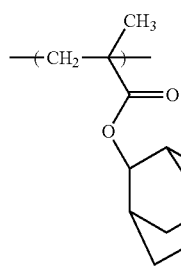
(A-64)
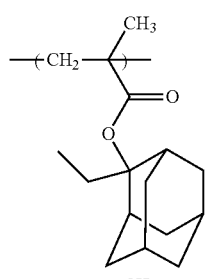
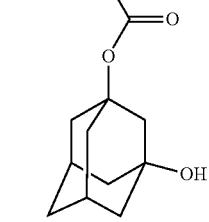 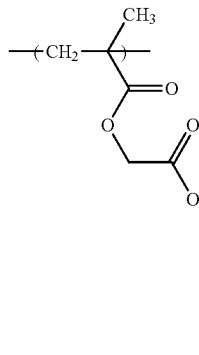
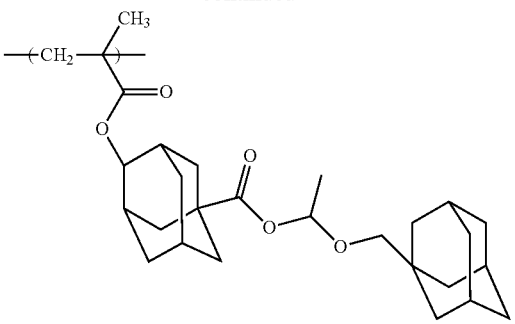
(A-65)
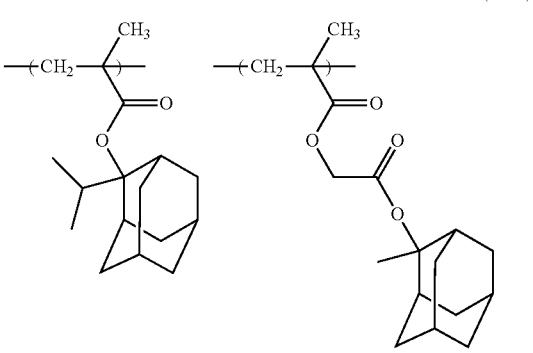
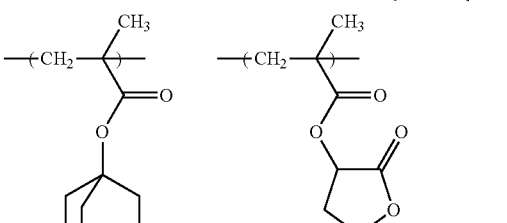
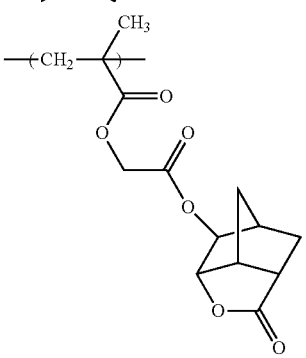
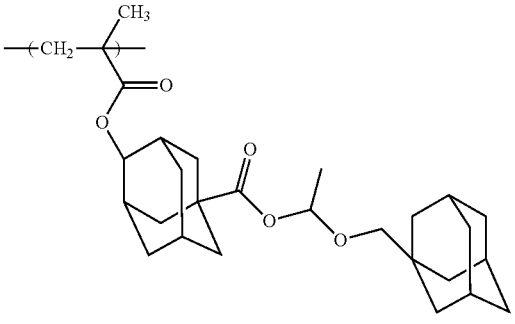

(A-66)
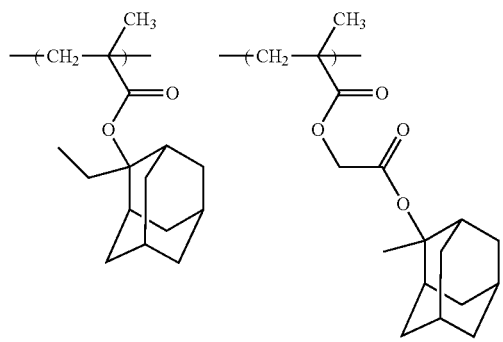
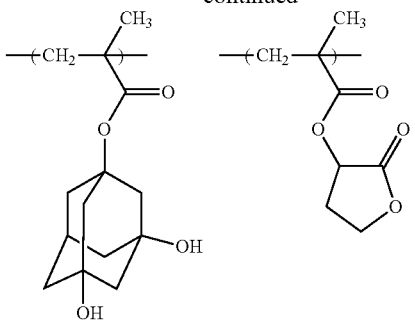
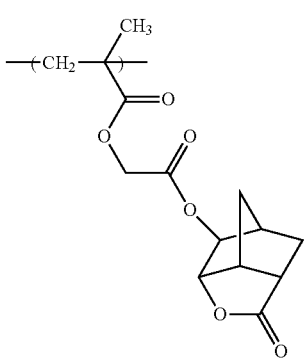
(A-67)
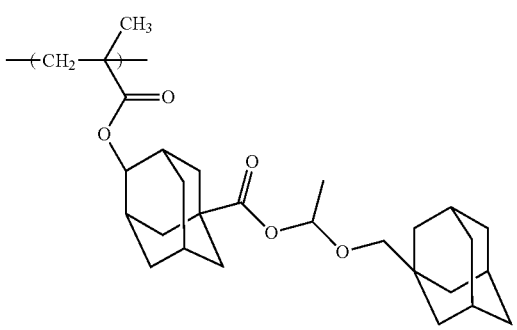
(A-68)
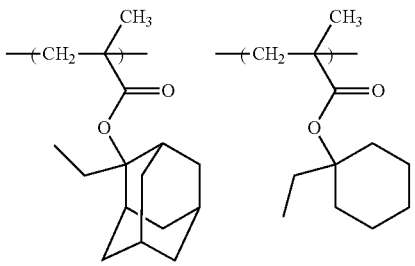
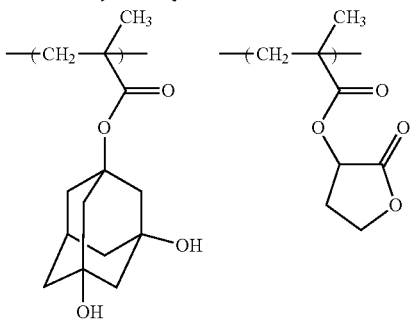

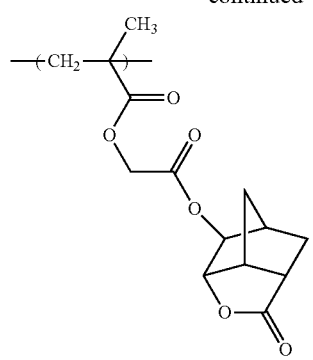
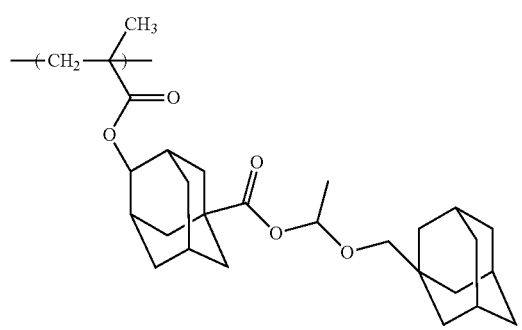
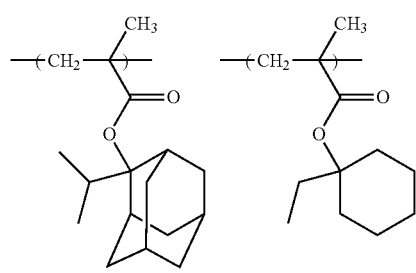 (A-69)
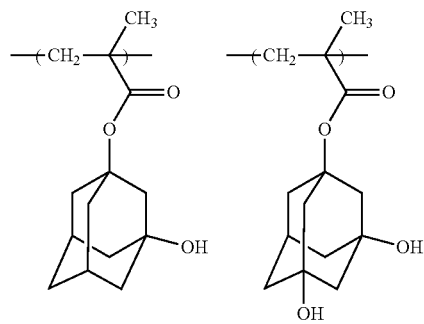
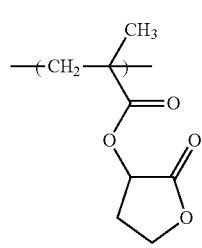
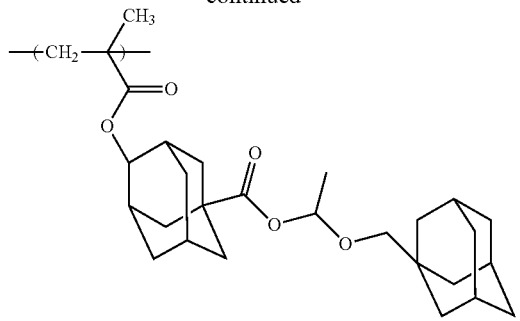
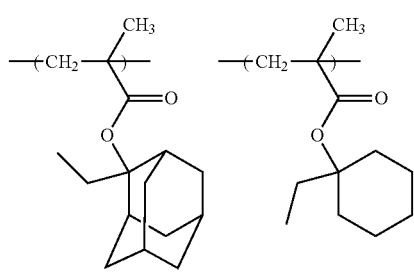 (A-70)
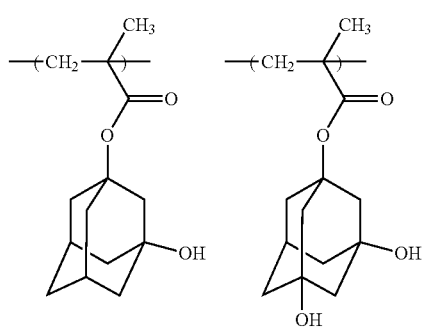
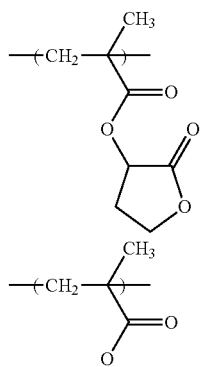
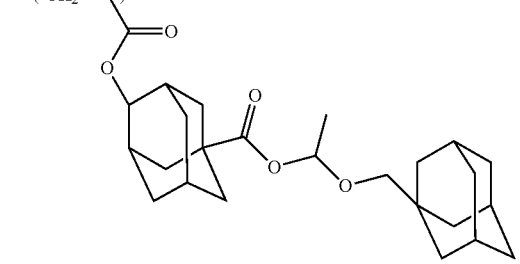

-continued

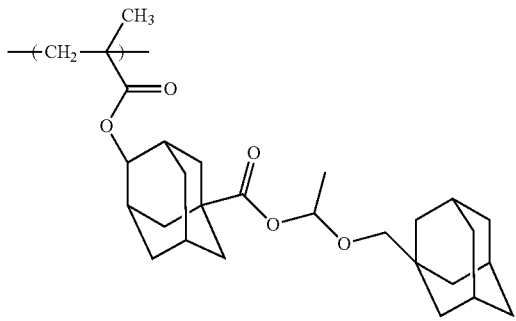
(A-71)

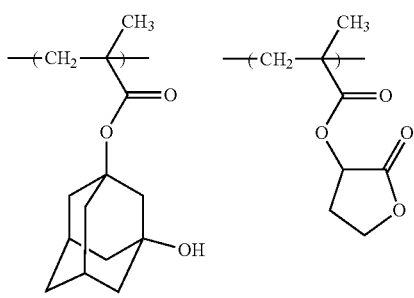

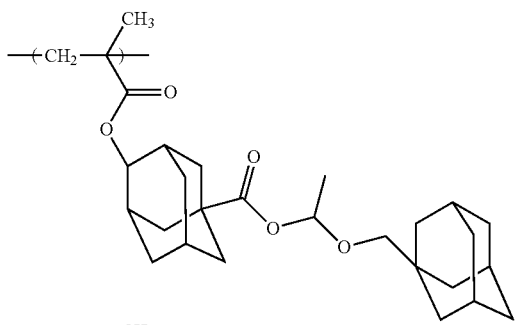
(A-72)

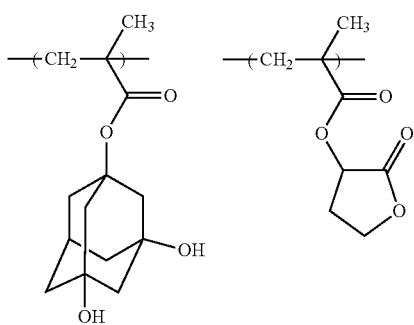

The resin of the present invention can be produced by polymerizing the compound represented by formula (I) according to known polymerization methods such as radical polymerization.

The resin of the present invention usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with known methods such as liquid chromatography, gas chromatography or gel permeation chromatography.

The photoresist composition of the present invention comprises the resin represented by formula (I), an acid generator and a solvent. The photoresist composition preferably further comprises a resin having a structural unit derived from a monomer having no acid-labile group but having a fluorine atom. The resin having a structural unit derived from a monomer having no acid-labile group but having a fluorine atom is free from a structural unit derived from the compound represented by formula (I).

The photoresist composition of the present invention usually includes 80% by weight or more of the resin based on sum of solid component. The photoresist composition of the present invention usually includes 99% by weight or less of the resin based on sum of solid component. In this specification, "solid component" means components other than solvent in the photoresist composition.

The photoresist composition preferably further comprises a basic compound.

The acid generator may be ionic compounds or nonionic compounds.

The nonionic compounds for the acid generator include organic halogenated compounds; sulfonate esters, e.g. 2-nitrobenzylester, aromatic sulfonates, oximesulfonate, N-sulfonyloxyimide, sulfonyloxyketone, and diazonaphtoquione 4-sulfonate; sulfones, e.g., disulfone, ketosulfone, and sulfonium diazomethane. The ionic compounds for the acid generator include onium salts having an onium cation, e.g., diazonium salts, phosphonium salts, sulfonium salts and iodonium salts. Anions of onium salt include a sulfonic acid anion, a sulfonylimide anion, sulfonylmethide anion. The photoresist composition may have one or more acid generators. As the acid generator, the compounds giving an acid by radiation can be used, which are mentioned in JP63-26653A1, JP55-164824A1, JP62-69263A1, JP63-146038A1, JP63-163452A1, JP62-153853A1, JP63-146029A1, U.S. Pat. No. 3,779,778B1, U.S. Pat. No. 3,849,137B1, DE3914407 and EP126,712A1. The acid generator for the photoresist composition can be produced by the method described in the above-mentioned documents.

The acid generator is preferably a fluorine-containing compound, more preferably salt represented by formula (B1)

(B1)

wherein $Q^1$ and $Q^2$ respectively represent a fluorine atom or a C1-C6 perfluoroalkyl group, $L^{b1}$ represents a single bond or a C1-C17 saturated hydrocarbon group in which a methylene group may be replaced by —O— or —CO—, Y represents a C1-C18 alkyl group which may have a substituent or a C3-C18 alicyclic hydrocarbon group which may have a substituent, where a methylene of the alkyl group and methylene of the alicyclic hydrocarbon group may be replaced by —O—, —SO— or —CO—, and $Z^+$ represents an organic cation.

Hereinafter, the moiety corresponding to the part except $Z^+$ in formula (I) and having a negative charge is sometimes referred to as "sulfonic acid anion".

Examples of the C1-C6 perfluoroalkyl group represented by $Q^1$ and $Q^2$ include a trifluoromethyl group, a pentafluoroethyl group, a heptafluoropropyl group, a nonafluorobutyl group, an undecafluoropentyl group and a tridecafluorohexyl group. It is preferred that $Q^1$ and $Q^2$ independently each represent a fluorine atom or a trifluoromethyl group, and it is more preferred that $Q^1$ and $Q^2$ are fluorine atoms.

The divalent saturated hydrocarbon group represented by $L^{b1}$ includes linear chain alkanediyl groups, branched chain alkanediyl groups, monocyclic or polycyclic divalent saturated hydrocarbon groups, and a group combining two or more of the above-mentioned groups. Examples of $L^{b1}$ include linear chain alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group, a propane-2,2-diyl group; branched chain groups such as a group formed by attaching a side chain to a linear hydrocarbon group (e.g., a 1-methylbutan-1,3-diyl group, a 2-methylpropane-1,3-diyl group, a 2-methylpropane-1,2-diyl group, a pentane-1,4-diyl group, and a 2-methylbutane-1,4-diyl group); divalent alicyclic hydrocarbon groups including cycloalkanediyl groups such as a cyclohexane-1,2-diyl group, a 1-methylcyclohexane-1,2-diyl group, and cyclohexane-1,4-diyl; and a polycyclic divalent alicyclic hydrocarbon groups such as a norbornane-1,4-diyl group, a norbornane-1,5-diyl group, an amadantane-1,5-diyl group, or an amadantane-2,6-diyl group. Examples of the divalent saturated hydrocarbon group in which a methylene group has been replaced by an oxygen atom or a carbonyl group include groups represented by the formula (b1-1), the formula (b1-2), the formula (b1-3), the formula (b1-4), the formula (b1-5) and the formula (b1-6) as follow.

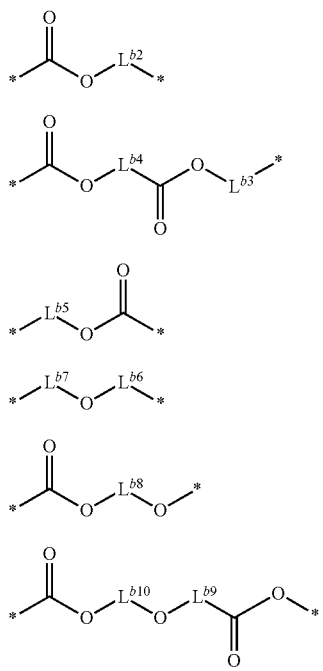

wherein $L^{b2}$ represents a single bond or a C1-C15 divalent hydrocarbon group,
$L^{b3}$ represents a single bond or a C1-C12 divalent hydrocarbon group,
$L^{b4}$ represents a C1-C13 divalent hydrocarbon group provided that the total carbon atoms of $L^{b3}$ and $L^{b4}$ is up to 13,
$L^{b5}$ represents a divalent C1-C15 divalent hydrocarbon group, $L^{b6}$ and $L^{b7}$ respectively represent a C1-C15 divalent hydrocarbon group, with the proviso that total carbon number of $L^{b6}$ and $L^{b7}$ is up to 16,
$L^{b8}$ represents a C1-C14 divalent hydrocarbon group,
$L^{b9}$ and $L^{b10}$ respectively represent a C1-C11 divalent hydrocarbon group, with the proviso that total carbon number of $L^{b9}$ and $L^{b10}$ is up to 12,
* represents a binding position, * of the left side represents a binding position to —$C(Q^1)(Q^2)$, and * of the right side represents a binding position the ring $W^1$.

$L^{b1}$ is preferably the moieties represented by any one of formulae (b1-1) to (b1-4), more preferably the moieties represented by any formula (b1-1) or (b1-2), still more preferably the moieties represented by formula (b1-1). Among the moieties represented by formula (b1-1), preferred are those in which $L^{b2}$ represents a single bond or a methylene group.

The moieties represented by formula (b1-1) include those as follow.

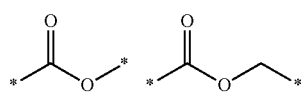

The moieties represented by formula (b1-2) include those as follow.

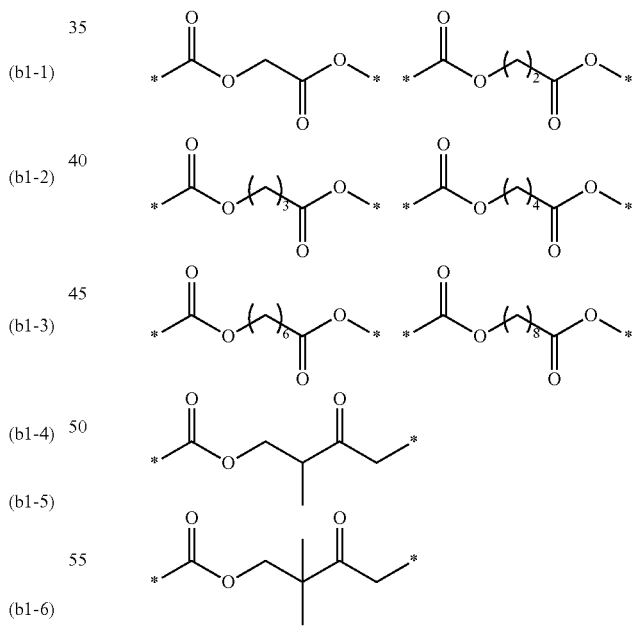

The moieties represented by formula (b1-3) include those as follow.

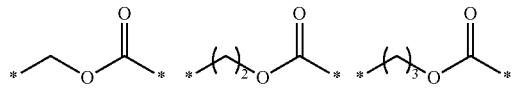

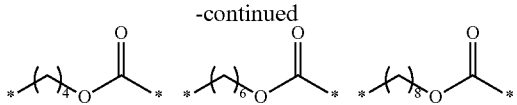

The moieties represented by formula (b1-4) include those as follow.

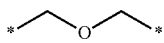 [SMILES: *COC*]

The moieties represented by formula (b1-5) include those as follow.

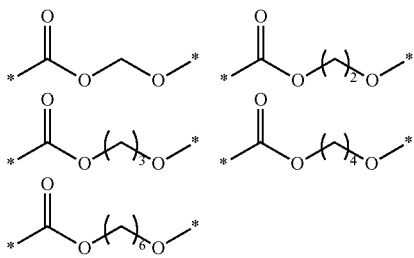

The moieties represented by formula (b1-6) include those as follow.

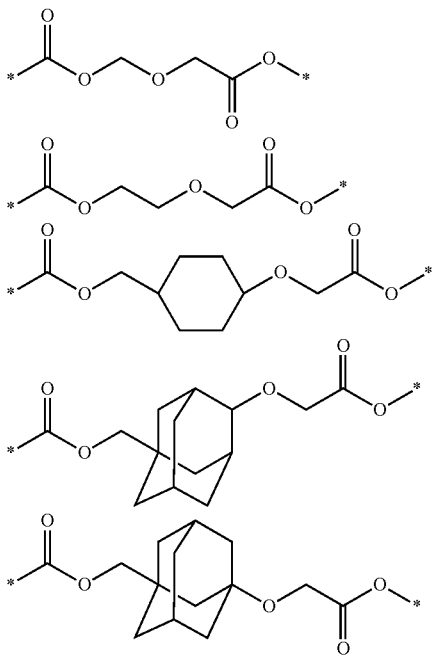

Examples of alkyl groups represented by Y include linear chain or branched chain alkyl groups such as a methyl group, an ethyl group, a propyl group, a butyl group, a pentyl group and a hexyl group, a pentyl group, a hexyl group, a heptyl group, an octyl group, a nonyl group, a decyl group, an undecyl group, dodecyl group, preferably a C1-C6 alkyl group.

Preferable examples of the alicyclic hydrocarbon group represented by Y include those represented by the formula (Y1), the formula (Y2), the formula (Y3), the formula (Y4), the formula (Y5), the formula (Y6), the formula (Y7), the formula (Y8), the formula (Y9), the formula (Y10) and the formula (Y11).

When a methylene group has been replaced by an oxygen atom or a carbonyl group in the alkyl or alicyclic hydrocarbon group represented by Y, preferable examples of Y include those represented by the formula (Y12), the formula (Y13), the formula (Y14), the formula (Y15), the formula (Y16), the formula (Y17), the formula (118), the formula (Y19), the formula (Y20), the formula (Y21), the formula (Y22), the formula (Y23), the formula (Y24), the formula (Y25) and the formula (Y26) or other group in which a methylene group of alkylene group has been replaced by an oxygen atom or a carbonyl group in the alkyl or alicyclic hydrocarbon group,

 (Y1)

 (Y2)

 (Y3)

 (Y4)

 (Y5)

 (Y6)

 (Y7)

 (Y8)

 (Y9)

 (Y10)

(Y11) 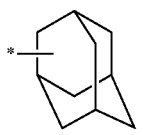

(Y12) 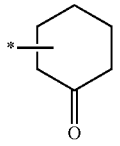

(Y13) 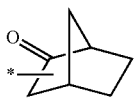

(Y14) 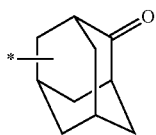

(Y15) 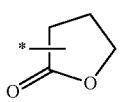

(Y16) 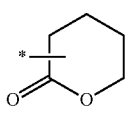

(Y17) 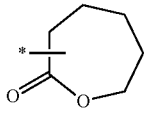

(Y18) 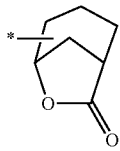

(Y19) 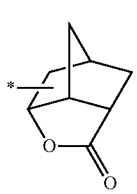

(Y20) 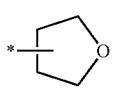

(Y21) 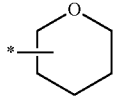

(Y22) 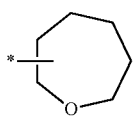

(Y23) 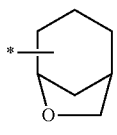

(Y24) 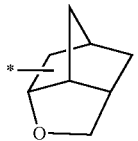

(Y25) 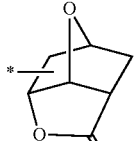

(Y26) 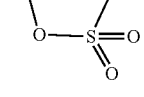

Among the groups represented by the formula (Y1) to the formula (Y26), preferred are those represented by the formula (Y11), the formula (Y12), the formula (Y13), the formula (Y14), the formula (Y15), the formula (Y16), the formula (Y17), the formula (Y18) or the formula (Y19); more preferred are those represented by the formula (Y11), the formula (Y14), the formula (Y15) or the formula (Y19); and still more preferred are those represented by the formula (Y11) or the formula (Y14).

Substituents of the alkyl groups represented by Y include a halogen group, a hydroxyl group, a C1-C12 alkoxy group, a C3-C16 alicyclic hydrocarbon group, a C6-C18 aromatic hydrocarbon group, a C7-C21 aralkyl group, a C2-C4 acyl group, a glycidyloxy group, and —$(CH_2)_{j2}$—O—CO—$R^{b1}$— in which $R^{b1}$ represents an C1-C16 alkyl group, a C3-C16 alicyclic hydrocarbon group, or a C6-C18 aromatic hydrocarbon group, and j2 represents an integer of 0 to 4. Each of the alkyl group, the alicyclic hydrocarbon group, the aromatic hydrocarbon group and the aralkyl group, which is the substituent for the alkyl hydrocarbon groups represented by Y may have a substituent such as a halogen group or a hydroxyl group.

Substituents of the alicyclic hydrocarbon groups represented by Y include a halogen group, an C1-C12 alkyl group, a hydroxyl group, a C1-C12 alkoxy group, a C3-C16 alicyclic hydrocarbon group, a C6-C18 aromatic hydrocarbon group, a C7-C21 aralkyl group, a C2-C4 acyl group, a glycidyloxy group, and —$(CH_2)_{j2}$—O—CO—$R^{b1}$— in which $R^{b1}$ and j2 are defined as above. Each of the alkyl group, the alicyclic hydrocarbon group, the aromatic hydrocarbon group and the aralkyl group, which is the substituent for the alicyclic hydrocarbon groups represented by Y may have a substituent such as an alkyl group, a halogen group or a hydroxyl group.

Examples of the halogen atom include a fluorine atom, a chlorine atom, a bromine atom and an iodine atom.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the aralkyl group include a benzyl group, phenylpropyl group, a phenethyl group, a naphthylmethyl group, or a naphthylethyl group.

Examples of the C2-C4 acyl group include an acetyl group, a propynoyl group and a butyryl group.

Examples of Y include the groups as follow.

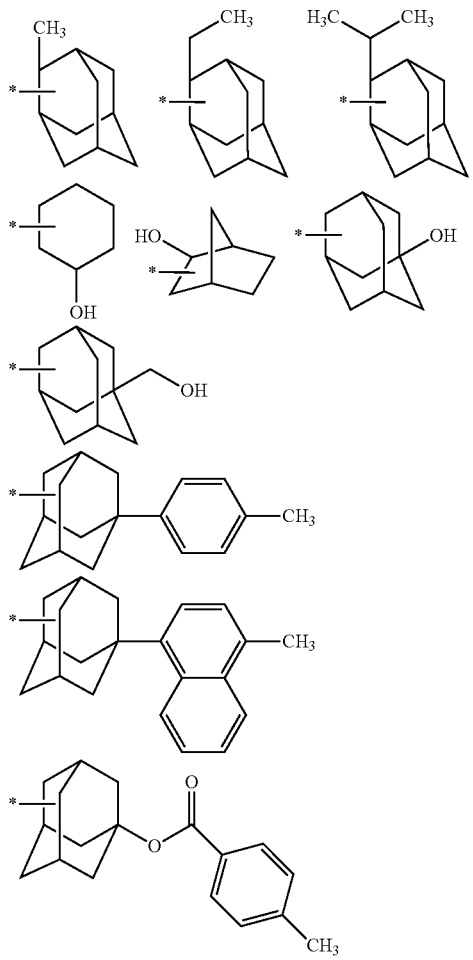

When Y represents an aliphatic hydrocarbon group, $L^{b1}$ represents a C1-C17 divalent hydrocarbon group, it is preferred that a methylene group of the divalent aliphatic hydrocarbon group binding to Y has been replaced by an oxygen atom or a carbonyl group. When a methylene group of the divalent aliphatic hydrocarbon group binding to Y has been replaced by an oxygen atom or a carbonyl group, a methylene group of the aliphatic hydrocarbon group represented by Y is not replaced by an oxygen atom or a carbonyl, group. Y represents preferably a C3-C18 alicyclic hydrocarbon group which may have a substituent, more preferably an amadantyl group which may have a substituent, and still more preferably an amadantyl group, a hydroxyamadantyl group or an oxoamadantyl group.

Preferable examples of the sulfonic acid anion of the salt represented by formula (B1) include salts represented by the formulae (b1-1-1), (b1-1-2), (b1-1-3) (b1-1-4) (b1-1-5) (b1-1-6) (b1-1-7) (b1-1-8) and (b1-1-9).

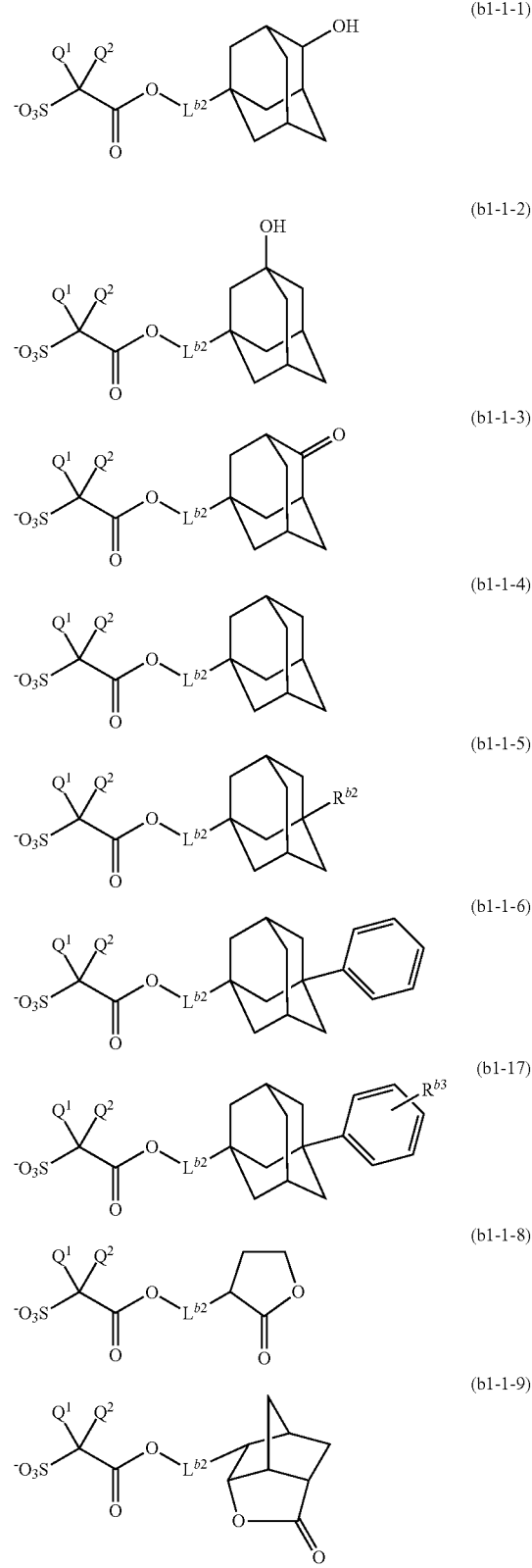

In these formulae, the symbols $Q^1$, $Q^2$, $L^{b2}$, Y and $Z^+$ are defined as above, and $R^{b2}$ and $R^{b3}$ each independently represent a C1-C4 alkyl group, preferably a methyl group.

Specific examples of the sulfonic acid anion of the salt represented by formula (B1) include anions mentioned in JP2010-204646A1. Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. Herein, the arylsulfonium includes those having one, two or three aryl groups.

Preferable examples of the organic cations represented by $Z^+$ include those represented by the formulae (b2-1) to (b2-4):

$R^{b11}$ represents a hydrogen atom, a C1-C18 alkyl group, or a C3-C18 alicyclic hydrocarbon group, and $R^{b12}$ represents a C1-C12 alkyl group, a C3-C18 alicyclic hydrocarbon group, a C6-C18 aromatic hydrocarbon group which can have a substituent selected from the group consisting of a C1-C12 alkyl group, a C1-C12 alkoxyl group, C1-C18 alicyclic hydrocarbon group and a C2-C12 alkyl carbonyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by an oxygen atom, sulfur atom or carbonyl group, and

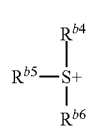
(b2-1)

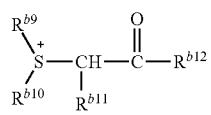
(b2-2)

(b2-3)

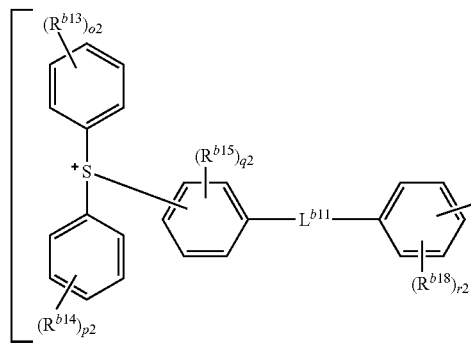
(b2-4)

wherein $R^{b4}$, $R^{b5}$, and $R^{b6}$ independently represent a C1-C30 alkyl group which can have a substituent selected from the group consisting of a hydroxyl group, a C1-C12 alkoxy group, a C6-C18 aromatic hydrocarbon group, a C3-C18 alicyclic hydrocarbon group which cap have a substituent selected from the group consisting of a halogen atom, a C2-C4 acyl group and a glycidyloxy group, and a C6-C18 aromatic hydrocarbon group which can have a substituent selected from the group consisting of a halogen atom, a hydroxyl group, C1-C18 alicyclic hydrocarbon group, or C1-C12 alkoxy group, and $R^{b4}$ and $R^{b5}$, $R^{b4}$ and $R^{b6}$, or $R^{b5}$ and $R^{b6}$ can be bonded each other to form a ring containing S$^+$, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{b10}$ independently represent a C1-C10 alkyl group or a C3-C10 alicyclic hydrocarbon group, or $R^{b9}$ and $R^{b10}$ are bonded each other to form a C1-C10 divalent acyclic hydrocarbon group which forms a 3- to 12-membered ring, preferably 3- to 7-membered ring together with the adjacent —S$^+$-, and one or more —CH$_2$— in the divalent acyclic hydrocarbon group may be replaced by an oxygen atom, sulfur atom or carbonyl group, and $R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O—, o2, p2, s2 and t2 each independently represents an integer of 0 to 5, g2 and r2 each independently represents an integer of 0 to 4, and u2 represents 0 or 1.

Examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and preferable examples thereof include a methyl group, an ethyl group, a propyl group and a butyl group. The alicyclic hydrocarbon group represented by $R^{b4}$ to $R^{b6}$ may be monocyclic or polycyclic. The monocyclic alicyclic hydrocarbon group includes cycloalkyl groups such as a cyclopropyl group, a cyclobutyl group, a cyclopentyl group, a cyclohexyl group, a cycloheptyl group, and a cyclodecyl group. The polycyclic alicyclic hydrocarbon group includes cycloalkyl groups such as decahydronaphthyl group, an adamantyl group, a norbornyl group, a methylnorbornyl group, and other polycyclic groups as mentioned bellow.

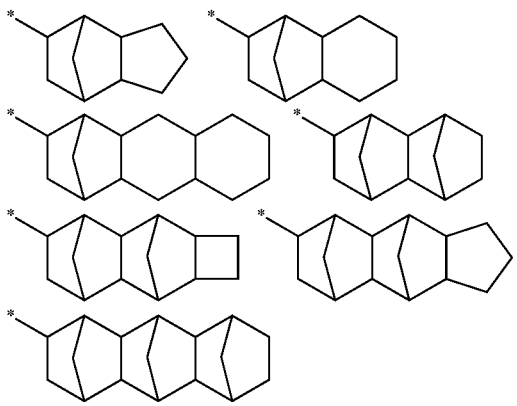

wherein * represents a binding site to an adamantane ring or a cyclohexane ring.

Preferable examples of the alicyclic hydrocarbon group include a cyclopentyl group and a cyclohexyl group.

Examples of the aromatic group represented by $R^{b4}$ to $R^{b6}$ include an aryl group such as a phenyl group, a naphthyl group, p-methyl phenyl group, p-ethyl phenyl group, p-tert butyl phenyl group, p-adamantyl phenyl group, tolyl group, xylyl group, cumenyl group, mesityl group, biphenyl, group, phenantolyl group, 2,6-diethylphenyl group and 2-methyl-6-ethylphenyl group.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the halogen atom include a fluorine atom, a chlorine atom, a bromine atom and an iodine atom.

Examples of the C2-C4 acyl group include an acetyl group, a propynoyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 18 carbon atoms.

Examples of the alkyl group represented by $R^{b7}$ and $R^{b8}$ include a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the C1-C12 alkoxy group represented by $R^{b7}$ and $R^{b8}$ include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkyl group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Such alkyl group preferably has 1 to 12 carbon atoms. Examples of the alicyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group.

The alicyclic hydrocarbon group represented by $R^{b9}$ to $R^{b11}$ has preferably 4 to 12 carbon atoms.

Preferable examples of the aromatic group represented by $R^{b12}$ include a phenyl group, 4-methyl phenyl group, 4-ethyl phenyl group, 4-tert butyl phenyl group, 4-cyclohexyl phenyl group, 4-methoxy phenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group.

Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiophenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group. Examples of the ring include oxocyclopentane ring, oxocyclohexane ring, oxonorbornane ring and oxoamadantane ring. A C1-C5 divalent acyclic hydrocarbon group is preferable.

Among the above-mentioned cations, preferred is the cation represented by the formula (b2-1) or the formula (b2-2), more preferred is the cation represented by the formula (b2-1), still more preferred is the cation represented by the formula (b2-1) in which any of $R^{b9}$, $R^{b5}$ and $R^{b6}$ is an aromatic hydrocarbon group, and particularly more preferred is the cation represented by the formula (b2-1-1).

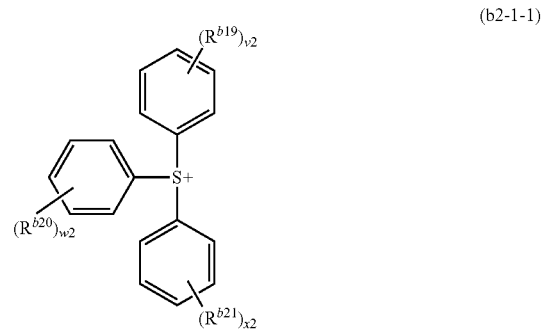

(b2-1-1)

wherein $R^{b19}$, $R^{b20}$ and $R^{b21}$ are independently in each occurrence a halogen atom (preferably a fluorine atom), a hydroxyl group, a C1-C18 alkyl group, a C3-C18 saturated cyclic hydrocarbon group or a C1-C12 alkoxy group, and $R^{b19}$ and $R^{b20}$, $R^{b19}$ and $R^{b21}$ or $R^{b20}$ and $R^{b21}$ can be bonded each other to form a ring together with $S^+$ and v2, w2 and x2 independently each represent an integer of 0 to 5.

The alkyl group has preferably 1 to 12 carbon atoms, more preferably C1-12 alkyl group, and the saturated cyclic hydrocarbon group has preferably 4 to 18 carbon atoms. Each of $R^{b19}$, $R^{b20}$ and $R^{b21}$ is preferably a halogen atom (preferably a fluorine atom), a hydroxyl group, a C1-C12 alkyl group and a C1-C12 alkoxy group.

The v2, w2 and x2 independently each preferably represent 0 or 1.

As examples of the organic cations represented by formulae (b2-1) to (b2-4) includes organic cations mentioned in JP2010-204646A1.

It is more preferred that $R^{b19}$, $R^{b20}$ and $R^{b21}$ are independently in each occurrence a halogen atom, specifically a fluorine atom, a hydroxyl group, a C1-C12 alkyl group or a C1-C12 alkoxy group, and v2, w2 and x2 independently each represent 0 or 1.

As the cation represented by the formula (b2-1-1), a triphenylsulfonium cation and a trytolysulfonium cation are especially preferable.

Examples of the salt represented by formula (B1) include a salt wherein the anion is any one of the above-mentioned anions and the counter ion is any one of organic counter ions. Preferred salt represented by formula (B1) are those consisting of cation represented by formula (b2-1-1) and any one of anions represented by formulae (b1-1-1) to (b1-1-9) as well as those consisting of cation represented by formula (b2-1-3) and any one of anions represented by formulae (b1-1-3), (b1-1-4) and (b1-1-9).

The salt represented by formula (B1) are preferably salts represented by formulae (B1-1) to (B1-20), and more preferably salts which have triphenylsulfonium cation or tritolylsulfonium cation, i.e., salts represented by formulae (B1-1), (B1-2), (B1-3), (B1-6), (B1-7), (B1-11), (B1-12), (B1-13) and (B1-14).

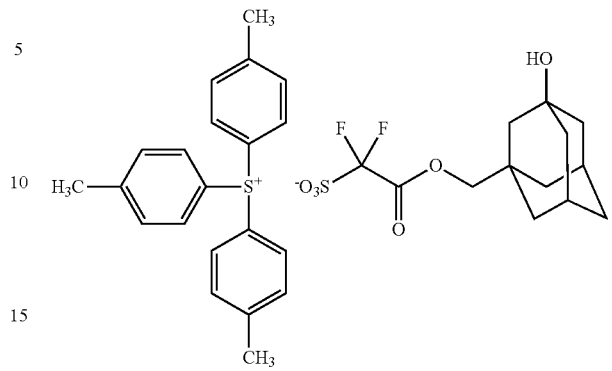
(B1-3)

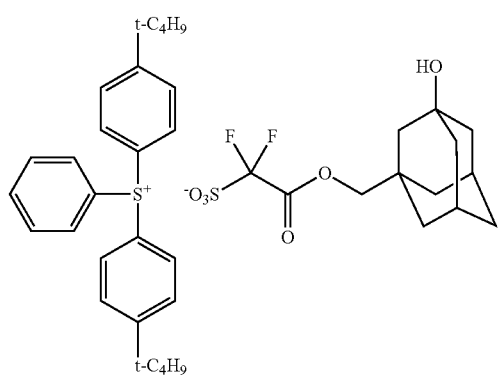
(B1-4)

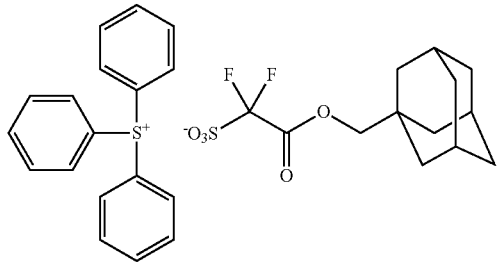
(B1-1)

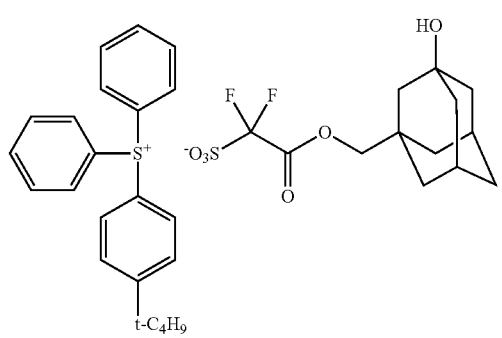
(B1-5)

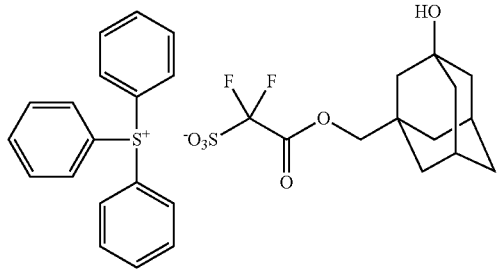
(B1-2)

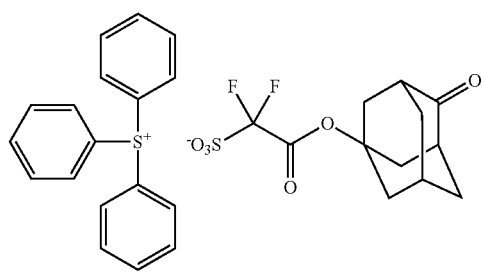
(B1-6)

(B1-7)
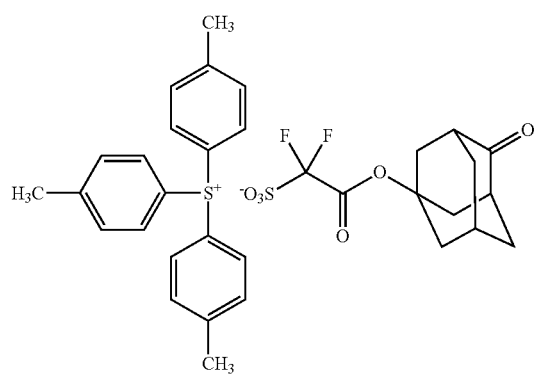
(B1-11)
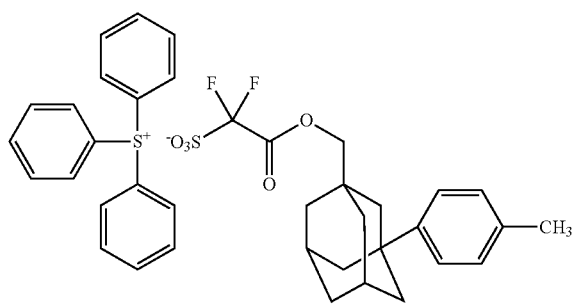
(B1-8)
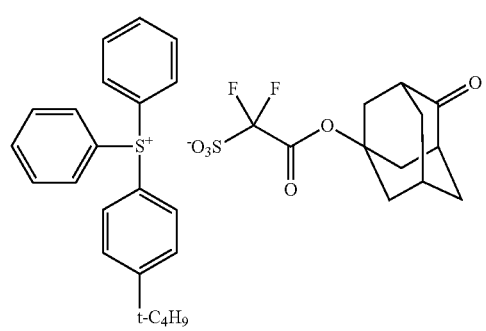
(B1-12)
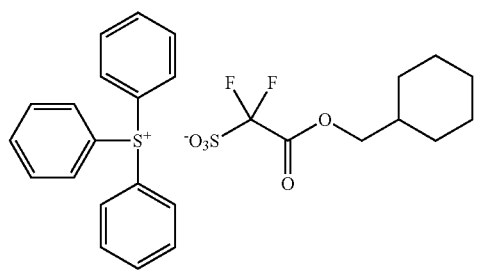
(B1-13)
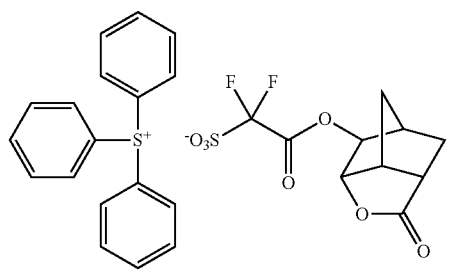
(B1-9)
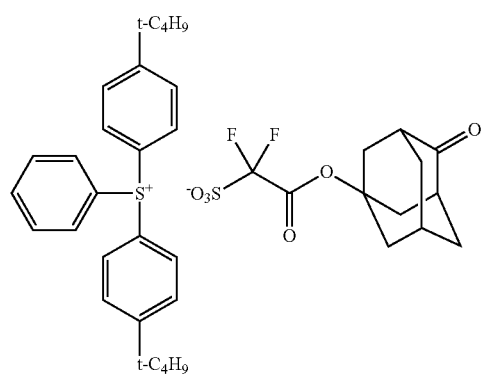
(B1-14)
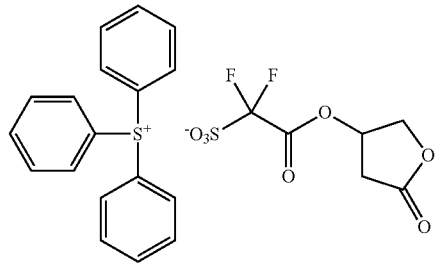
(B1-10)
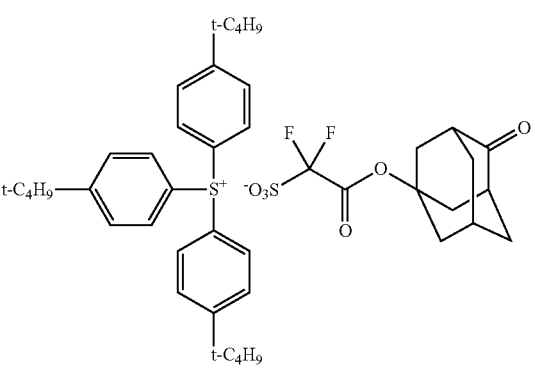
(B1-15)
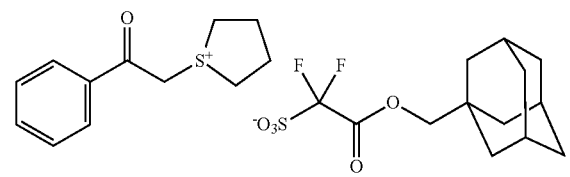
(B1-16)
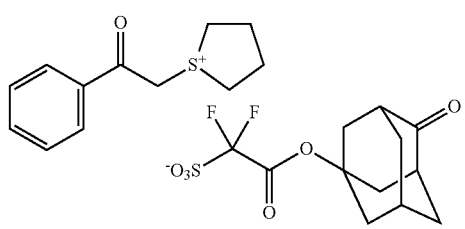

-continued (B1-17)
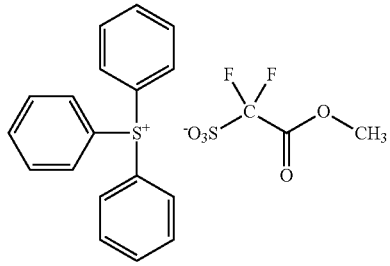

(B1-18)
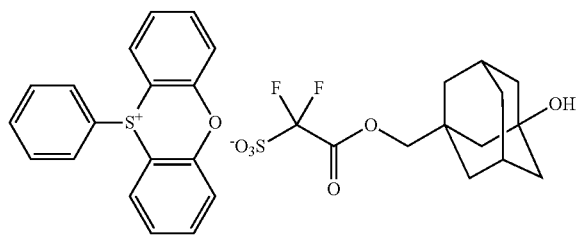

(B1-19)
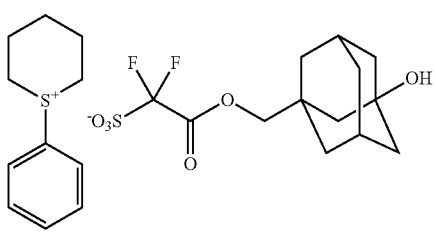

(B1-20)
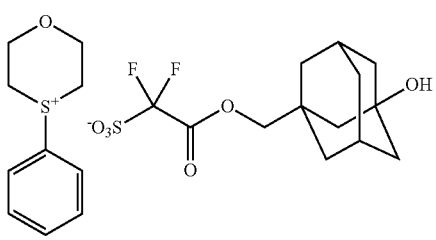

The content of the acid generator is preferably 1 parts by weight or more and more preferably 3 parts by weight or more per 100 parts by weight of the resin of the present invention, and the content of the acid generator is preferably 40 parts by weight or less and more preferably 35 parts by weight or less per 100 parts by weight of the resin.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine, an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Examples of the basic compound include preferably compounds represented by the formulae (C1) to (C8), more preferably compounds represented by the formula (C1), still more preferably (C1-1):

(C1)
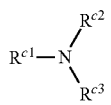

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxyl group, an amino group and a C1-C6 alkoxy group, and the aromatic hydrocarbon group can have a substituent selected from the group consisting of C1-C6 alkyl groups, a C5-C10 alicyclic hydrocarbon group, a hydroxyl group, an amino group, and a C1-C6 alkoxy group, (C1-1)
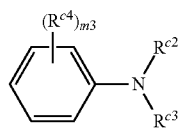

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3;

(C2)

(C3)
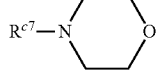

(C4)
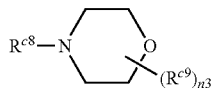

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8, (C5)
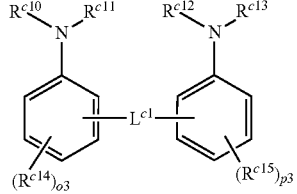

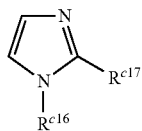
(C6)

wherein each of $R^{c10}$, $R^{c11}$, $R^{c12}$, $R^{c13}$ and $R^{c16}$ is defined same as $R^{c1}$ each of $R^{c14}$, $R^{c15}$ and $R^{c17}$ is defined same as $R^{c4}$,
$L^{c1}$ represents a C1-C6 alkanediyl group, —CO—, —C(=NH)—, —S— or a combination thereof, and o3 and p3 respectively represent an integer of 0 to 3,

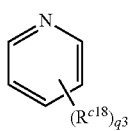
(C7)

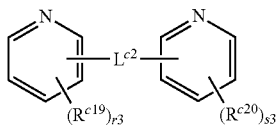
(C8)

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldibutylamine, methyldicyclohexylamine, methyldiheptylamine, methyldioctylamine, methyldinonylamine, methyldidecylamine, ethyldibutylamine, ethydipentylamine, ethyldidecylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3-r-dimethyldiphenylmethane and 4,4'-diamino-3,3'-dimethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 5%, preferably 0.01 to 3%, more preferably 0.01 to 1% by weight based on sum of solid component.

The photoresist composition may further comprise a resin which has a structural unit derived from a monomer having no acid-labile group but having a fluorine atom and which has no structural unit derived from the compound represented by formula (I). The resin having a fluorine atom but no acid-labile group as a side chain can be produced by polymerizing a compound which has a fluorine atom but no acid-labile group, preferably by polymerizing the compound represented by formula (a4-1) in a manner of radical polymerization or known methods. Such resin may be monopolymer or copolymer.

The resin usually has 8,000 or more of the weight-average molecular weight, preferably 10,000 or more of the weight-average molecular weight. The resin usually has 80,000 or less of the weight-average molecular weight, preferably has 60,000 or less of the weight-average molecular weight. The weight-average molecular weight can be measured with known methods such as liquid chromatography, gas chromatography or gel permeation chromatography.

The photoresist composition of the present invention usually includes 0.1 to 10% by weight or more of the resin based on sum of solid component. The photoresist composition of the present invention usually includes 0.3 to 5% by weight or less of the resin having a structural unit derived from a monomer having no acid-labile group but having a fluorine atom based on sum of solid component.

The photoresist compositions of the present invention contain a solvent.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing a solvent, an acid generator, and a resin of the present invention, and if necessary a basic compound, another resin and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

The method of the present invention comprises the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film to form a photoresist pattern.

The applying of the photoresist composition on a substrate is usually conducted using a conventional apparatus such as spin coater. The photoresist composition is preferably filtrated with filter having 0.003 µm to 0.2 µm of a pore size before applying.

Examples of the substrate include a silicon wafer or a quartz wafer on which a sensor, a circuit, a transistor or the like is formed. The substrate may be coated with a reflect-preventing layer such as one containing hexamethyldisilazane. For forming the reflect-preventing layer, such composition for organic reflect-preventing layer as available on the market can be used.

The photoresist film is usually formed by heating the coat layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film is exposed to radiation using an exposure system. The exposure is usually conducted through a mask having a pattern corresponding to the desired photoresist pattern.

Examples of the exposure source include a light source radiating laser light in a 0V-region such as a KrF excimer laser (wavelength: 248 nm), an ArF excimer laser (wavelength: 193 nm) and a F2 laser (wavelength: 157 nm), and a light source radiating harmonic laser light in a fax UV region or a vacuum UV region by wavelength conversion of laser light from a solid laser light source (such as YAG or semiconductor laser). The exposure source may be electric beam or extremely ultraviolet (EUV).

The step of baking of the exposed photoresist film is so called post-exposure bake, which is conducted with heating means such as hot plates. The temperature of baking of the exposed photoresist film is preferably 50 to 200° C., and more preferably 70 to 150° C.

The development of the baked photoresist film is usually carried out with alkaline developer using a development apparatus. The development can be conducted by contacting the baked photoresist film into with an aqueous alkaline solution to thereby remove the film at exposed area from the substrate while remain the film at unexposed area, forming the photoresist pattern. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the water remained on the photoresist pattern and on the substrate is preferably removed.

The photoresist composition of the present invention is suitable for KrF excimer laser lithography, ArF excimer laser lithography, EUV exposure lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [Apparatus: HTC-8120GPC, manufactured by TOSOH CORPORATION, Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene (TOSOH CORPORATION) as a standard reference material.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD). Hereinafter, the value of the peak in the mass spectrometry is referred to as "MASS".

Example 1

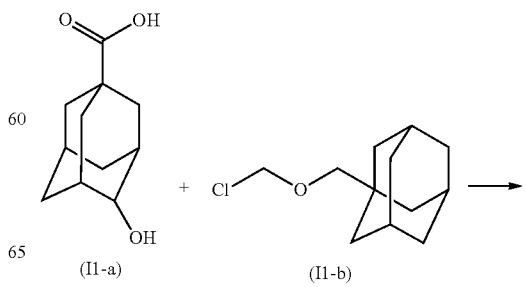

-continued

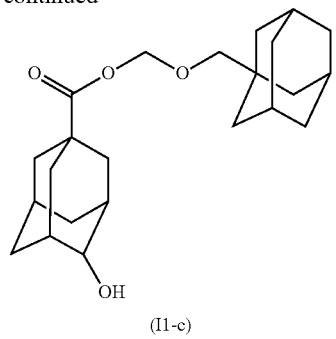
(I1-c)

Feeding 5 parts of the compound represented by formula (I1-a) and 25 parts of dimethylformamide into a reactor, they was stirred at 23° C. for 30 minutes, and then 3.87 parts of triethylamine was dropped thereto, followed by stirring them at 23° C. for 30 minutes, To the resulting mixture, dropped thereinto was a solution in which 6.57 parts of the compound represented by formula (I1-b) had been dissolved in 6.57 parts of dimethylformamide, followed by stirring them at 23° C. for 2 hours. To the resulting reaction mixture, 23.5 parts of deionized water and 140.99 parts of ethyl acetate were added, followed by stirring them at 23° C. for 30 minutes to separate into an organic layer. To the organic layer, 70.5 parts of deionized water was added, followed by stirring them at 23° C. for 30 minutes to separate into an organic layer.

Such washing with deionized water was further conducted six times.

The resulting organic layer was concentrated and 92.2 parts of n-heptane was added thereto to obtain 2.85 parts of the compound represented by formula (I1-c).

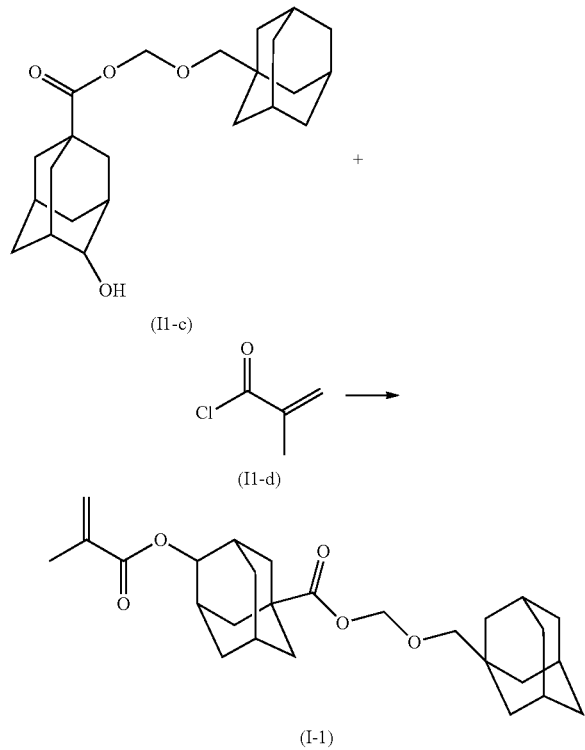

To a reactor 2.3 parts of the compound represented by formula (I1-c), 1.83 parts of N-methylpyrolidone and 20 parts of methylisobutylketone were added and stirred, and 1.28 parts of the compound represented by formula (I1-d) was further added thereto during stirring them, followed by stirring them at 60° C. for 24 hours. Then 10 parts of deionized water and 20 parts of isobutyl ketone were added thereto and stirred, followed by separating them to wash an organic layer.

Such washing was conducted three times.

The resulting organic layer was concentrated, followed by separating it with column (Merck Silicagel 60-200 mesh, solvent: ethyl acetate) to obtain 1.72 parts of the compound represented by formula (I-1).

MS (ESI(+) Spectrum): $M^+$ 442.3

Example 2

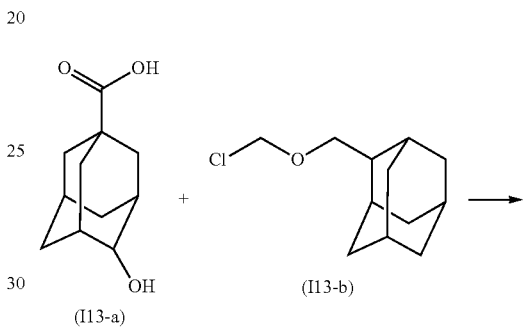

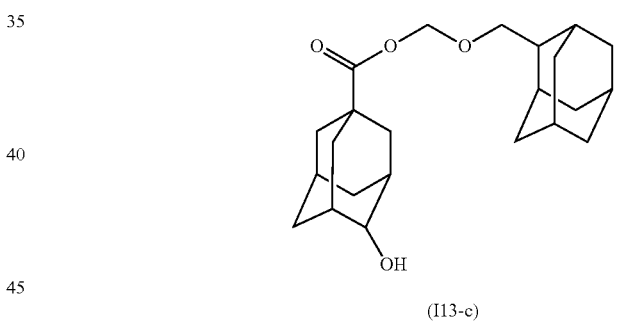

Into a reactor, 5 parts of the compound represented by formula (I13-a) and 25 parts of dimethylformamide were fed and stirred at 23° C. for 30 minutes. Thereto 3.87 parts of triethylamine was dropped and stirred at 23° C. for 30 minutes. To the resulting mixture, dropped over 30 minutes was a solution in which 6.57 parts of the compound represented by formula (I13-b) was dissolved in 6.57 parts of dimethylformamide, stirring them at 23° C. for 2 hours. To the reaction mixture, 23.5 parts of deionized water and 140.99 parts of ethyl acetate were added and stirred at 23° C. for 30 minutes, followed by separating into an organic layer. To the organic layer, 70.5 parts of deionized water was fed and stirred at 23° C. for 30 minutes, followed by separating into an organic layer. Such washing with water was further conducted six times.

The resulting reaction mixture was concentrated and 90 parts of n-heptane was added to the resulting concentrates, followed by filtrating it to obtain 3.12 parts of the compound represented by formula (I13-c).

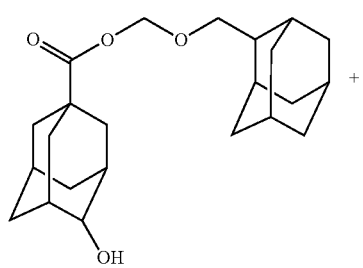

(I13-c)

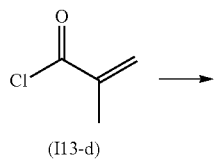

(I13-d)

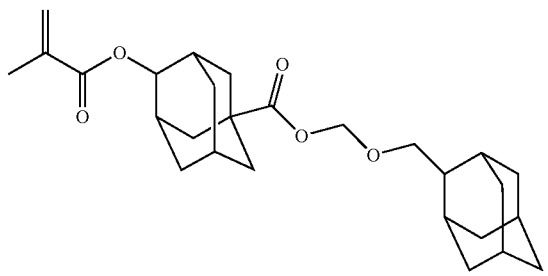

(I-13)

To a reactor, 2.3 parts of the compound represented by formula (I13-c), 1.83 parts of N-methylpyrollidine and 20 parts of methylisobutylketone were fed, then 1.28 parts of the compound represented by formula (I13-d) was added thereto during stirring them, followed by stirring the mixture at 60° C. for 24 hours. Then 10 parts of deionized water and 20 parts of methylisobutylketone were added to the resulting mixture, stirred and separated to thereby wash with water. Such washing with water was conducted three times.

The resulting organic layer was concentrated, followed by separating it with column (Merck Silicagel 60-200 mesh, solvent:

ethyl acetate) to obtain 1.98 parts of the compound represented by formula (I-13).

MS (ESI(+) Spectrum): M⁺ 442.3

Example 3

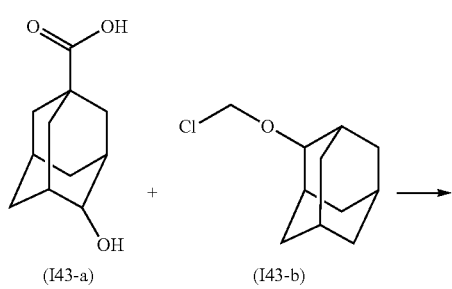

(I43-a)     (I43-b)

-continued

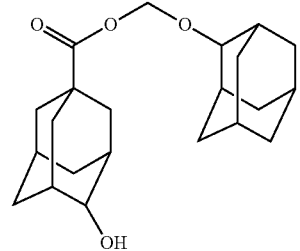

(I43-c)

Feeding 5 parts of the compound represented by formula (I43-a) and 25 parts of dimethylformamide into a reactor, they were stirred at 23° C. for 30 minutes, 3.87 parts of triethylamine was dropped thereto, followed by stirring them at 23° C. for 30 minutes. To the resulting mixture, dropped was a solution in which 6.14 parts of the compound represented by formula (I43-b) was dissolved in 6.14 parts of dimethylformamide over 30 minutes, followed by stirring them at 23° C. for 2 hours. To the reaction mixture, adding 25 parts of deionized water and 150 parts of ethyl acetate, they were stirred at 23° C. for 30 minutes, followed by separating into an organic layer. Such washing with water was conducted further five times. Concentrating the resulting reaction mixture, 92.2 parts of n-heptane was fed thereto and stirred, followed by filtrating it to obtain 2.69 parts of compound represented by formula (I43-c).

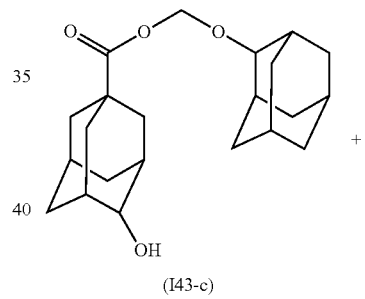

(I43-c)

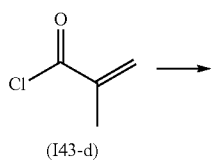

(I43-d)

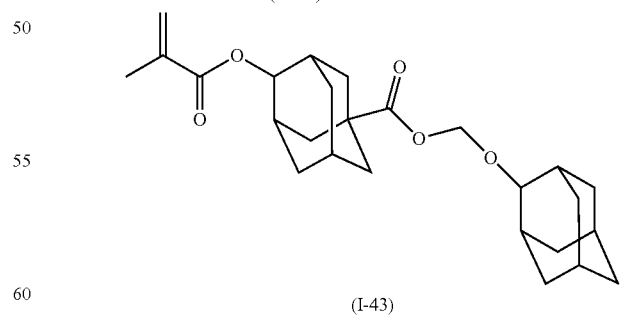

(I-43)

To a reactor 2.21 parts of the compound represented by formula (I43-c), 1.83 parts of N-methylpyrrolidine and 20 parts of methylisobutyl ketone were fed, 1.28 parts of the compound represented by formula (I43-d) was added under stirring and then further stirred at 60° C. for 24 hours. Then 10 parts of deionized water and 20 parts of methylisobutylketone were added and stirred to separate into an organic layer. Such washing with water was conducted three times.

The resulting organic layer was concentrated, followed by separating it with column (Merck Silicagel 60-200 mesh, solvent: ethyl acetate) to obtain 1.59 parts of the compound represented by formula (I-43).

MS (ESI(+) Spectrum): M$^+$ 428.3

Example 4

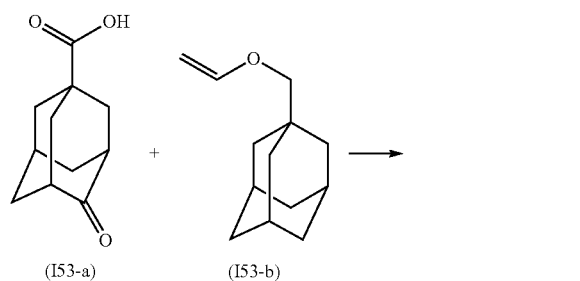

(I53-a)  (I53-b)

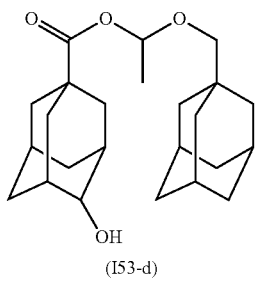

(I53-c)

Feeding 5 parts of the compound represented by formula (I53-a) and 35 parts of chloroform into a reactor, they were stirred at 23° C. for 30 minutes, and then added thereto was a mixture of 0.0012 parts of camphorsulfonic acid and 0.5988 parts of chloroform, followed by stirring, them at 23° C. for 30 minutes. To the resulting mixture, dropped was a solution in which 5.17 parts of the compound represented by formula (I53-b) was dissolved in 10.34 parts of chloroform over 30 minutes, followed by stirring them at 23° C. for 17 hours.

Then 21.63 parts of 2% aqueous sodium hydrogen carbonate solution was added thereto and then stirred at 23° C. for 30 minutes, followed by separating into an organic layer. Thereto 22.67 parts of deionized water was fed and stirred at 23° C. for 30 minutes, followed by separating into an organic layer. Such washing with water was conducted further five times. Concentrating the resulting reaction mixture, 8.49 parts of compound represented by formula (I53-c) was obtained.

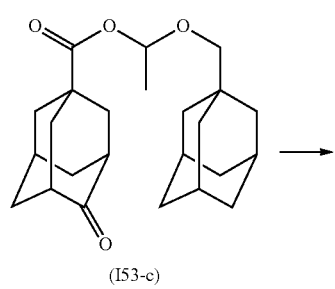

(I53-c)

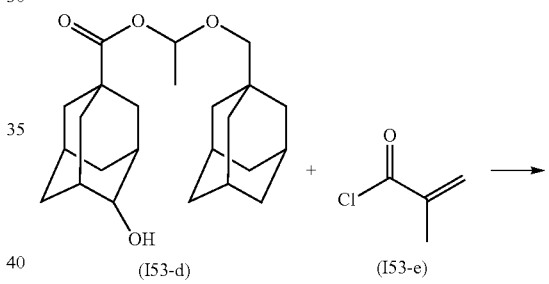

(I53-d)

Feeding 8.48 parts of the compound represented by formula (I53-c) and 42.32 parts of acetonitrile into a reactor, they were stirred at 23° C. for 30 minutes, and then a mixture of 0.42 parts of sodium borohydride and 6.23 parts of deionized water, further followed by stirring them at 5° C. for 2 hours. To the resulting mixture, 229.77 parts of ethyl acetate and 76.59 parts of deionized water were added thereto, followed by stirring them at 23° C. for 30 minutes, followed by separating into an organic layer. Such washing with Water was conducted further five times. The resulting organic layer was concentrated and 40.45 parts of n-heptane was added thereto and stirred, followed by filtrating it to obtain 7.06 parts of compound represented by formula (I53-d).

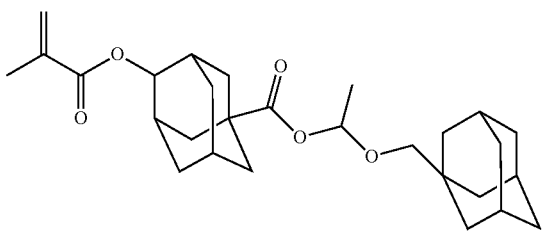

(I53-d)  (I53-e)

(I-53)

Feeding 4.07 parts of the compound represented by formula (I53-d), 1.83 parts of N-methylpyrrolidine and 20 parts of methylisobutylketone into a reactor, 1.28 parts of the compound represented by formula (I53-e) was fed thereto while they were stirred, followed by stirring them at 60° C. for 24 hours. Then 10 parts of deionized water and 20 parts of methylisobutylketone were added to the resulting reaction mixture and stirred, followed by separating an organic layer to wash it. Such wash with water was conducted three times.

The resulting organic layer was concentrated, followed by separating it with column (Merck Silicagel 60-200 mesh, solvent: ethyl acetate) to obtain 1.66 parts of the compound represented by formula (I-53).
MS (ESI(+) Spectrum): M$^+$ 456.3
Synthesis of Resin
The compounds, i.e. monomer, used for synthesis of the resin are shown bellow.
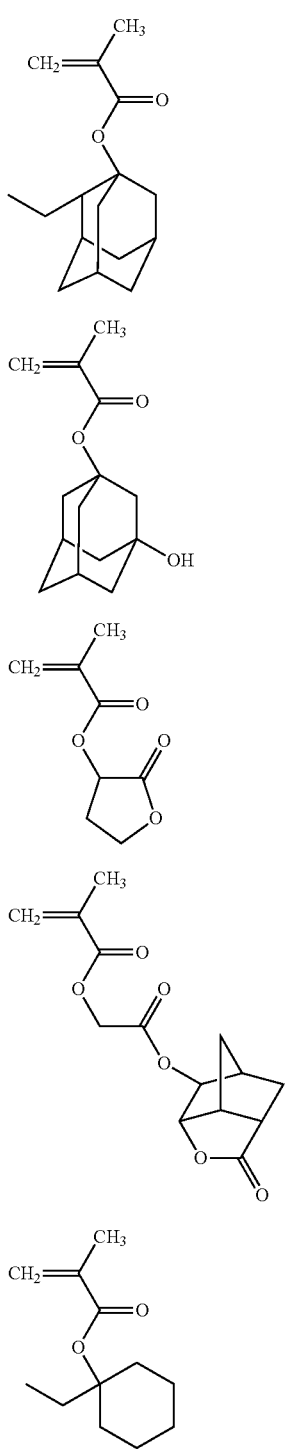
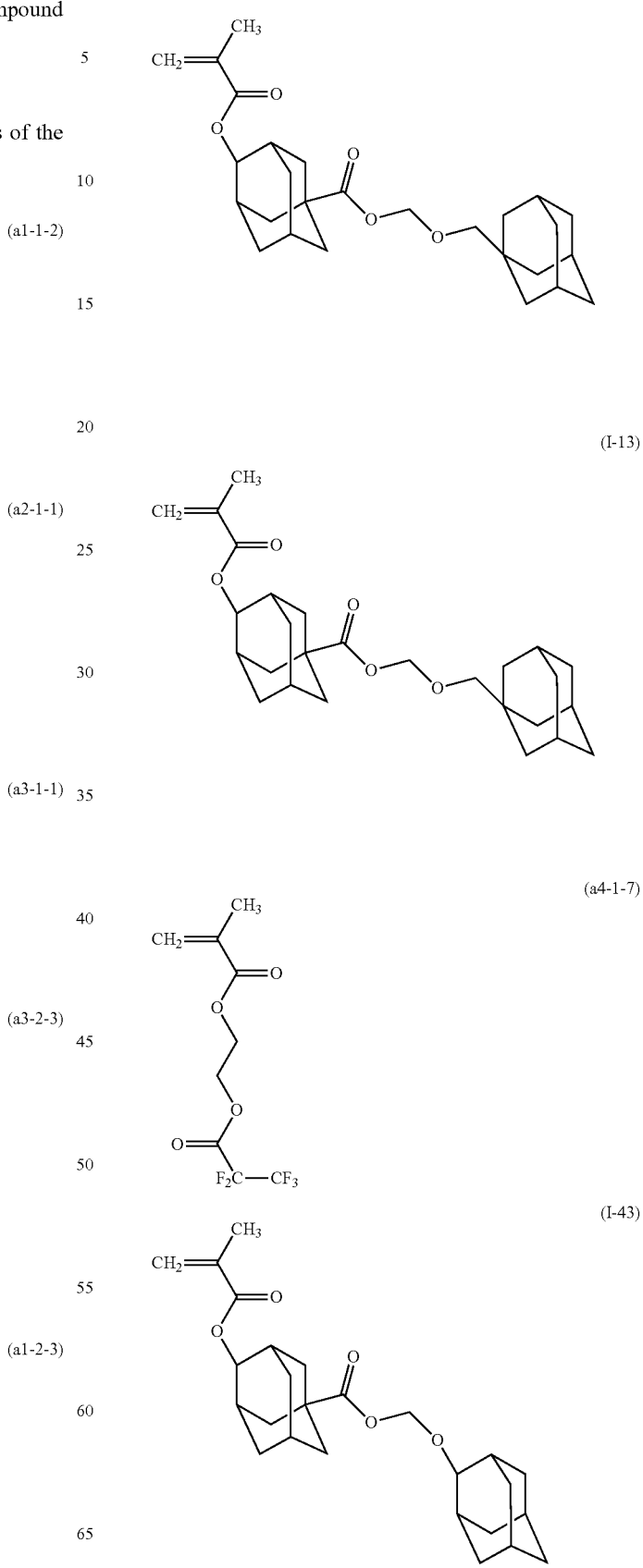

(I-53)

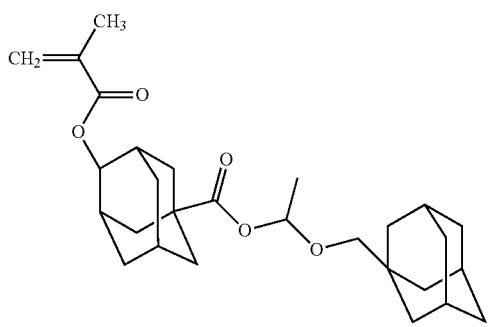

Hereinafter, the monomer of the formula (a1-1-2), the monomer of the formula (a2-1-1), the monomer of the formula (a3-1-1), the monomer of the formula (a3-2-3), the monomer of the formula (a1-2-3), the monomer of the formula (I-1), the monomer of the formula (I-13), the monomer of the formula (I-43), the monomer of the formula (I-53) and the monomer of the formula (a4-1-7) are referred to as the monomer (a1-1-2), the monomer (a2-1-1), the monomer (a3-1-1), the monomer (a3-2-3), the monomer (a1-2-3), the monomer (I-1), the monomer (I-13), the monomer (I-43), the monomer (I-53) and the monomer (a4-1-7).

Example 5

The monomer (a1-1-2), the monomer (a1-2-3), the monomer (a2-1-1), the monomer (a3-2-3), the monomer (a3-1-1) and the monomer (I-1) were mixed in their molar ratio of [monomer (a1-1-2)]/[monomer (a1-2-3)]/[monomer (a2-1-1)]/[monomer (a3-2-3)]/[monomer (a3-1-1)]/[monomer (I-1)]=30/6/0/20/30/6, and further added thereto was dioxane in an amount of 1.5 weight parts relative to the total weight of the monomers.

To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about 7.7×10³ was obtained at yield 71%. This resin is called as resin A1.

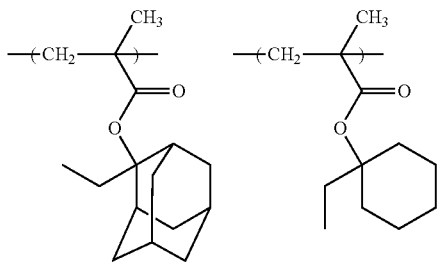

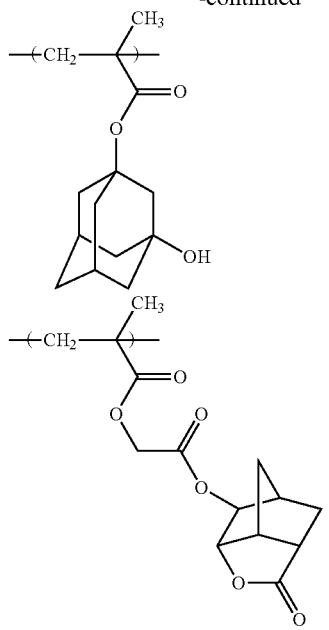

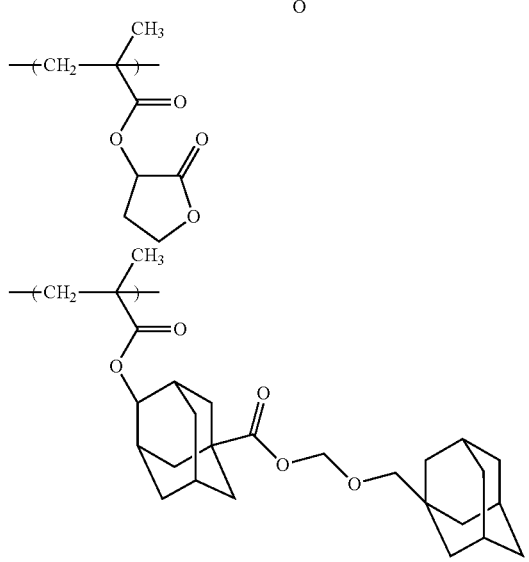

Example 6

The monomer (a1-1-2), the monomer (a2-1-1), the monomer (a3-1-1), and the monomer (I-1) were mixed in their molar ratio of [monomer (a1-1-2)]/[monomer (a2-1-1)]/[monomer (a3-1-1)]/[monomer (I-1)]=35/25/25/15, and further added thereto was dioxane in an amount of 1.5 weight parts relative to the total weight of the monomers. To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about 7.6×10³ was obtained at yield 73%. This resin is called as resin A2.

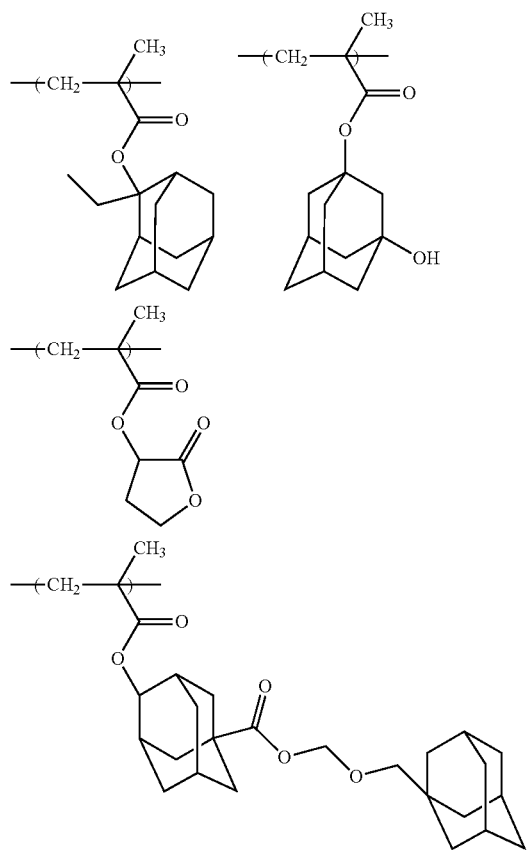

Example 7

The monomer (a1-1-2), the monomer (a1-2-3), the monomer (a2-1-1), the monomer (a3-2-3), the monomer (a3-1-1) and the monomer (I-13) were mixed in their molar ratio of [monomer (a1-1-2)]/[monomer (a1-2-3)]/[monomer (a2-1-1)]/[monomer (a3-2-3)]/[monomer (a3-1-1)]/[monomer (I-13)]=30/6/8/20/30/6, and further added thereto was dioxane in an amount of 1.5 weight parts relative to the total weight of the monomers.

To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about 7.8×10³ was obtained at yield 73%. This resin is called as resin A3.

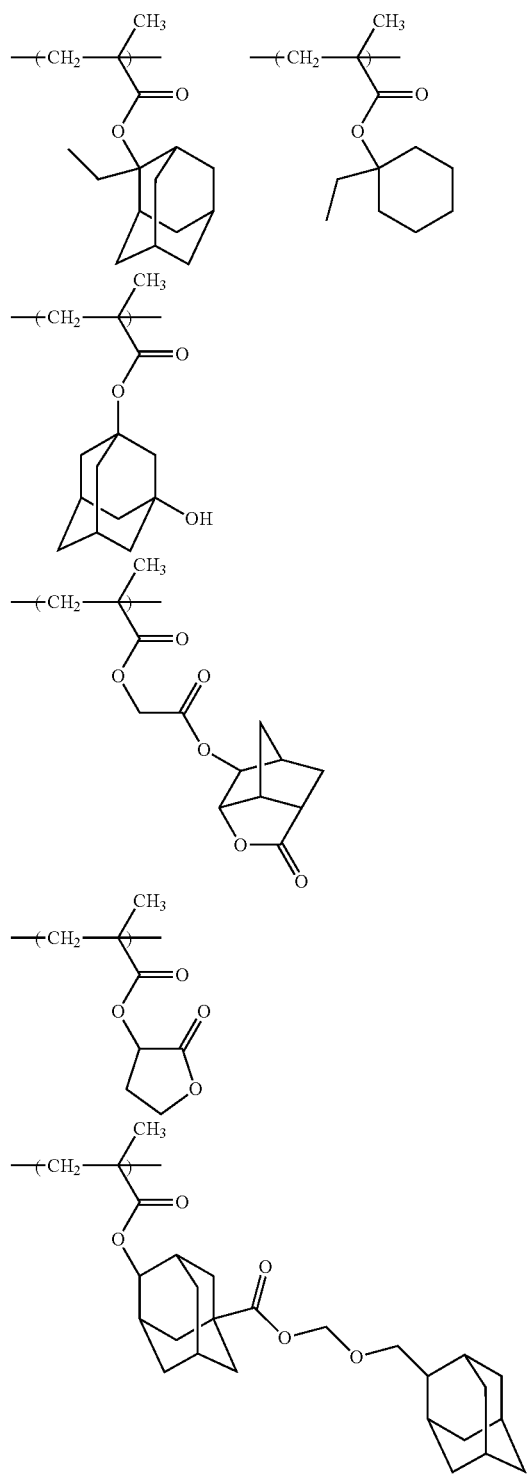

Example 8

The monomer (a1-1-2), the monomer (a2-1-1), the monomer (a3-1-1), and the monomer (I-13) were mixed in their molar ratio of [monomer (a1-1-2)]/[monomer (a2-1-1)]/[monomer (a3-1-1)]/[monomer (I-13)]=35/25/25/15, and further added thereto was dioxane in an amount of 1.5 weight parts relative to the total weight of the monomers. To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about $8 \times 10^3$ was obtained at yield 76%. This resin is called as resin A4.

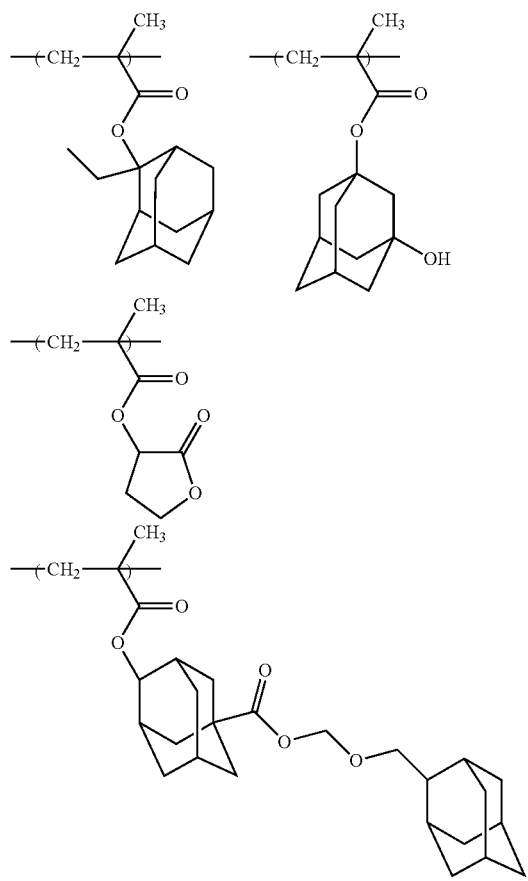

Synthesis Example 1

The monomer (a1-1-2), the monomer (a2-1-1) and the monomer (a3-1-1), were mixed in their molar ratio of [monomer (a1-1-2)]/[monomer (a2-1-1)]/[monomer (a3-1-1)]=50/25/25, and further added thereto was dioxane in an amount of 1.5 weight parts relative to the total weight of the monomers.

To the resulting solution, 1 mole % of azobisisobutyronitrile and 3 mole % of azo(2,4-dimethylvaleronitrile) were added relative to the total molar amount all monomers as initiators, and heated at 80° C. for about 8 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about $9.2 \times 10^3$ was obtained at yield 60%. This resin is called as resin A5.

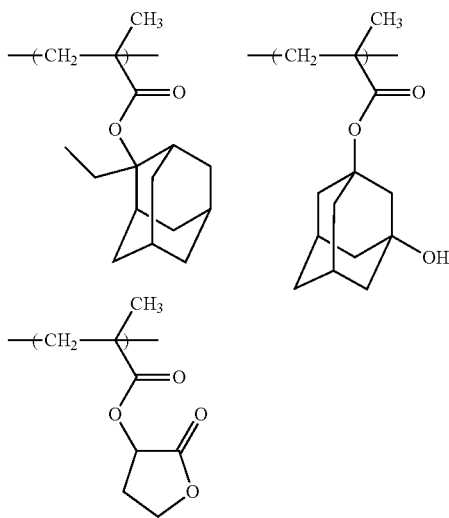

Example 9

The monomer (a1-1-2), the monomer (a1-2-3), the monomer (a2-1-1), the monomer (a3-2-3), the monomer (a3-1-1), and the monomer (I-43) were mixed in their molar ratio of [monomer (a1-1-2)]/[monomer (a1-2-3)]/[monomer (a2-1-1)]/[monomer (a3-2-3)]/[monomer (a3-1-1)]/[monomer (I-43)]=30/6/8/20/30/6, and further added thereto was dioxane in an amount of 1.5 weight parts relative to the total weight of the monomers.

To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about $8.2 \times 10^3$ was obtained at yield 85%. This resin is called as resin A6.

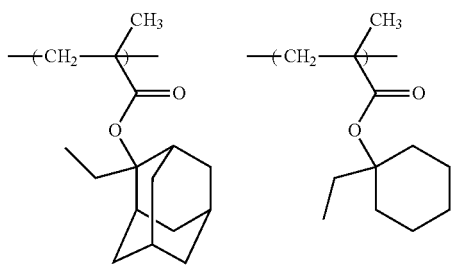

137

-continued

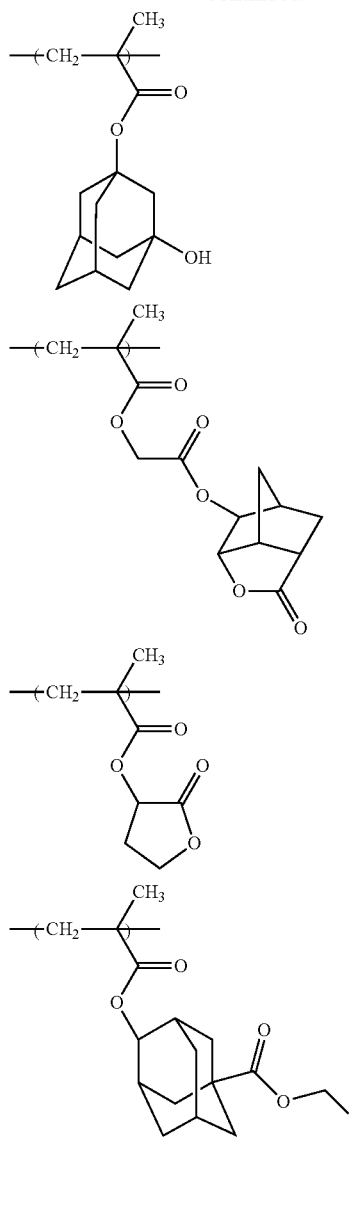

Example 10

The monomer (a1-1-2), the monomer (a1-2-3), the monomer (a2-1-1), the monomer (a3-2-3), the monomer (a3-1-1), and the monomer (I-53) were mixed in their molar ratio of [monomer (a1-1-2)]/[monomer (a1-2-3)]/[monomer (a2-1-1)]/[monomer (a3-2-3)]/[monomer (a3-1-1)]/[monomer (I-53)]=30/6/8/20/30/6, and further added thereto was dioxane in an amount of 1.5 weight parts relative to the total weight of the monomers.

To the resulting solution, 1 mole % of azobisisobutyronitrile and 3 mole % of azo(2,4-dimethylvaleronitrile) were added relative to the total molar amount all monomers as initiators, and heated at 75° C. for about 5 hours. Into the resulting reaction mixture, a large amount of mixture of water

138 and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural units and a weight-average molecular weight of about $8.1 \times 10^3$ was obtained at yield 81%. This resin is called as resin A7.

Synthesis Example 2

To the monomer (a4-1-7), dioxane was added in an amount of 1.5 weight parts relative to the total weight of the monomer.

To the resulting solution, 0.7 mole % of azobisisobutyronitrile and 2.1 mole % of azo(2,4-dimethylvaleronitrile) were added relative to the total molar amount all monomers as initiators, and heated at 75° C. for about 5 hours. Into the resulting reaction mixture, a large amount of mixture of water and methanol was poured to cause precipitation, followed by filtrating the resulting mixture. Then the following procedure was conducted twice: The filtrate was dissolved in dioxane, and the mixture of water and methanol was poured into the resulting solution to cause precipitation, followed by filtrating the resulting mixture.

As a result, a polymer having the following structural unit and a weight-average molecular weight of about $1.8 \times 10^3$ was obtained at yield 77. This resin is called as resin D1.

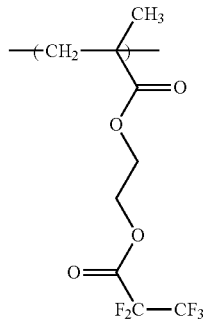

Examples 11 to 23 and Comparative Example 1

Preparation of Photoresist Composition

The resin, the acid generator and the basic compound were dissolved in the solvent as shown in Table 1, and the resulting mixture was further filtrated-through a fluorine resin filter having pore diameter of 0.2 μm, to prepare photoresist compositions shown in Table 1.

<Resin>
Resin A1, Resin A2, Resin A3, Resin A4, Resin A5, Resin A6, Resin A7, Resin D1
<Acid Generator>
B1:

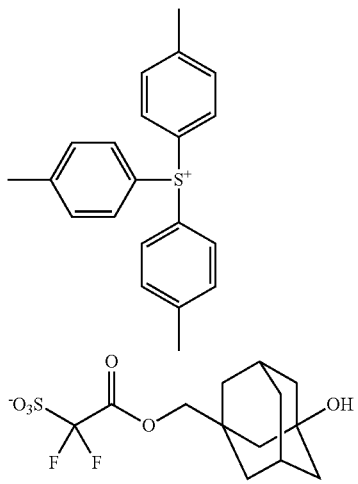

B2:

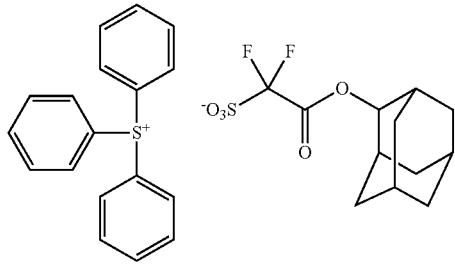

<Quencher>
Basic Compound C1: 2,6-diisopropylaniline
<Solvent>

| propylene glycol monomethyl ether acetate | 265 parts |
| --- | --- |
| propylene glycol monomethyl ether | 20 parts |
| 2-heptan | 20 parts |
| γ-butyrolactone | 3.5 parts |

TABLE 1

| | Acid generator (Parts) | Resin (Parts) | Quencher (Parts) | PB/PEB |
| --- | --- | --- | --- | --- |
| Ex. 11 | A1 = 10 | B1 = 1 | C1 = 0.07 | 110° C./105° C. |
| Ex. 12 | A2 = 10 | B1 = 1 | C1 = 0.07 | 110° C./105° C. |
| Ex. 13 | A3 = 10 | B1 = 1 | C1 = 0.07 | 110° C./105° C. |
| Ex. 14 | A4 = 10 | B1 = 1 | C1 = 0.07 | 110° C./105° C. |
| Ex. 15 | A1/D1 = 10/0.7 | B1 = 1 | C1 = 0.07 | 110° C./105° C. |
| Ex. 16 | A2/D1 = 10/0.7 | B1 = 1 | C1 = 0.07 | 110° C./105° C. |
| Ex. 17 | A3/D1 = 10/0.7 | B1 = 1 | C1 = 0.07 | 110° C./105° C. |
| Ex. 18 | A4/D1 = 10/0.7 | B1 = 1 | C1 = 0.07 | 110° C./105° C. |
| Ex. 19 | A4 = 10 | B2 = 1 | C1 = 0.07 | 110° C./105° C. |
| Ex. 20 | A6 = 10 | B1 = 1 | C1 = 0.07 | 110° C./105° C. |
| Ex. 21 | A6/D1 = 10/0.7 | B1 = 1 | C1 = 0.07 | 110° C./105° C. |
| Ex. 22 | A7 = 10 | B1 = 1 | C1 = 0.07 | 110° C./105° C. |

TABLE 1-continued

| | Acid generator (Parts) | Resin (Parts) | Quencher (Parts) | PB/PEB |
| --- | --- | --- | --- | --- |
| Ex. 23 | A7/D1 = 10/0.7 | B1 = 1 | C1 = 0.07 | 110° C./105° C. |
| Comp. Ex. 1 | A5 = 10 | B2 = 1 | C1 = 0.07 | 110° C./105° C. |

(Producing Photoresist Pattern and its Evaluation)

The photoresist compositions of examples and comparative examples were evaluated by measuring defects of photoresist patterns obtained from the compositions and by measuring mask error factor (MEF). The photoresist compositions of examples and comparative examples are sometimes correctively referred to as "photoresist compositions".

(Producing Photoresist Pattern)

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating.

Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 1 for 60 seconds. Using an ArF excimer stepper for immersion exposure ("XT: 1900Gi" manufactured by ASML, NA=1.35, ¾ Annular, X—Y polarization), each wafer thus formed with the respective resist film was subjected to line and space pattern exposure with the exposure quantity being varied stepwise. Ultrapure water was used as an immersion medium.

After the exposure, each wafer was subjected to post-exposure baking on a hotplate at a temperature shown in the column "PEB" in Table 1 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 2.

Effective Sensitivity (ES): It was expressed as the amount of exposure that the line width of the line and space pattern of 50 nm became 1:1 after exposure through line and space pattern mask and development.

Mask Error Factor (MEF):

The photoresist pattern was made by such exposure as the line width of the line and space pattern became 50 nm after exposure through line and space pattern mask (1:1) in which the pitch size was 100 nm and the mask size for line pattern was 50 nm and development. Such exposure was conducted with line and space pattern mask in which the pitch size was 100 nm and the mask size for line pattern was 48 nm, 50 nm or 52 nm to produce photoresist patterns. The results were determined by plotting the mask size on the abscissas and the line width of line pattern on the ordinate and measuring the slop of the plotted line. In case that the patterns provide a slope not larger than 2.3, it was evaluated as "⊚". In case that the patterns provide a slope larger than 2.3 but not larger than 3, it was evaluated as "○". In case that the patterns provide a slope larger than 3, it was evaluated as "X".

The results are shown in Table 2. In the table, the values in parentheses are of slopes.

TABLE 2

| Ex. No. | MEF |
|---|---|
| Ex. 11 | ⊚ (2.24) |
| Ex. 12 | ○ (2.41) |
| Ex. 13 | ⊚ (2.25) |
| Ex. 14 | ○ (2.44) |
| Ex. 15 | ⊚ (2.28) |
| Ex. 16 | ○ (2.39) |
| Ex. 17 | ⊚ (2.23) |
| Ex. 18 | ○ (2.45) |
| Ex. 19 | ○ (2.94) |
| Ex. 20 | ⊚ (2.13) |
| Ex. 21 | ⊚ (2.16) |
| Ex. 22 | ⊚ (2.26) |
| Ex. 23 | ⊚ (2.27) |
| Compar. Ex. 1 | X (3.21) |

The photoresist patterns obtained from the photoresist compositions of the present invention show small MEF, while the photoresist patterns obtained from the photoresist compositions of comparative examples show large MEF.

The photoresist compositions of the present invention are useful for semiconductor microfiblication.

What is claimed is:

1. A photoresist composition, which comprises a resin comprising a structural unit derived from a compound represented by formula (I):

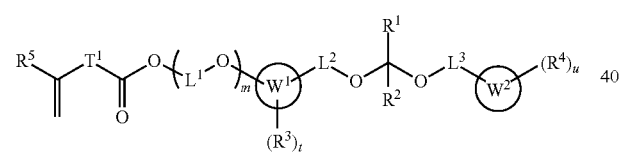

(I)

wherein $T^1$ represents a single bond or a C6-C14 aromatic hydrocarbon group, $L^1$ represents a C1-C17 divalent saturated hydrocarbon group in which a methylene group may be replaced by an oxygen atom or a carbonyl group, $L^2$ and $L^3$ each independently represent a single bond or a C1-C6 divalent saturated hydrocarbon group in which a methylene group may be replaced by an oxygen atom or a carbonyl group, ring $W^1$ and ring $W^2$ each independently represent a C3-C36 hydrocarbon ring, $R^1$ and $R^2$ each independently represent a hydrogen atom, a hydroxyl group, or C1-C6 alkyl group, $R^3$ and $R^4$ each independently represent a hydroxyl group, or C1-C6 alkyl group, $R^5$ represents a hydroxyl group or a methyl group, m represents 0 or 1, and t and u each independently represent an integer of 0 to 2;

a resin having a structural unit derived from a monomer having no acid-labile group but having a fluorine atom, said monomer being represented by formula (a-4-1)

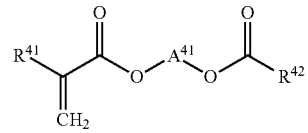

(a4-1)

wherein $R^{41}$ represents a hydrogen atom or a methyl group, $A^{41}$ represents a moiety represented by formula (a-4-g1):

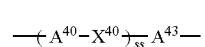

(a4-g1)

in which ss represents an integer of 0 to 2, $A^{40}$ and $A^{43}$ respectively represent a C1-C5 aliphatic hydrocarbon group which may have a substituent, $X^{40}$ represents an oxygen atom, a carbonyl group, a carbonyloxy group, or an oxycarbonyl group, and $R^{42}$ represents a C1-C18 fluorine-containing aliphatic hydrocarbon group in which a methylene group may be replaced by —O— or —CO—;

an acid generator; and a solvent.

2. The photoresist composition according to claim 1, wherein the acid generator is a salt represented by formula (B1)

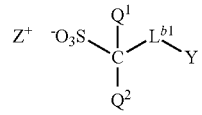

(B1)

wherein $Q^1$ and $Q^2$ respectively represent a fluorine atom or a C1-C6 perfluoroalkyl group, $L^{b1}$ represents a methylene group or a C1-C17 saturated hydrocarbon group in which a methylene group may be replaced by an oxygen atom or a carbonyl group, Y represents a C1-C18 alkyl group which may have a substituent or a C3-C18 alicyclic hydrocarbon group which may have a substituent, where a methylene of the alkyl group and a methylene of the alicyclic hydrocarbon group may be replaced respectively by an oxygen atom, a sulfonyl group or a carbonyl group, and $Z^+$ represents an organic cation.

3. The photoresist composition according to claim 2, wherein Y represents a C3-C18 alicyclic hydrocarbon group which may have a substituent.

4. A process for producing a photoresist pattern comprising the following steps (1) to (5):

(1) a step of applying the photoresist composition according to claim 1 on a substrate, (2) a step of forming a photoresist film by conducting drying, (3) a step of exposing the photoresist film to radiation, (4) a step of baking the exposed photoresist film, and (5) a step of developing the baked photoresist film thereby to form a photoresist pattern.

* * * * *